US006575979B1

(12) United States Patent
Cragg

(10) Patent No.: US 6,575,979 B1
(45) Date of Patent: Jun. 10, 2003

(54) METHOD AND APPARATUS FOR PROVIDING POSTERIOR OR ANTERIOR TRANS-SACRAL ACCESS TO SPINAL VERTEBRAE

(75) Inventor: Andrew H. Cragg, Edina, MN (US)

(73) Assignee: Axiamed, Inc., Wrightsville Beach, NC (US)

(*) Notice: Subject to any disclaimer, the term of this patent is extended or adjusted under 35 U.S.C. 154(b) by 146 days.

(21) Appl. No.: 09/640,222

(22) Filed: Aug. 16, 2000

Related U.S. Application Data

(60) Provisional application No. 60/182,748, filed on Feb. 16, 2000.

(51) Int. Cl.[7] ............................................. A61F 5/00
(52) U.S. Cl. ................................. 606/86; 606/61
(58) Field of Search ................. 606/86, 87, 96, 606/97, 98, 102, 99, 104, 108, 190, 191, 61, 170; 623/17.11, 17.16; 128/898

(56) References Cited

U.S. PATENT DOCUMENTS

| 3,892,232 A | * 7/1975 | Neufeld |
| 4,170,990 A | 10/1979 | Baumgart et al. ........ 128/92 B |

(List continued on next page.)

FOREIGN PATENT DOCUMENTS

| EP | 0 611 116 B1 | 4/1994 |
| WO | WO 95/22285 | 8/1995 |
| WO | WO 97/40878 | 11/1997 |
| WO | WO 98/38918 | 9/1998 |
| WO | WO 00/67650 | 11/2000 |
| WO | WO 02/09801 A1 | 2/2002 |
| WO | WO 02/13732 A2 | 2/2002 |
| WO | WO 02/34120 A2 | 5/2002 |

OTHER PUBLICATIONS

John L. Emmett, M.D., M.S. (Urology), David M. Witten, M.D., M.S. (Radiology)—vol. 1, Third Edition—Clinical Urography—An Atlas and Textbook of Roentgenologic Diagnosis—1971—Phneumography (Retroperitoneal Gas [Air] Insufflation; Perirenal Insufflation; Presacral Insufflation).

(List continued on next page.)

*Primary Examiner*—Pedro Philogene
(74) *Attorney, Agent, or Firm*—Knobbe, Martens, Olson & Bear, LLP

(57) ABSTRACT

Methods and apparatus for providing percutaneous access to the human sacral and lumbar vertebrae in alignment with a visualized, trans-sacral axial instrumentation/fusion (TASIF) line in a minimally invasive, low trauma, manner are disclosed. A number of related TASIF methods and surgical tool sets are provided by the present invention that are employed to form a percutaneous pathway from an anterior or posterior skin incision to a respective anterior or posterior target point of a sacral surface. The percutaneous pathway is generally axially aligned with an anterior axial instrumentation/fusion line (AAIFL) or a posterior axial instrumentation/fusion line (PAIFL) extending from the respective anterior or posterior target point through at least one sacral vertebral body and one or more lumbar vertebral body in the cephalad direction and visualized by radiographic or fluoroscopic equipment. The anterior or posterior percutaneous pathway so formed enables introduction of further tools and instruments for boring one or more respective anterior or posterior TASIF bore in the cephalad direction through the one or more vertebral bodies and intervening discs, if present. A single anterior or posterior TASIF bore is preferably aligned axially with the respective visualized AAIFL or PAIFL, and plural anterior or posterior TASIF bores are preferably aligned in parallel with the respective visualized AAIFL or PAIFL. Introduction of spinal implants and instruments is enabled by the provision of the percutaneous pathway in accordance with the present invention and formation of the anterior or posterior TASIF bore(s).

127 Claims, 36 Drawing Sheets

U.S. PATENT DOCUMENTS

| | | | |
|---|---|---|---|
| 4,401,112 A | 8/1983 | Rezaian | 128/92 B |
| 4,453,539 A | 6/1984 | Raftopoulos et al. | 128/92 BC |
| 4,553,273 A | 11/1985 | Wu | 623/18 |
| 4,554,914 A | 11/1985 | Kapp et al. | |
| 4,573,448 A * | 3/1986 | Kambin | |
| 4,636,217 A | 1/1987 | Ogilvie et al. | 623/17 |
| 4,844,088 A | 7/1989 | Kambin | |
| 4,862,891 A * | 9/1989 | Smith | |
| 5,059,193 A | 10/1991 | Kuslich | 606/61 |
| 5,062,850 A | 11/1991 | MacMillan et al. | |
| 5,171,279 A | 12/1992 | Mathews | |
| 5,190,546 A | 3/1993 | Jervis | 606/78 |
| 5,242,443 A | 9/1993 | Kambin | |
| 5,242,444 A | 9/1993 | MacMillan | |
| 5,290,289 A | 3/1994 | Sanders et al. | 606/61 |
| 5,336,223 A | 8/1994 | Rogers | |
| 5,357,983 A | 10/1994 | Mathews | |
| 5,366,457 A | 11/1994 | McGuire et al. | |
| 5,395,317 A | 3/1995 | Kambin | |
| 5,396,880 A | 3/1995 | Kagan et al. | 128/6 |
| 5,415,661 A | 5/1995 | Holmes | 606/69 |
| 5,480,440 A | 1/1996 | Kambin | |
| 5,496,322 A | 3/1996 | Mathews | |
| 5,505,732 A | 4/1996 | Michelson | 606/61 |
| 5,514,137 A | 5/1996 | Coutts | 606/62 |
| 5,514,180 A | 5/1996 | Heggeness et al. | 623/17 |
| 5,545,228 A | 8/1996 | Kambin | |
| 5,558,674 A | 9/1996 | Heggeness et al. | |
| 5,569,248 A | 10/1996 | Mathews | |
| 5,571,189 A | 11/1996 | Kuslich | 623/17 |
| 5,571,190 A | 11/1996 | Ulrich et al. | |
| 5,584,887 A | 12/1996 | Kambin | |
| 5,630,816 A | 5/1997 | Kambin | |
| 5,653,708 A | 8/1997 | Howland | |
| 5,665,122 A | 9/1997 | Kambin | |
| 5,669,909 A | 9/1997 | Zdeblick et al. | |
| 5,700,291 A | 12/1997 | Kuslich et al. | 623/17 |
| 5,702,455 A | 12/1997 | Saggar | 623/17 |
| 5,713,904 A | 2/1998 | Errico et al. | 606/73 |
| 5,728,097 A | 3/1998 | Mathews | |
| 5,735,899 A | 4/1998 | Schwartz et al. | 623/17 |
| 5,741,253 A | 4/1998 | Michelson | |
| 5,741,261 A | 4/1998 | Moskovitz et al. | |
| 5,785,709 A | 7/1998 | Kummer et al. | |
| 5,792,044 A | 8/1998 | Foley et al. | |
| 5,827,328 A | 10/1998 | Butterman | 623/17 |
| 5,885,292 A | 3/1999 | Moskovitz et al. | |
| 5,888,223 A | 3/1999 | Bray, Jr. | 623/17 |
| 5,891,147 A | 4/1999 | Moskovitz et al. | |
| 5,902,231 A | 5/1999 | Foley et al. | |
| 5,906,616 A | 5/1999 | Pavlov et al. | |
| 5,954,635 A | 9/1999 | Foley et al. | |
| 5,964,761 A | 10/1999 | Kambin | |
| 5,976,146 A | 11/1999 | Ogawa et al. | 606/86 |
| 5,976,187 A | 11/1999 | Richelsoph | 623/17 |
| 5,989,256 A | 11/1999 | Kuslich et al. | 606/74 |
| 6,007,487 A | 12/1999 | Foley et al. | |
| 6,010,502 A | 1/2000 | Bagby | |
| 6,030,162 A | 2/2000 | Huebner | |
| 6,033,406 A | 3/2000 | Mathews | |
| 6,053,916 A | 4/2000 | Moore | |
| 6,056,749 A | 5/2000 | Kuslich | 606/61 |
| 6,086,589 A | 7/2000 | Kuslich et al. | 606/61 |
| 6,093,207 A | 7/2000 | Pisharodi | 623/17 |
| 6,152,871 A | 11/2000 | Foley et al. | |
| 6,162,170 A | 12/2000 | Foley et al. | |
| 6,175,758 B1 | 1/2001 | Kambin | |
| 6,176,823 B1 | 1/2001 | Foley et al. | |
| 6,206,822 B1 | 3/2001 | Foley et al. | |
| 6,206,826 B1 | 3/2001 | Mathews et al. | |
| 6,210,412 B1 | 4/2001 | Michelson | |
| 6,217,509 B1 | 4/2001 | Foley et al. | |
| 6,264,656 B1 | 7/2001 | Michelson | |
| 6,315,795 B1 | 11/2001 | Scarborough et al. | |
| 6,371,990 B1 | 4/2002 | Ferree | |
| 6,379,334 B1 | 4/2002 | Frassica | |
| 6,387,130 B1 | 5/2002 | Stone et al. | |
| 6,395,007 B1 | 5/2002 | Bhatnager et al. | |
| 6,402,750 B1 | 6/2002 | Atkinson et al. | |
| 6,447,514 B1 | 9/2002 | Stalcup et al. | |
| 6,447,518 B1 | 9/2002 | Krause et al. | |
| 2002/0022888 A1 | 2/2002 | Serhan et al. | |
| 2002/0032444 A1 | 3/2002 | Mische | |
| 2002/0038123 A1 | 3/2002 | Visotsky et al. | |
| 2002/0107573 A1 | 8/2002 | Steinberg | |

OTHER PUBLICATIONS

U.S. patent application Publication No. 2002/0082598 A1, *Percutaneous Vertebral Fusion System*, published Jun. 27, 2002.

U.S. patent application Publication No. 2002/0068939 A1, *Expandable Orthopedic Device*, published Jun. 6, 2002.

Hallett H. Mathews, M.D., "Minimally Invasive Fusion Techniques, Percutaneous Interbody Fusions," *Orthopedic Clinics of North America*, Oct. 1998, vol. 29, No. 4.

Parviz Kambin, M.D., et al., "Arthroscopic Microdiscectomy: An Alternative to Open Disc Surgery," *The Mount Sinai Journal of Medicine*, Sep. 2000, vol. 67, No. 4.

Hallett H. Mathews, M.D., et al., "Perspectives on Modern Orthopaedics, Minimally Invasive Techniques for the Treatment of Intervertebral Disk Herniation," *Journal of the American Academy of Orthopaedic Surgeons*, Mar./Apr. 2002, vol. 10, No. 2.

Parviz Kambin, M.D., "Percutaneous Spine Techniques, Diagnostic and Therapeutic Spinal Arthroscopy," *Neurosurgery Clinics of North America*, Jan. 1996, vol. 7, No. 1.

Parviz Kambin, M.D., et al., "Arthroscopic Discectomy of the Lumbar Spine," *Clincial Orthopaedics and Related Research*, Apr. 1997, No. 337.

J. J. Trambert, MD, "Percutaneous Interventions in the Presacral Space: CT–guided Precoccygeal Approach—Early Experience", *Radiology 1999*; 213:901–904.

R. Johnsson et al., "Posterolateral lumbar fusion using facet joint fixation with biodegradable rods: a pilot study", *Eur Spine J.*, (1997) 6:144–148.

R. P. Louis, MD, "Anatomy, Physiology, and Biomechanics of the Lumbopelvic Junction", *Lumbosacral and Spinopelvic Fusion*, Chapter 1 (pp. 1–11) Lippincott–Raven Pub. (1996).

M. R. Zindrick, MD et al., "Clinical Anatomy of the Lumbrosacral Junction and Pelvis" *Lumbosacral and Spinopelvic Fusion*, Chapt. 2 (pp. 13–25) Lippincott–Raven Pub. (1996).

J. W. Olgilvie, MD et al., "Overview of Fixation to the Sacrum & Pelvis in Spinal Surgery", *Lumbosacral and Spinopelvic Fusion*, Chapter 17 (pp. 191–198). Lippincott–Raven Pub. (1996).

S. A. Caruso, ME et al., "Instrumented Fusions of the Lumbosacral Spine: A Technical Overview", *Lumbosacral and Spinopelvic Fusion*, Chapter 18 (pp. 199–210) Lippincott–Raven Pub. (1996).

R. P. Louis, MD, "Lumbopelvic Fusion", *Lumbosacral and Spinopelvic Fusion*, Chapter 38 (pp. 479–492) Lippincott–Raven Pub. (1996).

J. Dove, FRCS, "The Hartshill System for the Front of the Lumbosacral Spine", *Lumbosacral and Spinopelvic Fusion*, Chapter 42 (pp. 539–543) Lippincott–Raven Pub. (1996).

P. Kambin, MD et al., "Arthroscopic Fusion of the Lumbosacral Spine", *Lumbosacral and Spinopelvic Fusion*, Chapter 44 (pp. 565–577) Lippincott–Raven Pub. (1996).

Jason A. Smith, MD, et al., "Clinical Outcome of Trans–Sacral Interbody Fusion After Partial Reduction for High–Grade L5–S1 Spondylolisthesis," *Spine*, 2001, vol. 26, No. 20, pp. 2227–2234.

Michael MacMilland, MD, et al., "Percutaneous Lumbosacral Fixation and Fusion," *Percutaneous Spine Techniques*, Jan. 1996, vol. 7, No. 1, pp. 99–106.

Curtis A. Dickman, M.D., et al., "Transpedicular screw–rod fixation of the lumbar spine: operative technique and outcome in 104 cases," *J. Neurosurg*, Dec., 1992, vol. 77, pp. 860–870.

Richard M. Slone, MD, et al., "Spinal Fixation, Part 1, Basic Hardware, and Fixation Techniques for the Cervical Spine," *RadioGraphics*, 1993, vol. 13, No. 2, pp. 341–356.

Richard M. Slone, MD, et al., "Spinal Fixation, Part 2, Fixation Techniques and Hardware for the Thoracic and Lumbosacral Spine," *RadioGraphics*, 1993, vol. 13, No. 3, pp. 521–543.

Michael MacMillan, et al., "Biomechanical Analysis of a New Anterior Spine Implant for Post–Corpectomy Instability," *Journal of Spinal Disorders*, 1995, vol. 8, No. 1, pp. 56–61.

\* cited by examiner

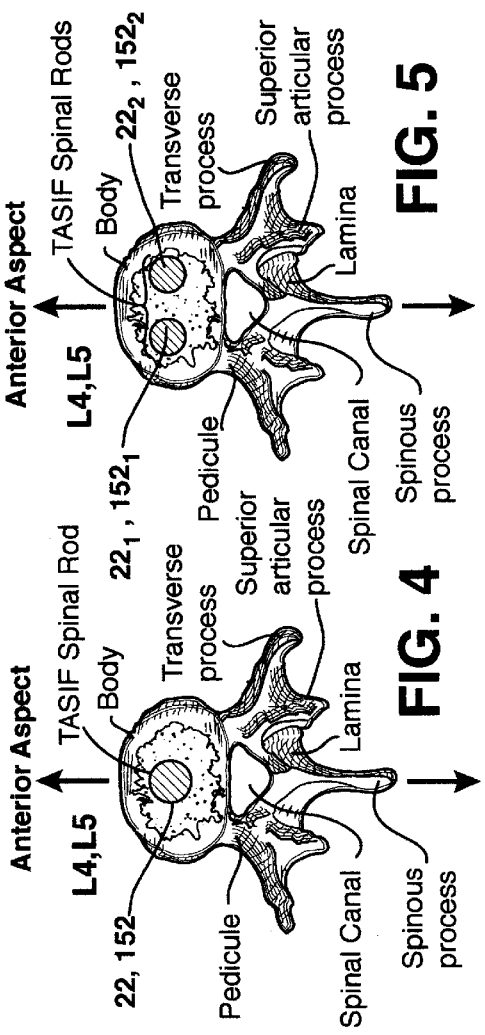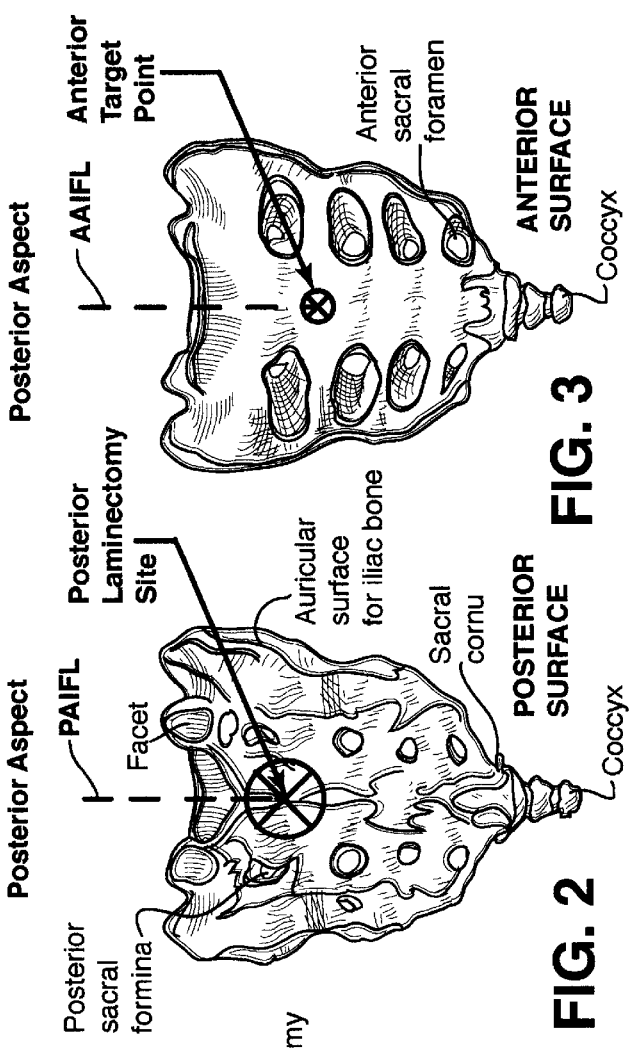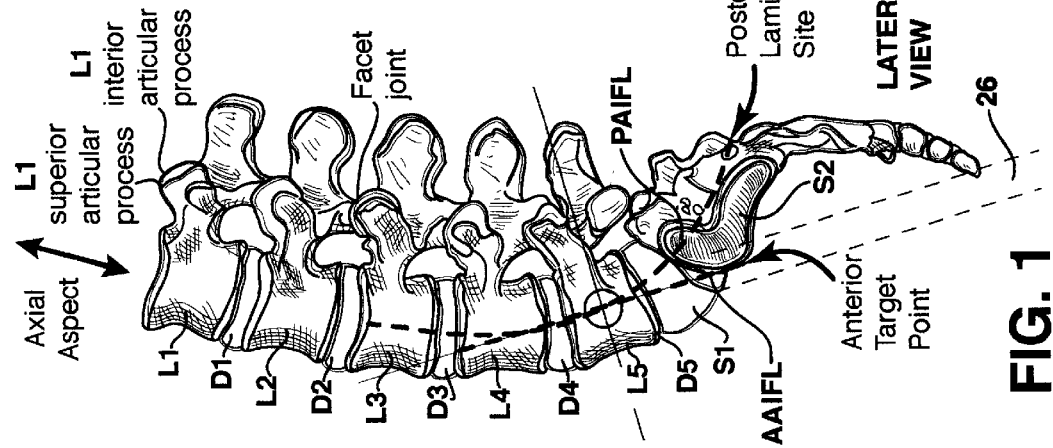

METHOD AND APPARATUS FOR PROVIDING POSTERIOR OR ANTERIOR TRANS-SACRAL ACCESS TO SPINAL VERTEBRAE

This application claims priority and benefits from Provisional Patent Application No. 60/182,748, filed Feb. 16, 2000 entitled METHOD AND APPARATUS FOR TRANS-SACRAL SPINAL FUSION.

FIELD OF THE INVENTION

The present invention relates generally to methods and apparatus for providing percutaneous access to the human sacral and lumbar vertebrae in alignment with a visualized, trans-sacral axial instrumentation/fusion (TASIF) line in a minimally invasive, low trauma, manner.

BACKGROUND OF THE INVENTION

It has been estimated that 70% of adults have had a significant episode of back pain or chronic back pain emanating from a region of the spinal column or backbone. Many people suffering chronic back pain or an injury requiring immediate intervention resort to surgical intervention to alleviate their pain.

The spinal column or back bone encloses the spinal cord and consists of 33 vertebrae superimposed upon one another in a series which provides a flexible supporting column for the trunk and head. The vertebrae cephalad (i.e., toward the head or superior) to the sacral vertebrae are separated by fibrocartilaginous intervertebral discs and are united by articular capsules and by ligaments. The uppermost seven vertebrae are referred to as the cervical vertebrae, and the next lower twelve vertebrae are referred to as the thoracic, or dorsal, vertebrae. The next lower succeeding five vertebrae below the thoracic vertebrae are referred to as the lumbar vertebrae and are designated L1–L5 in descending order. The next lower succeeding five vertebrae below the lumbar vertebrae are referred to as the sacral vertebrae and are numbered S1–S5 in descending order. The final four vertebrae below the sacral vertebrae are referred to as the coccygeal vertebrae. In adults, the five sacral vertebrae fuse to form a single bone referred to as the sacrum, and the four rudimentary coccyx vertebrae fuse to form another bone called the coccyx or commonly the "tail bone". The number of vertebrae is sometimes increased by an additional vertebra in one region, and sometimes one may be absent in another region.

Typical lumbar, thoracic and cervical vertebrae consist of a ventral or vertebral body and a dorsal or neural arch. In the thoracic region, the ventral body bears two costal pits for reception of the head of a rib on each side. The arch which encloses the vertebral foramen is formed of two pedicles and two lamina. A pedicle is the bony process which projects backward or anteriorly from the body of a vertebra connecting with the lamina on each side. The pedicle forms the root of the vertebral arch. The vertebral arch bears seven processes: a dorsal spinous process, two lateral transverse processes, and four articular processes (two superior and two inferior). A deep concavity, inferior vertebral notch, on the inferior border of the arch provides a passageway or spinal canal for the delicate spinal cord and nerves. The successive vertebral foramina surround the spinal cord. Articulating processes of the vertebrae extend posteriorly of the spinal canal.

The bodies of successive lumbar, thoracic and cervical vertebrae articulate with one another and are separated by intervertebral discs formed of fibrous cartilage enclosing a central mass, the nucleus pulposus that provides for cushioning and dampening of compressive forces to the spinal column. The intervertebral discs are anterior to the vertebral canal. The inferior articular processes articulate with the superior articular processes of the next succeeding vertebra in the caudal (i.e., toward the feet or inferior) direction. Several ligaments (supraspinous, interspinous, anterior and posterior longitudinal, and the ligamenta flava) hold the vertebrae in position yet permit a limited degree of movement.

The relatively large vertebral bodies located in the anterior portion of the spine and the intervertebral discs provide the majority of the weight bearing support of the vertebral column. Each vertebral body has relatively strong bone comprising the outside surface of the body and weak bone comprising the center of the vertebral body.

Various types of spinal column disorders are known and include scoliosis (abnormal lateral curvature of the spine), kyphosis (abnormal forward curvature of the spine, usually in the thoracic spine), excess lordosis (abnormal backward curvature of the spine, usually in the lumbar spine), spondylolisthesis (forward displacement of one vertebra over another, usually in the lumbar or cervical spine) and other disorders, such as ruptured or slipped discs, degenerative disc disease, fractured vertebra, and the like. Patients who suffer from such conditions usually experience extreme and debilitating pain and often neurologic deficit in nerve function.

Approximately 95% of spinal surgery involves the lower lumbar vertebrae designated as the fourth lumbar vertebra ("L4"), the fifth lumbar vertebra ("L5"), and the first sacral vertebra ("S1"). Persistent low back pain is attributed primarily to degeneration of the disc connecting L5 and S1. There are two possible mechanisms whereby intervertebral disc lesions can instigate and propagate low back pain. The first theory proposes that the intervertebral disc itself produces pain through trauma or degeneration and becomes the primary source of low back pain. Proponents of this theory advocate removal of the painful disc to relieve the low back pain.

Two extensive procedures are available to remove the disc and fuse the adjacent vertebrae together. One method is to replace the disc with bone plugs by going through the spinal canal on either side of the central nerve bundle. This method requires extensive stripping of the paraspinal musculature. More importantly, there are extensive surgical manipulations within the spinal canal itself. Although the initial proponents of this approach report 90% excellent to good results, subsequent studies have been unable to obtain acceptable outcomes and recommend adding internal fixation to improve fusion rates.

The second procedure is the anterior lumbar fusion which avoids the morbidity of posterior muscle stripping by approaching the spine through the abdomen. Surgeons experienced with this technique also report good to excellent patient results in 90% of cases performed. However, when generally used by practicing surgeons, the procedure was found to have a high failure rate of fusion. Attempts to increase the fusion rate by performing a posterior stabilization procedure have been successful, but the second incision increases the morbidity and decreases the advantages of the technique. Thus, the present surgical techniques available to remove and fuse painful lumbar discs are extensive operative procedures with potentially significant complications.

The other proposed mechanism for the intervertebral disc to cause low back pain concerns its affect on associated supportive tissues. The theory states that disc narrowing leads to stress on all of the intervertebral structures. These include the vertebral bodies, ligamentous supports, and facet joints. Surgeries designed to fuse and stabilize the intervertebral segment can be performed through the posterior approach. This is the original surgical procedure which was used to treat low back pain, and it also entails extensive muscular stripping and bone preparation.

There is no single procedure which is universally accepted to surgically manage low back pain patients. Although damaged discs and vertebral bodies can be identified with sophisticated diagnostic imaging, the surgical procedures are so extensive that clinical outcomes are not consistently satisfactory. Furthermore, patients undergoing presently available fusion surgery experience uncomfortable, prolonged convalescence.

A number of devices and techniques involving implantation of spinal implants to reinforce or replace removed discs and/or anterior portions of vertebral bodies and which mechanically immobilize areas of the spine assisting in the eventual fusion of the treated adjacent vertebrae have also been employed or proposed over the years In order to overcome the disadvantages of purely surgical techniques. Such techniques have been used effectively to treat the above described conditions and to relieve pain suffered by the patient. However, there are still disadvantages to the present fixation implants and surgical implantation techniques. The historical development of such implants is set forth in U.S. Pat. Nos. 5,505,732, 5,514,180, and 5,888,223, for example, all incorporated herein by reference.

One technique for spinal fixation includes the immobilization of the spine by the use of spine rods of many different configurations that run generally parallel to the spine. Typically, the posterior surface of the spine is isolated and bone screws are first fastened to the pedicles of the appropriate vertebrae or to the sacrum and act as anchor points for the spine rods. The bone screws are generally placed two per vertebra, one at each pedicle on either side of the spinous process. Clamp assemblies join the spine rods to the screws. The spine rods are generally bent to achieve the desired curvature of the spinal column. Wires may also be employed to stabilize rods to vertebrae. These techniques are described further in U.S. Pat. No. 5,415,661, for example, incorporated herein by reference.

These types of rod systems can be effective, but require a posterior approach and implanting screws into or clamps to each vertebra over the area to be treated. To stabilize the implanted system sufficiently, one vertebra above and one vertebra below the area to be treated are often used for implanting pedicle screws. Since the pedicles of vertebrae above the second lumbar vertebra (L2) are very small, only small bone screws can be used which sometimes do not give the needed support to stabilize the spine. These rods and screws and clamps or wires are surgically fixed to the spine from a posterior approach, and the procedure is difficult. A large bending moment is applied to such rod assemblies, and because the rods are located outside the spinal column, they depend on the holding power of the associated components which can pull out of or away from the vertebral bone.

In a variation of this technique disclosed in U.S. Pat. Nos. 4,553,273 and 4,636,217 (both described in U.S. Pat. No. 5,735,899 incorporated herein by reference, two of three vertebrae are joined by surgically obtaining access to the interior of the upper and lower vertebral bodies through excision of the middle vertebral body. In the '899 patent, these approaches are referred to as "intraosseous" approaches, although they are more properly referred to as "interosseous" approaches by virtue of the removal of the middle vertebral body. The removal is necessary to enable a lateral insertion of the implant into the space it occupied so that the opposite ends of the implant can be driven upward and downward into the upper and lower vertebral bodies. These approaches are criticized as failing to provide adequate medial-lateral and rotational support in the '899 patent. In the '889 patent, an anterior approach is made, slots are created in the upper and lower vertebrae, and rod ends are fitted into the slots and attached to the remaining vertebral bodies of the upper and lower vertebrae by laterally extending screws.

A wide variety of anterior, extraosseous fixation implants, primarily anterior plate systems, have also been proposed or surgically used. One type of anterior plate system involves a titanium plate with unicortical titanium bone screws that lock to the plate and are placed over the anterior surface of a vertebral body. Another type of anterior plate system involves the use of bicortical screws that do not lock to the plate. The bone screws have to be long enough to bite into both sides of the vertebral body to gain enough strength to obtain the needed stability. These devices are difficult to place due to the length of the screws, and damage occurs when the screws are placed improperly.

A number of disc shaped replacements or artificial disc implants and methods of insertion have been proposed as disclosed, for example, in U.S. Pat. Nos. 5,514,180 and 5,888,223, for example. A further type of disc reinforcement or augmentation implant that has been clinically employed for spinal fusion comprises a hollow cylindrical titanium cage that is externally threaded and is screwed laterally into place in a bore formed in the disc between two adjacent vertebrae. Bone grafts from cadavers or the pelvis or substances that promote bone growth are then packed into the hollow center of the cage to encourage bone growth through the cage pores to achieve fusion of the two adjacent vertebrae. Two such cage implants and the surgical tools employed to place them are disclosed in U.S. Pat. Nos. 5,505,732 and 5,700,291, for example. The cage implants and the associated surgical tools and approaches require precise drilling of a relatively large hole for each such cage laterally between two adjacent vertebral bodies and then threading a cage into each prepared hole. The large hole or holes can compromise the integrity of the vertebral bodies, and if drilled too posteriorly, can injure the spinal cord. The end plates of the vertebral bodies, which comprise very hard bone and help to give the vertebral bodies needed strength, are usually destroyed during the drilling. The cylindrical cage or cages are now harder than the remaining bone of the vertebral bodies, and the vertebral bodies tend to collapse or "telescope," together. The telescoping causes the length of the vertebral column to shorten and can cause damage to the spinal cord and nerves that pass between the two adjacent vertebrae.

Methods and apparatus for accessing the discs and vertebrae by lateral surgical approaches are described in U.S. Pat. No. 5,976,146. The intervening muscle groups or other tissues are spread apart by a cavity forming and securing tool set disclosed in the '146 patent to enable endoscope aided, lateral access to damaged vertebrae and discs and to perform corrective surgical procedures.

R. Johnsson et al. report the results of the use of biodegradable rods to augment posterolateral fusion of L5–S1 or L4–S1 in "Posterolateral lumbar fusion using facet joint fixation with biodegradeable rods: a pilot study" *Eur Spine J* 6:14–48' (1997). In this surgical technique, the posterolateral surfaces of the lumbrosacral spine were exposed, and two canals were bored through facets of the vertebrae to be fused. A rod formed of self-reinforced polyglycolic acid composite material was inserted through each canal, and fixed by absorption of body fluids and expansion therein. While successful fusion of L5–S1 was reported in a number of cases, fusion of L4–S1 was unsuccessful or inadequate, and lateral surgical exposure and stripping of the vertebrae facets was still necessary.

A compilation of the above described surgical techniques and spinal implants and others that have been used clinically is set forth in certain chapters of the book entitled *Lumbosacral and Spinopelvic Fixation,* edited by Joseph Y. Margolies et al. (Lippincott-Raven Publishers, Philadelphia, 1996). Attention is directed particularly to Chapters 1, 2, 16, 18, 38, 42 and 44. In *"Lumbopelvic Fusion"* (Chapter 38 by Prof. Rene P. Louis, MD) techniques for repairing a spondylolisthesis, that is a severe displacement of L5 with respect to S1 and the intervening disc, are described and depicted. An anterior lateral exposure of L5 and S1 is made, a discectomy is performed, and the orientation of L5 to S1 is mechanically corrected using a reduction tool, if the displacement is severe. A fibula graft or metal Judet screw is inserted as a dowel through a bore formed extending caudally through L5 and into S1. Further spacer implants are placed in the space occupied by the extracted disc between L5 and S1. External bridge plates or rods are also optionally installed.

The posterolateral or anterior lateral approach is necessitated to correct the severe spondylolisthesis displacement using the reduction tool and results in tissue injury. Because of this approach and need, the caudal bore and inserted the Judet screw can only traverse L5 and S1.

The above-described spinal implant approaches involve highly invasive surgery that laterally exposes the anterior or posterior portions of the vertebrae to be supported or fused. Extensive muscular stripping and bone preparation can be necessary. As a result, the spinal column can be further weakened and/or result in surgery induced pain syndromes. Thus, presently used surgical fixation and fusion techniques involving the lower lumbar vertebrae suffer from numerous disadvantages. It is preferable to avoid the lateral exposure to correct less severe spondylolisthesis and other spinal injuries or defects affecting the lumbar and sacral vertebrae and discs.

A wide variety of orthopedic implants have also been proposed or clinically employed to stabilize broken bones or secure artificial hip, knee and finger joints. Frequently, rods or joint supports are placed longitudinally within longitudinal bores made in elongated bones, e.g., the femur. A surgical method is disclosed in U.S. Pat. No. 5,514,137 for stabilizing a broken femur or other long bones using an elongated rod and resorbable cement. To accomplish a placement of a rod into any single bone, an end of a bone is exposed and a channel is drilled from the exposed end to the other end. Thereafter, a hollow rod is inserted, and resorbable cement is injected through the hollow rod, so as to provide fixation between the distal end of the rod and the cancellous tissue that surrounds the rod. A cement introducer device can also be used for the injection of cement. A brief reference is made in the '137 patent to the possibility of placing rods in or adjacent to the spine in the same manner, but no particular approach or devices are described.

The present invention has at least one objective of providing a practical and advantageous system, method and tools for accessing the spinal vertebrae to repair or augment damaged vertebrae and discs or to insert spinal implants in various manners that overcome the above described disadvantages of posterior and anterior lateral approaches thereto and minimize surgical trauma to the patient.

SUMMARY OF THE INVENTION

The methods and surgical instrumentation of the present invention provide posterior and anterior trans-sacral access to a series of adjacent vertebrae located within a human lumbar and sacral spine having an anterior aspect, a posterior aspect and an axial aspect, the vertebrae separated by intact or damaged spinal discs. A number of related trans-sacral axial spinal instrumentation/fusion (TASIF) methods and surgical tool sets are provided by various alternative embodiments of the present invention. Certain of the tools are selectively employed to form a percutaneous (i.e., through the skin) pathway from an anterior or posterior skin incision to a respective anterior or posterior position, e.g., a target point of a sacral surface or the cephalad end of a pilot hole bored through the sacrum and one or more lumbar vertebrae. The percutaneous pathway is generally axially aligned with an anterior axial instrumentation/fusion line (AAIFL) or a posterior axial instrumentation/fusion line (PAIFL) extending from the respective anterior or posterior target point through at least one sacral vertebral body and one or more lumbar vertebral body in the cephalad direction and visualized by radiographic or fluoroscopic equipment. The AAIFL and PAIFL follow the curvature of the vertebral bodies, although the AAIFL can be straight or relatively straight, depending on the number of vertebrae that the AAIFL is extended through.

The anterior or posterior percutaneous pathway so formed enables introduction of further tools and instruments for forming an anterior or posterior percutaneous tract extending from the skin incision to the respective anterior or posterior target point of the sacral surface or, in some embodiments, the cephalad end of a pilot hole over which or through which further instruments are introduced. The "anterior, presacral, percutaneous tract" disclosed herein extends through the "presacral space" anterior to the sacrum.

The anterior or posterior percutaneous tract is preferably used to bore one or more respective anterior or posterior TASIF bore in the cephalad direction through one or more lumbar vertebral bodies and intervening discs, if present. A single anterior or posterior TASIF bore is preferably aligned axially with the respective visualized AAIFL or PAIFL, and plural anterior or posterior TASIF bores are preferably aligned in parallel with the respective visualized AAIFL or PAIFL. Introduction of spinal implants and instruments for performing discectomies and/or disc and/or vertebral body augmentation is enabled by the provision of the percutaneous pathway in accordance with the present invention and formation of the anterior or posterior TASIF bore(s).

The posterior percutaneous tract preferably extends from a posterior skin incision into the posterior sacrum to a posterior target point exposed by a laminectomy. This posterior percutaneous tract has a tract axis aligned with the visualized PAIFL to provide working space, exposure of the sacrum, and alignment of the boring tool with the visualized PAIFL. The posterior percutaneous tract can take the form of a lumen of a tract sheath introduced through the percutaneous pathway or a guidewire whereby the guidewire provides a percutaneous tract for over the wire passage extending from the skin incision to the posterior target point and aligned with the visualized PAIFL. Either or both of the tract sheath or guidewire can comprise distal fixation mechanisms that enable fixation to the sacral vertebral surface at the posterior target point for through the sheath or over the wire introduction of boring tools or other instruments. Prior to boring the posterior TASIF bore(s), a pilot hole for each such posterior TASIF bore is optionally bored along or parallel with the visualized PAIFL, and the guidewire distal end is affixed to vertebral bone at the cephalad end of the pilot hole to provide the percutaneous tract for guiding a drill or other instrument to form the posterior TASIF bore or conduct discectomies or disc or vertebral bone augmentation.

Certain of the surgical tools take the form of elongated solid body members extending from proximal to distal ends thereof. Such solid body members may be used in combination with or sequentially with elongated hollow body members. Certain of these solid body and hollow body members can have distal fixation mechanisms for attachment to bone and/or can be angles to be aligned with and bear against sacral bone.

The anterior percutaneous pathway is preferably accomplished employing an elongated guide member that is introduced through the skin incision and advanced against the anterior sacrum through the presacral space until the guide member distal end is located at the anterior target point. The posterior viscera are pushed aside as the guide member is advanced through presacral space and axially aligned with the AAIFL at the anterior target point of the anterior sacral surface.

The guide member may take a variety of forms including a blunt tip rod or a guide assembly of an inner occluder and an outer tubular member fitted together having a tubular member lumen receiving the occluder. The occluder may take the form of a solid body member, e.g., an obdurator, a stylet, a guidewire or the like, and the tubular member may take the form of a needle, a trocar, a catheter or the like. Either or both of the inner occluder and outer tubular member may comprise distal fixation mechanisms that enable fixation to the sacral vertebral surface at the anterior target point and/or at the cephalad end of a pilot hole for each such anterior TASIF bore optionally bored along or parallel with the visualized AAIFL. The occluder can be employed to blunt the tip of the outer tubular member during introduction to the anterior target point, if the outer tubular member comprises a distal tip fixation mechanism that would otherwise prematurely engage the sacral bone. Or the occluder can have a distal tip fixation mechanism and be retracted within the outer tubular member to prevent its premature attachment to sacral bone during introduction to the anterior target point.

In its simplest forms, the anterior, presacral, percutaneous tract can take the form of the lumen of the outer tubular member upon removal of the occluder. The anterior percutaneous pathway can be expanded to form the anterior, presacral, percutaneous tract through the patient's anterior presacral space having a tract axis aligned with the visualized AAIFL to provide working space and exposure of the sacrum. In one embodiment, a guidewire having a distal fixation mechanism (which may comprise the occluder) provides the anterior, presacral, percutaneous tract for over-the-wire passage extending from the skin incision to the target point and aligned with the visualized AAIFL. In further embodiments, the lumen of a further tract sheath introduced through the percutaneous pathway, e.g., over the guidewire or after removal of the guidewire, provides a percutaneous tract for over the wire passage extending from the skin incision to the target point and aligned with the visualized AAIFL. The further tract sheath preferably has a distal tract sheath fixation mechanism and configuration that enables alignment and attachment to the anterior sacral bone at the anterior target point to maintain the tract sheath lumen aligned axially with a the visualized AAIFL.

The tissue surrounding the skin incision and the anterior, presacral, percutaneous pathway through the presacral space may optionally be dilated to form an enlarged diameter presacral, percutaneous tract surrounding a guidewire or tubular member and/or to accommodate the insertion of a tract sheath over the guidewire. Dilation can be accomplished manually or by use of one or more dilator or dilatation balloon catheter or any tubular device fitted over a previously extended tubular member or guidewire.

Additionally, a pilot hole can be bored in axial alignment or parallel with the visualized AAIFL by a boring tool introduced through the outer tubular member lumen for each such anterior TASIF bore bored along or parallel with the visualized AAIFL. The guidewire distal end fixation mechanism is then affixed to vertebral bone at the cephalad end of the pilot hole to provide the percutaneous tract for guiding a drill or other instrument to form the anterior TASIF bore or conduct discectomies or disc or vertebral bone augmentation.

In particular embodiments of the present invention, in the anterior TASIF approach, the junction of S1 and S2 is located through a presacral, percutaneous tract posterior to the rectum and extending from a skin incision adjacent the coccyx. A relatively straight anterior TASIF axial bore into at least L5 can be formed in the vertebral column accessed via the anterior, presacral, percutaneous tract to receive a TASIF implant or interventional tools inserted through the anterior, presacral, percutaneous tract. However, the anterior TASIF axial bore can also be curved to follow the curvature of the vertebrae L4, L3, et seq. in the cephalad direction following a visualized, curved, AAIFL extending therethrough.

In a preferred posterior TASIF approach, the posterior sacrum is exposed, a laminectomy is performed at S2, and the posterior percutaneous tract is formed using one of the above-summarized procedures and percutaneous tract tool sets. A curved axial bore is then made upwardly through S2, S1 and into at least L5 and optionally extended and curved to follow the curvature of the vertebrae L4, L3, et seq. in the cephalad direction. A curved TASIF implant or rod can be inserted into the TASIF axial bore to bridge the vertebrae and the intervening discs, if present.

Thus, the various embodiments of the present invention provide access to anterior and posterior target points of the anterior or posterior sacrum preparatory to forming anterior or posterior TASIF bores that extend in the cephalad direction and can be employed to introduce instruments for treatment of vertebral bodies, intervertebral discs and introduction of axially aligned spinal implants as described in further detail in the above-referenced provisional application No. 60/182,748. In either the posterior or anterior approach, multiple bores may be made side-by-side to receive multiple spinal implants.

The access procedures for forming the anterior or posterior percutaneous tract and the subsequently conducted surgical repair and/or implantation procedures are minimally invasive and requires a short, if any, post-implantation hospitalization and recovery period and reduced discomfort to the patient. The access procedures avoid the muscle stripping required to access the vertebrae and/or discs or removal of strong anterior vertebral body bone and intervening discs attendant to the conventional lateral surgical approaches described above The anterior and posterior TASIF approaches also allow disc surgery or disc augmentation through the TASIF bore or pilot hole of all discs traversed by the TASIF axial bore or pilot hole in a minimally invasive manner. Moreover, these approaches can be employed a minimally invasive manner to perform vertebroblasty of the vertebrae traversed by the TASIF axial bore or pilot hole to augment the vertebral bone in cases of compression fracture of the vertebral bone. Vertebroblasty is procedure for augmentation of collapsed vertebral bodies by pumped in materials, e.g., bone cement. In the past, it has been accomplished through a lateral approach of a needle into a single vertebral body and pumping the cement through the needle lumen. The present invention allows larger diameter access to multiple vertebral bodies through the axial approach.

The present invention further enables use of a number of differing types of TASIF implants or rods that can be inserted into the TASIF axial bore or bores. Such implantable vertebral prostheses align, strengthen, and fuse the adjacent vertebrae particularly in the lumbar region of the spinal column. The elongated, axially extending TASIF implants or rods implanted using the percutaneous tracts formed in accordance with the present invention reinforce the relatively strong anterior vertebral bodies and should prevent potentially damaging telescoping of adjacent vertebrae.

The TASIF spinal implants or rods can be implanted in accordance with the present invention in a less traumatic manner than conventional lateral exposure and placement of conventional vertebral prostheses, and the need to implant screws or extend wires laterally through the vertebral bodies and a rod or rods is eliminated. Unlike conventional spinal rods, the TASIF implants or rods that can be implanted inherently possess a low profile and would usually not be felt by the patient after healing.

Moreover, it is contemplated that the anterior or posterior TASIF pilot hole or axial bore may also be used to receive pain relief stimulation electrodes coupled through leads to implantable pulse generators for providing electrical stimulation of the bone and adjoining nerves for pain relief and/or to stimulate bone growth. Other therapeutic spinal implants can be implanted therein to elute drugs or analgesics or emit radiation for treatment of various diseases or pain syndromes.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIGS. 1–3 are lateral, posterior and anterior views of the lumbar and sacral portion of the spinal column depicting the visualized PAIFL and AAIFL extending cephalad and axially from the posterior laminectomy site and the anterior target point, respectively;

FIG. 4 is a sagittal caudal view of lumbar vertebrae depicting a TASIF spinal implant or rod within a TASIF axial bore formed following the visualized PAIFL or AAIFL of FIGS. 1–3;

FIG. 5 is a sagittal caudal view of lumbar vertebrae depicting a plurality, e.g., 2, TASIF spinal implants or rods within a like plurality of TASIF axial bores formed in parallel with the visualized PAIFL or AAIFL of FIGS. 1–3;

DETAILED DESCRIPTION OF THE PREFERRED EMBODIMENTS OF THE INVENTION

Figure 6:
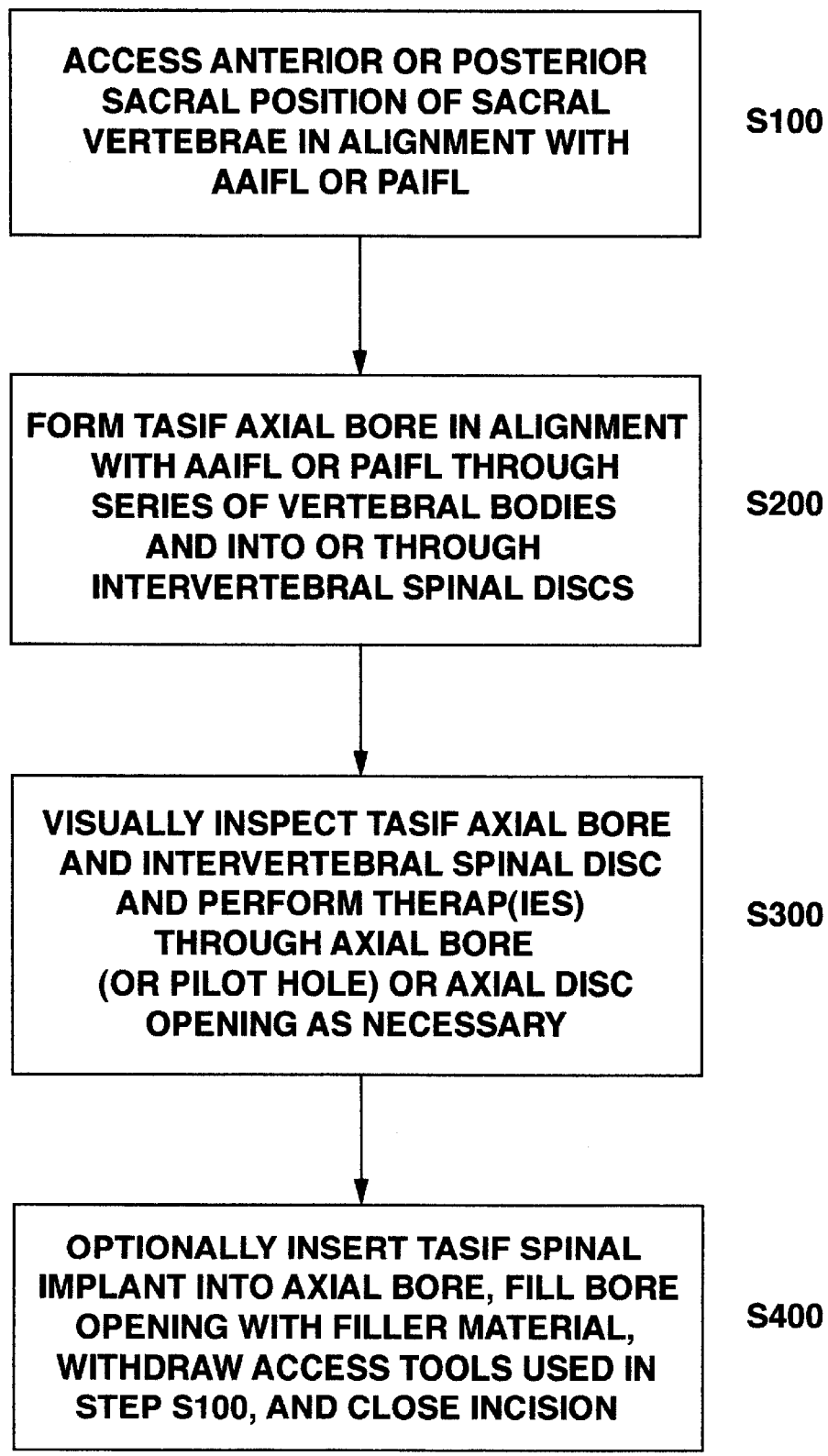
FIG. 6 is a simplified flow chart showing the principal surgical preparation steps of percutaneously accessing a posterior or anterior target point of the sacrum and forming a percutaneous tract following the visualized PAIFL or AAIFL of FIGS. 1–3, as well as subsequent steps of forming the TASIF bore(s) for treatment of accessed vertebral bodies and intervening discs and/or implantation of spinal implants therein.

The preferred embodiments of the invention involve methods and apparatus including surgical tool sets for forming anterior and posterior percutaneous tracts for accessing anterior and posterior target points of the sacrum in alignment with the visualized AAIFL and PAIFL. In certain embodiments, pilot holes may be bored in the cephalad direction through one or more sacral and lumbar vertebral bodies in alignment with the visualized AAIFL and PAIFL and used as part of the anterior and posterior percutaneous tracts.

As noted above and shown in the above-referenced provisional application No. 60/182,748, the pilot holes of the anterior and posterior percutaneous tracts can-be used to introduce instruments to inspect and/or perform therapies upon the vertebral bodies or intervening discs. The posterior or anterior pilot hole may optionally be used as the posterior or anterior TASIF axial bore, respectively, axially aligned with the PAIFL or AAIFL, respectively, to receive spinal implants of various types.

The access to the anterior and posterior target points or pilot holes offered by the anterior and posterior percutaneous tracts can be used to form larger diameter or particularly shaped TASIF bores, which are also referred to as TASIF bores in the above-referenced parent provisional application No. 60/182,748. The enlarged diameter or otherwise shaped TASIF bores can be used to introduce instruments to inspect and/or perform therapies upon the vertebral bodies or intervening discs and/or insert spinal implants as set forth in the above-referenced parent provisional application No. 60/182, 748 and further described herein.

The following description of FIGS. 1–6 is taken from the above-referenced parent provisional application No. 60/182, 748. The acronyms TASF, AAFL, and PAFL are changed to TASIF, AAIFL and PAIFL in this application to explicitly acknowledge that instruments can be introduced for inspection or treatments in addition to the fusion and fixation provided by spinal implants that may be inserted into the axial bores or pilot holes.

FIGS. 1–3 schematically illustrate the anterior and posterior TASIF surgical approaches in relation to the lumbar region of the spinal column, and FIGS. 4–5 illustrate the location of the TASIF implant or pair of TASIF implants within a corresponding TASIF axial bore 22, 152 or pair of TASIF axial bores $22_1$, $152_1$ and $22_2$, $152_2$. Preferred TASIF surgical approaches for providing anterior and posterior trans-sacral access depicted in FIGS. 1–3 and preparing the TASIF axial bores 22, 152 and $22_1$, $152_1/22_2$, $152_2$ shown in FIGS. 4 and 5 are illustrated in further drawings. Preferred trans-sacral surgical access and TASIF pilot hole preparation tools are depicted in further drawings. Various representative embodiments of TASIF implants or rods usable in the TASIF axial bores 22, 152 and $22_1$, $152_1/22_2$, $152_2$ of FIGS. 4–and 5 are depicted in the above-referenced parent provisional application No. 60/182,748. Two TASIF axial bores and spinal implants or rods are shown in FIG. 5 to illustrate that a plurality, that is two or more, of the same may be formed and/or employed in side by side relation parallel with the AAIFL or PAIFL.

The lower regions of the spinal column comprising the coccyx, fused sacral vertebrae S1–S5 forming the sacrum, and the lumbar vertebrae L1–L5 described above are depicted in a lateral view in FIG. 1. The series of adjacent vertebrae located within the human lumbar and sacral spine have an anterior aspect, a posterior aspect and an axial aspect, and the lumbar vertebrae are separated by intact or damaged spinal discs labeled D1–D5 in FIG. 1. FIGS. 2 and 3 depict the posterior and anterior view of the sacrum and coccyx.

In accordance with the present invention, the method and apparatus for fusing at least L4 and L5 and optionally performing a discectomy of D5 and/or D4 involves accessing an anterior sacral position, e.g. an anterior target point at the junction of S1 and S2 depicted in FIGS. 1 and 3, or a posterior sacral position, e.g. a posterior laminectomy site of S2 depicted in FIGS. 1 and 2. One (or more) visualized, imaginary, axial instrumentation/fusion line extends cephalad and axially in the axial aspect through the series of adjacent vertebral bodies to be fused, L4 and L5 in this illustrated example. The visualized AAIFL through L4, D4, L5 and D5 extends relatively straight from the anterior target point along S1 depicted in FIGS. 1 and 3, but may be curved as to follow the curvature of the spinal column in the cephalad direction. The visualized PAIFL extends in the cephalad direction with more pronounced curvature from the posterior laminectomy site of S2 depicted in FIGS. 1 and 2.

It should be noted that the formation of the anterior tract 26 through presacral space under visualization described above is clinically feasible as evidenced by clinical techniques described by J. J. Trambert, MD, in "Percutaneous Interventions in the Presacral Space: CT-guided Precoccygeal Approach-Early Experience (*Radiology* 1999; 213:901–904).

FIG. 6 depicts, in general terms, the surgical steps of accessing the anterior or posterior sacral positions illustrated in FIGS. 1–3 (S100) forming posterior and anterior TASIF axial bores (S200), optionally inspecting the discs and vertebral bodies, performing disc removal, disc augmentation, and vertebral bone reinforcement (S300), and implanting posterior and anterior spinal implants and rods (S400) in a simplified manner. In step S100, access to the anterior or posterior sacral position, that is the anterior target point of FIG. 3 or the posterior laminectomy site of FIG. 2 is obtained, and the anterior or posterior sacral position is penetrated to provide a starting point for each axial bore that is to be created. Then, an axial bore is bored from each point of penetration extending along either the PAIFL or AAIFL cephalad and axially through the vertebral bodies of the series of adjacent vertebrae and any intervening spinal discs (S200). The axial bore may be visually inspected using an endoscope to determine if the procedures of step S300 should be performed. Discoscopy or discectomy or disc augmentation of an intervening disc or discs or vertebroblasty may be performed through the axial bore (S300). Finally, an elongated TASIF spinal implant or rod is inserted into each axial bore to extend cephalad and axially through the vertebral bodies of the series of adjacent vertebrae and any intervening spinal discs (S400). Other types of spinal implants for delivering therapies or alleviating pain as described above may be implanted substitution for step S400.

It should be noted that performing step S100 in the anterior and/or posterior TASIF procedures may involve drilling a pilot hole, smaller in diameter than the TASIF axial bore, that tracks the AAIFL and/or PAIFL in order to complete the formation of the anterior and/or posterior percutaneous tracts. Step S300 may optionally be completed through the AAIFL/PAIFL pilot hole following step S100, rather than following the enlargement of the pilot hole to form the TASIF axial bore in step S200.

Posterior Approach

Figure 7:
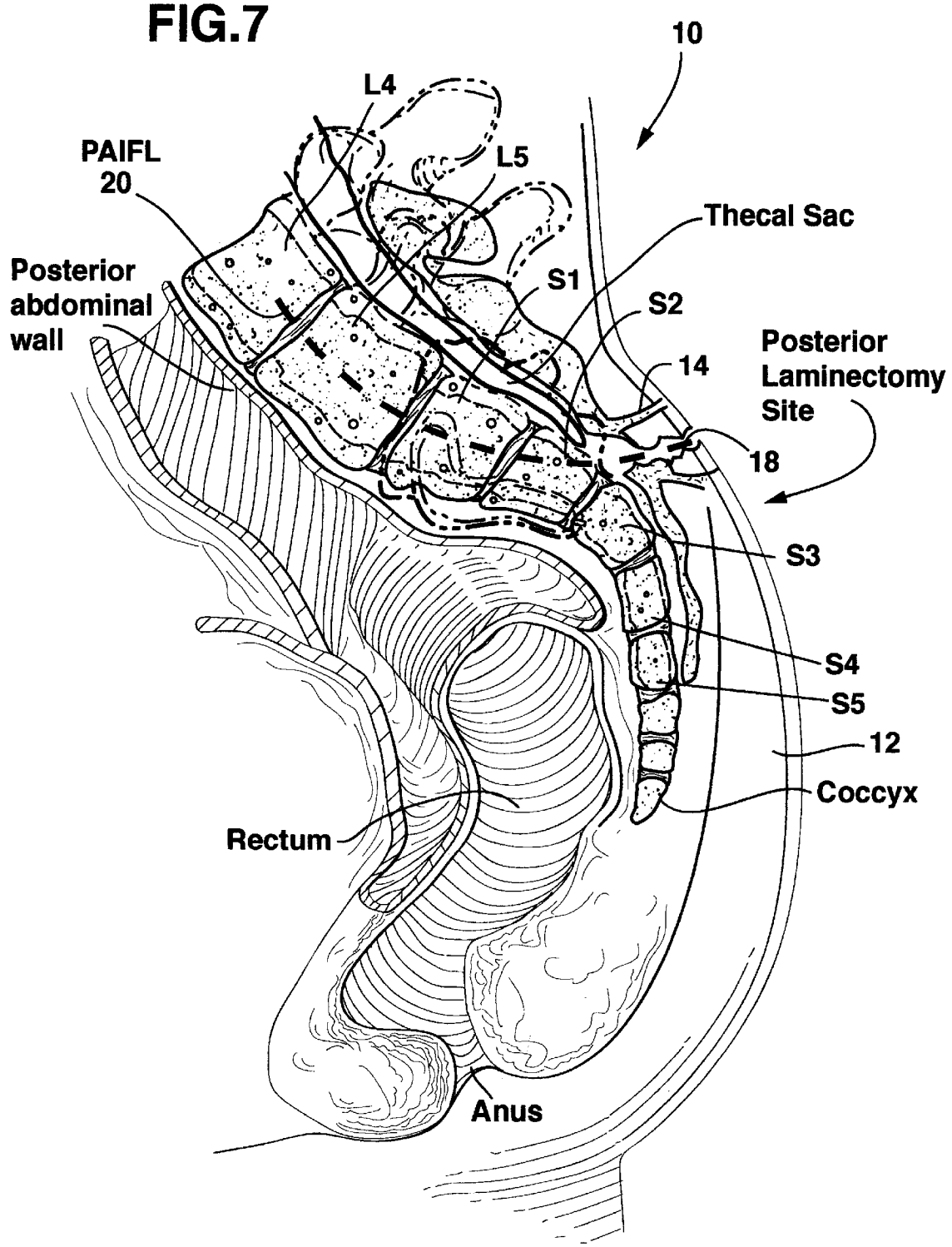
FIGS. 7–9 depict the principal surgical preparation and implantation steps of forming a posterior percutaneous tract enabling access for forming one or more posterior TASIF axial bore following the visualized PAIFL of FIGS. 1 and 2.

Step S100 of FIG. 6 is performed in the posterior TASIF procedure as follows. It is expected that the patient 10, depicted in FIG. 7 in a partial side cross-section view, will lie prone on a surgical table having reverse lordosis support. An imaging system (not shown), which may be an MRI scanner, a CT scanner or preferably a bi-plane fluoroscopy machine, is employed first to show the spinal structure and adjacent tissues, vessels and nerves for visualizing the PAIFL through the visible landmarks of the sacrum and lumbar vertebrae. Then, the imaging system is employed during the surgical creation of the posterior TASIF axial bore to ensure that it remains within the vertebral bodies and intervening discs following the PAIFL and does not stray anteriorly, posteriorly or laterally therefrom.

The area of the patient's skin 12 surrounding the incision site is surgically prepped, and the anus is excluded from the surgical field using adhesive drapes. The actual dermal entry site may be determined by the prone, preoperative CT scan or MRI study that maps the PAIFL. In step S100, depicted in FIG. 7, an incision is made in the patient's skin 12 over the posterior sacral surface of S2 and a posterior tract 18 is formed through the subcutaneous tissue to expose the posteriorly extending, bony ridge of the posterior sacral surface. A small laminectomy 14 is performed through the posterior ridge of the sacrum inferior.

The thecal sac and nerve roots that are exposed by the laminectomy are gently retracted, and the terminal portion of the spinal canal is exposed.

The posterior sacral position or target point is exposed by the laminectomy and through the posterior percutaneous pathway. In accordance with the present invention, a posterior percutaneous tract is provided that enables the precise stabilization and positioning of pilot hole boring and/or posterior TASIF axial bore forming tools for boring the pilot hole and/or posterior TASIF axial bore.

Figure 8:
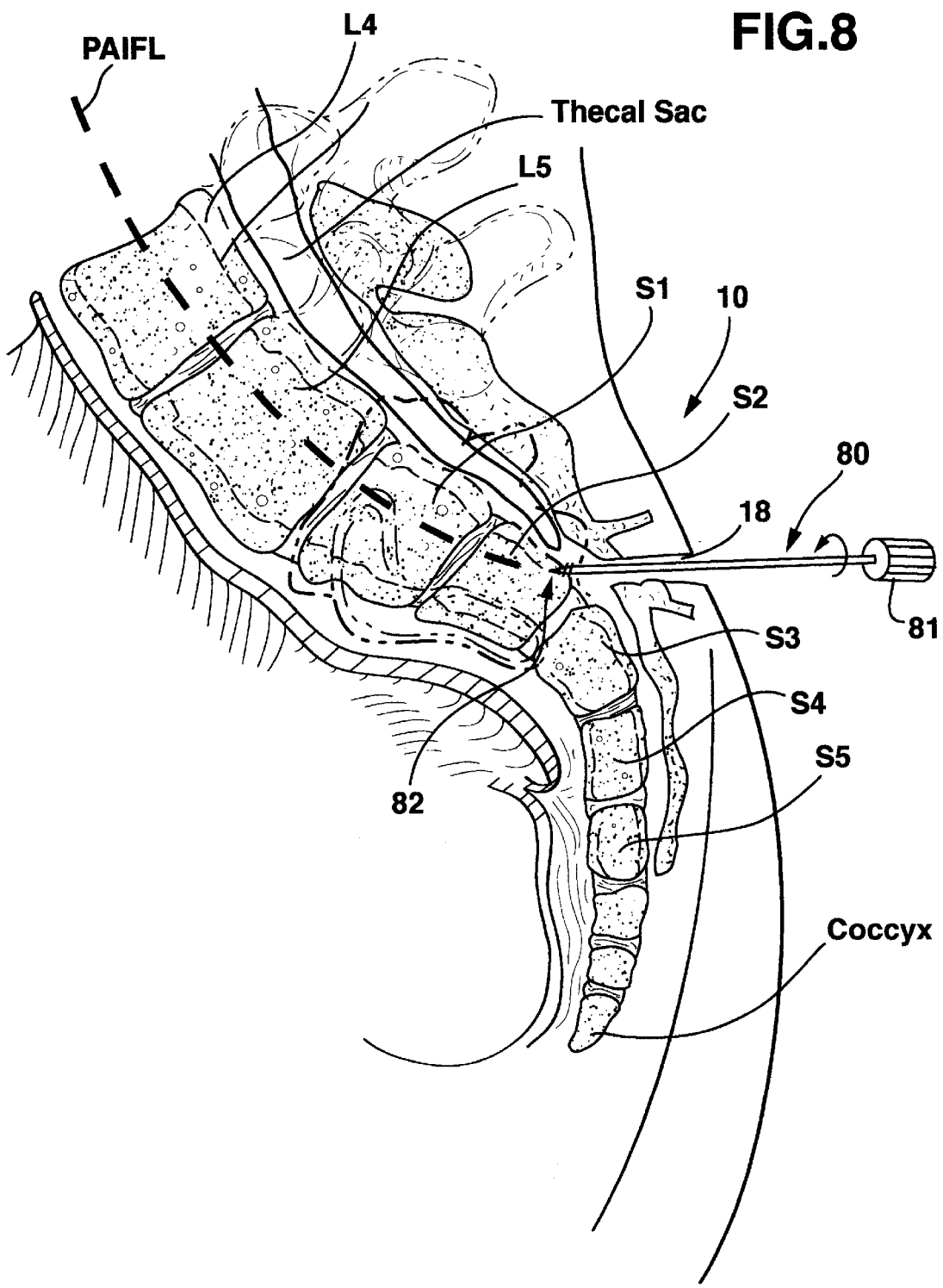

The posterior percutaneous tract can take the form of a guidewire 80 depicted in FIG. 8 that is affixed at its distal end to the sacrum at the posterior target point. The distal fixation mechanism may comprise a distal screw-in tip 82 as shown in FIG. 8 or may take other forms, e.g., the hook or barb 82' depicted in FIGS. 18 and 19. A proximal, removable, guidewire handle 81 is used to rotate the guidewire 80 to screw distal screw-in tip 82 into and out of the sacral bone, and is removed at other times. The guidewire 80 then provides a percutaneous tract extending from the skin incision 18 to the posterior target point that is aligned with the visualized PAIFL The guidewire formed posterior percutaneous tract provides over-the-wire guidance of a drill or boring instrument for boring a pilot hole or posterior TASIF axial bore passage The characteristics and alternative forms that the guidewire 80 may take are described further below in reference to FIG. 13. The guidewire 80 may be introduced through the percutaneous pathway as an occluder within the lumen of an outer, stiffer, tubular member in the manner described below in the anterior approach in reference to FIG. 25. The distal screw-in tip 82 can then be advanced distally, and screwed in while the outer tubular member confines the guidewire shaft. Then the outer tubular member is removed.

Figure 9:
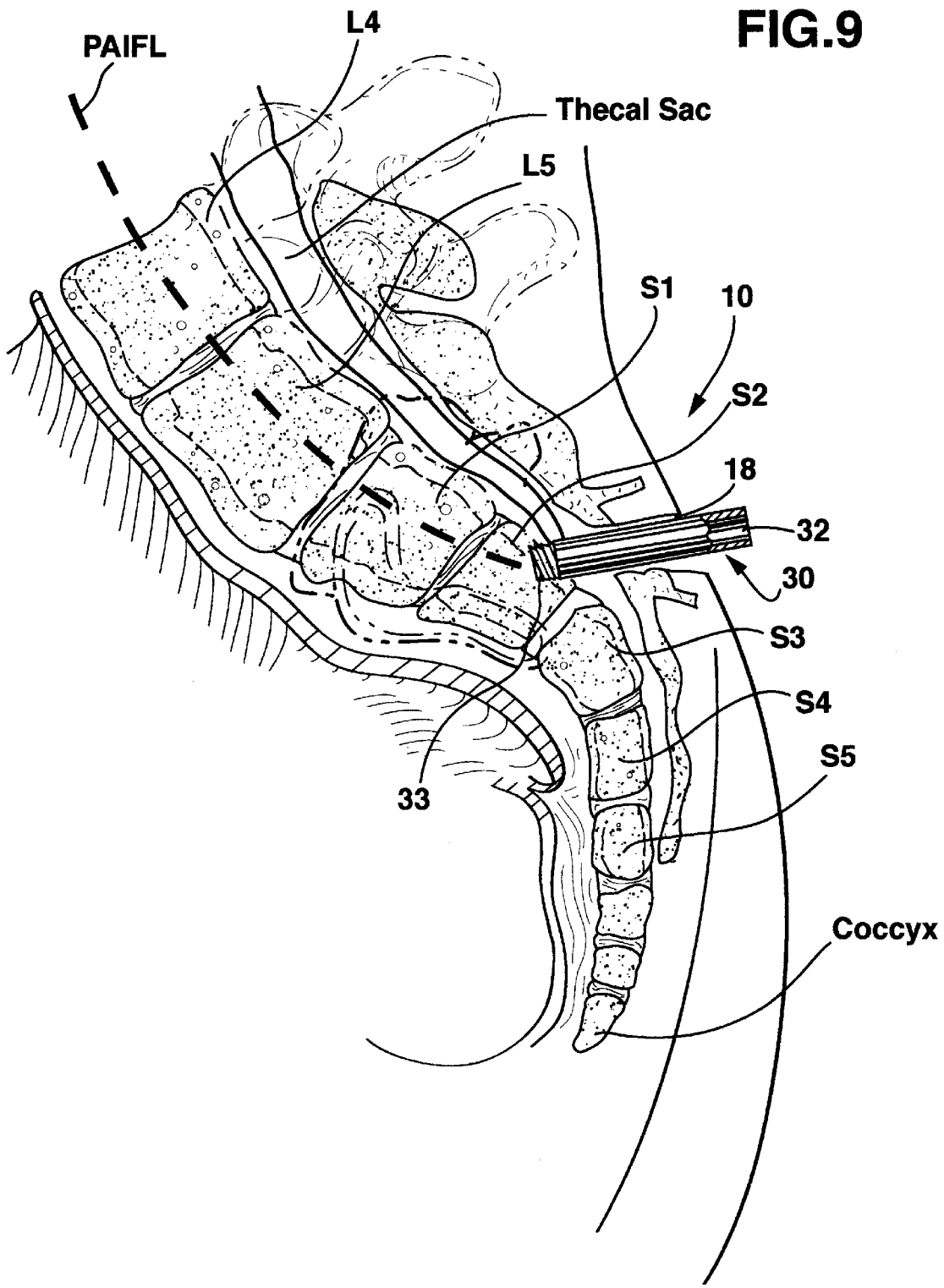

The posterior percutaneous tract can also take the form of a lumen of a posterior tract sheath introduced through the posterior percutaneous pathway. Such a posterior tract sheath 30 is depicted in FIG. 9 having a tract sheath lumen 32 extending from a proximal sheath end 34 to a distal sheath end 36. The distal sheath end 36 is formed with a distal sheath end fixation mechanism for anchoring the distal sheath end 36 to the sacrum at the posterior surface of S2, for example. The depicted distal sheath end fixation mechanism comprises a threaded tip that can be screwed into bone, although a starting hole may have to be first formed so that the screw threads can be advanced and the posterior tract sheath can be firmly fixed to the sacrum.

Figure 10:
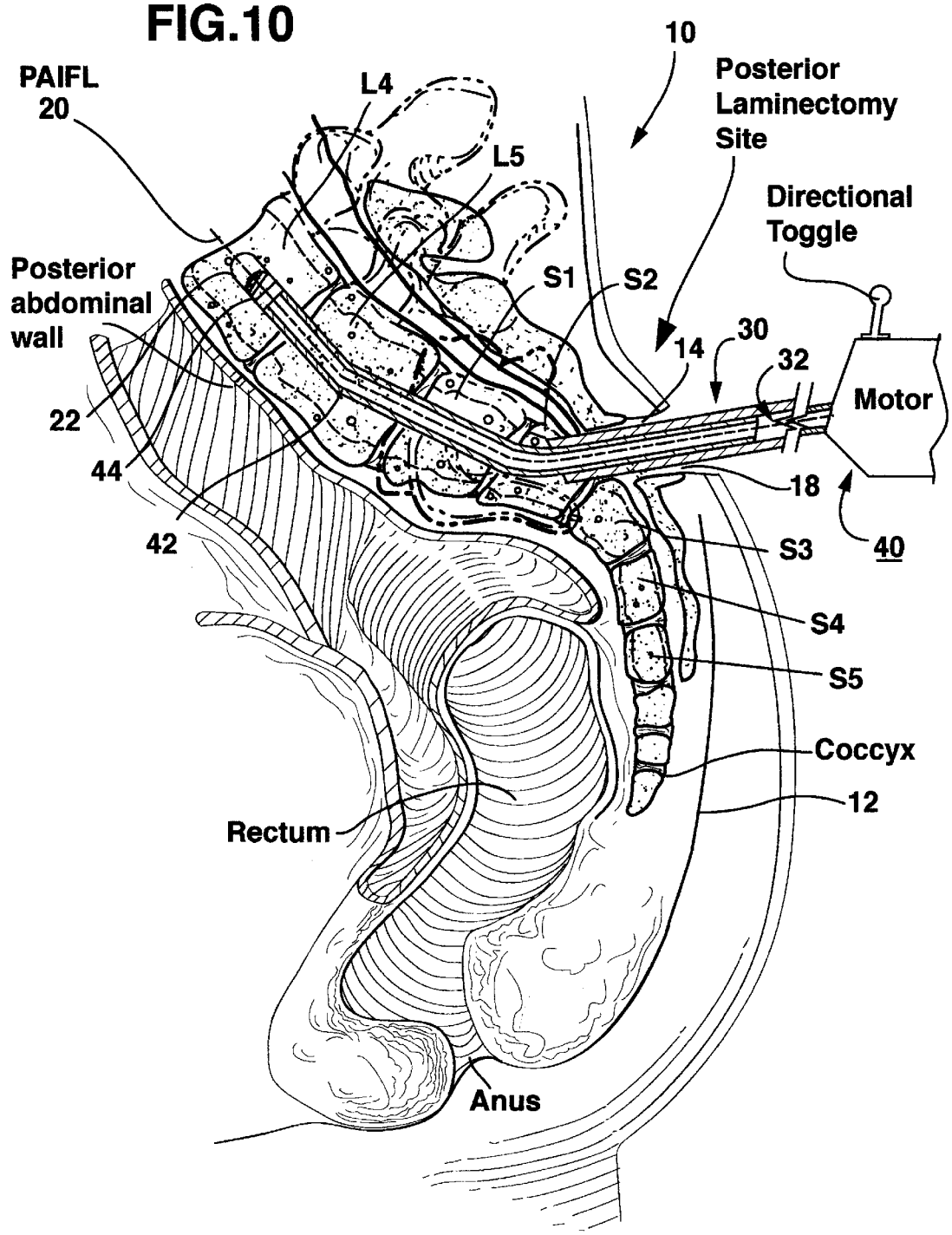
FIGS. 10 and 11 are views of embodiments of a motor driven, canted tip, drill for drilling a posterior pilot hole following the visualized PAIFL of FIGS. 1 and 2.
Figure 11:
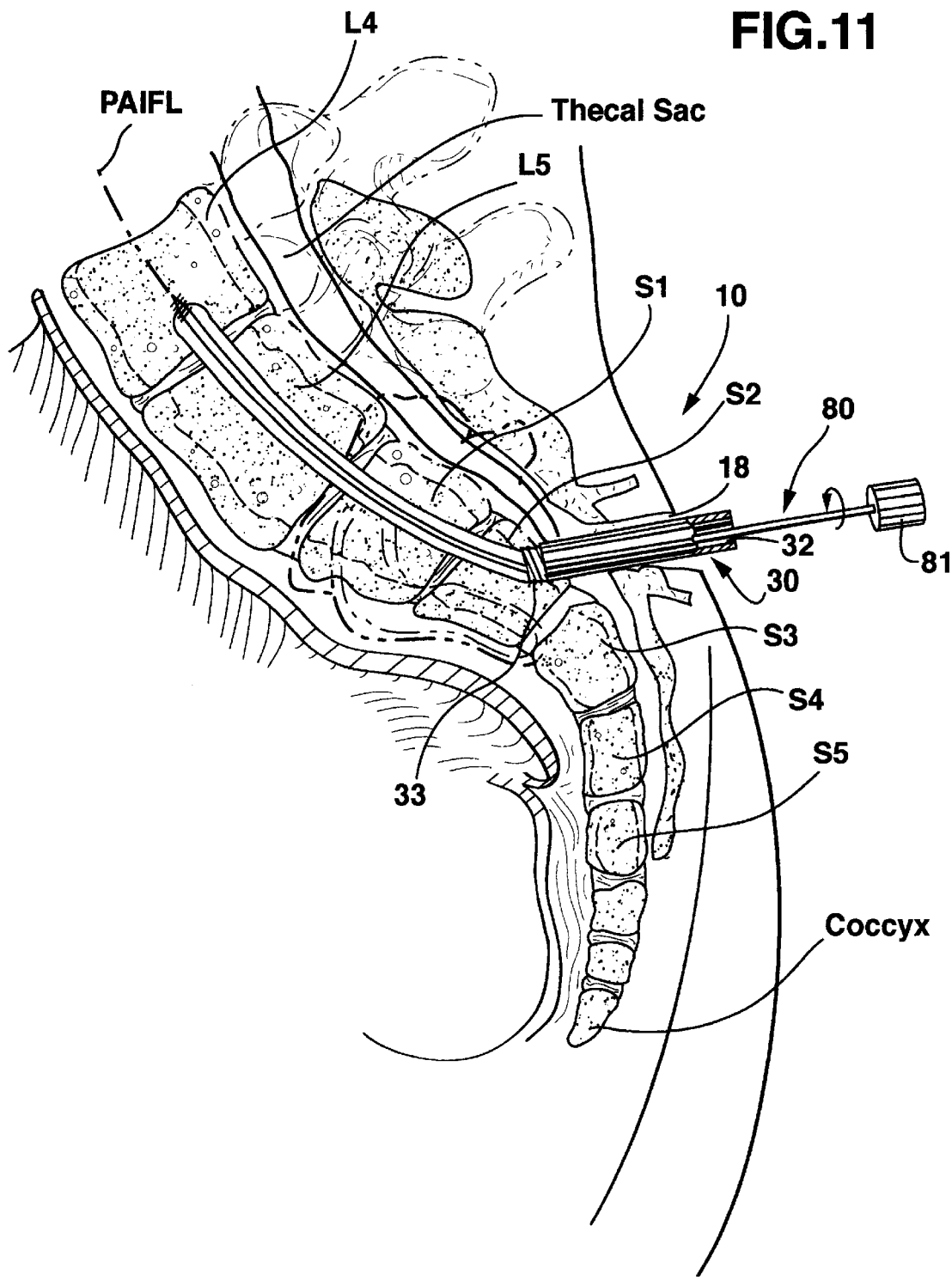

As shown in FIG. 9, the tract sheath lumen 32 provides a posterior percutaneous tract that is axially aligned to starting point of the visualized PAIFL 20, and the tract sheath 30 then functions as a boring tool or drill guide to assist in keeping the boring tool or drill on tract. FIG. 10 depicts the use of the posterior tract sheath 30 with a drill 40 for drilling or boring a posterior pilot hole 38 from the posterior target point at S2 along the visualized PAIFL 20 prior to boring the posterior TASIF bore. This two step approach further involves the insertion of the guidewire through the pilot hole 38 and affixation of the guidewire distal fixation mechanism into the vertebral body bone at the cephalad end of the pilot hole 38 as shown in FIG. 11. The guidewire 80 affixed to the vertebral bone at the cephalad end of the pilot hole provides the posterior percutaneous tract for guiding a drill or other instrument to form an enlarged posterior TASIF bore or for conducting discectomies or disc or vertebral bone augmentation.

Alternatively, the tract sheath 30 may provide the starting point and guide the direct drilling or boring of the posterior TASIF axial bore(s) without forming the pilot hole and employing the guidewire 80 in the manner depicted in FIG. 11.

In FIG. 10, the posterior TASIF pilot hole 38 extends through the centers of two or more vertebral bodies L4, L5 and intervening discs anterior to and extending in parallel with the thecal sac (also shown in FIG. 4, for example). A drill bit 44 at the distal end of a directional drill sheath 42 of a drill 40 or 40' (depicted in FIGS. 10 and 11) is carefully advanced using biplane fluoroscopic visualization (or other visualization) through the sheath lumen 32 operating as a drill guide. The drill drive shaft 46, 46' within the drill sheath 42 is rotated by the drill motor to rotate the drill bit 44, 44' as it is advanced under fluoroscopic observation along the visualized PAIFL 20 and form the curved posterior TASIF pilot hole 38.

Figure 44:
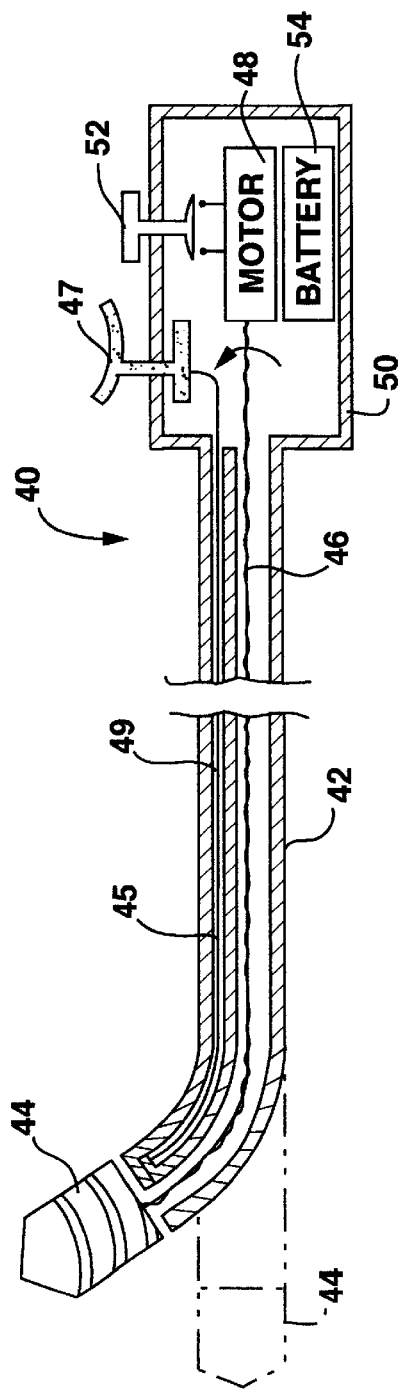
FIG. 44 is a view of one form of pilot hole or TASIF axial bore hole boring tool for forming a pilot hole or TASIF axial bore that is straight or curved in whole or in part.
Figure 45:
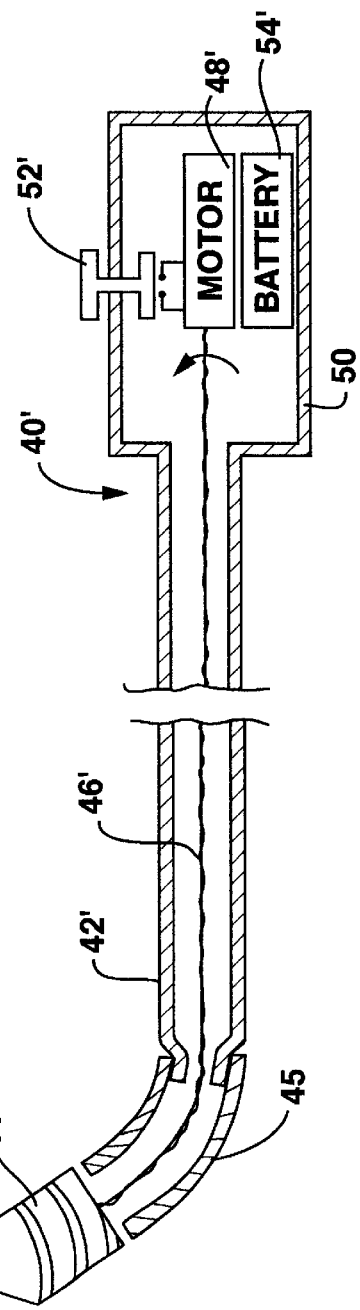
FIG. 45 is a view of another form of pilot hole or TASIF axial bore hole boring tool for forming a pilot hole or TASIF axial bore that is straight or curved in whole or in part.

Suitable exemplary directional drills 40 and 40' are schematically depicted in FIGS. 44 and 45. The drill 40 of FIG. 44 comprises a drill motor housing 50 coupled with drill sheath 42 enclosing the drill drive shaft 46. The drill motor housing 50 includes a motor 48 powered by a battery 54. The drill motor 48 is coupled to the battery 54 by manipulation of a power switch 52 to rotate the drive shaft 46 and drill bit 44 of drill 40.

A pull wire 45 extends through a pull wire lumen 49 extending along one side of the sheath 42 between its distal end and a tip curvature control 47 on drill motor housing 50. The distal end portion of drill sheath 42 is flexible, and retraction of pull wire 45 by manipulation of tip curvature control 47 causes the distal end portion of drill sheath 42 to assume a curvature from the straight configuration as shown in phantom lines in FIG. 44. The surgeon can manipulate tip curvature control 47 to control the curvature of the distal end portion of drill sheath 42 and the TASIF axial bore 22.

The drill 40' of FIG. 45 comprises a drill motor housing 50' coupled with drill sheath 42' enclosing the drill drive shaft 46'. The drill motor housing 50' includes a battery 54' and motor 48' that is turned on by manipulation of a power switch 52' to rotate the drive shaft 46' and drill bit 44' of drill 40'. In this embodiment, the distal end portion 56 of drill sheath 42 is pre-curved or canted at about 20°, for example, providing an eccentric drill bit 44'. The eccentric drill bit 44' has an inherent tendency to "veer" in the direction of rotation of the drill bit. Rotating the drill sheath 42' during advancement along the visualized axial instrumentation/fusion line 20 causes it to form the TASIF pilot hole 38 that follows the curved PAIFL of FIG. 1.

Thus, the drilling of the posterior TASIF axial bore 22 may be undertaken in sequential steps of first drilling a small diameter pilot hole along the PAIFL 20 using the drill 40 or 40', inserting a guidewire through the pilot hole, and then enlarging the pilot hole to form the curved posterior TASIF axial bore. The posterior TASIF axial bore forming tool set may be similar to the anterior TASIF axial bore forming steps and tools described below. Using this technique to form the posterior TASIF axial bore 22, a small diameter drill bit and drill shaft (e.g. 3.0 mm diameter) is used to first drill a small diameter pilot hole 38 following the imaginary, visualized PAIFL 20 through S1, L5 and L4. Then, the drill bit and shaft are removed, and the guidewire 80 having the threaded distal screw-in tip 82 is advanced through the pilot hole 38 and screwed into to the cephalad end of the pilot hole 38 and into the L4 vertebral body. An over-the-wire bore enlarging tool is fitted over the proximal end of the guidewire and manually or mechanically rotated and advanced along it in the manner described below with regard to the formation of the larger diameter, e.g. a 10.0 mm diameter, anterior TASIF axial bore. In this way, the pilot hole diameter is enlarged to form the anterior TASIF axial bore, and the enlarging tool is then removed.

The longitudinal, curved, posterior TASIF axial bore(s) 22 (shown in FIGS. 4 and 5) formed in step S200 of FIG. 6 starts in the sacrum at the posterior target point or position exposed by the laminectomy and extends upwardly or cephalad through the vertebral body of S1 or S2 and through the cephalad vertebral bodies including L5 and L4 and the intervening discs denoted D4 and D5 in FIG. 1. Discs D4 and D5 are usually damaged or have degenerated between lumbar spine vertebrae and cause the pain experienced by patients requiring intervention and fusion of the vertebrae. An inspection of the vertebral bodies and discs along the sides of the TASIF axial bore 22 can be made using an elongated endoscope inserted through the TASIF axial bore or the pilot hole 38 if one is formed. A discectomy or disc augmentation and/or vertebroblasty may be performed pursuant to step S300 of FIG. 6 through the posterior TASIF axial bore 22 or pilot hole 38 and laminectomy site to relieve the patient's symptoms and aid in the fusion achieved by the posterior spinal implant or rod.

Anterior Approach

Figure 12:
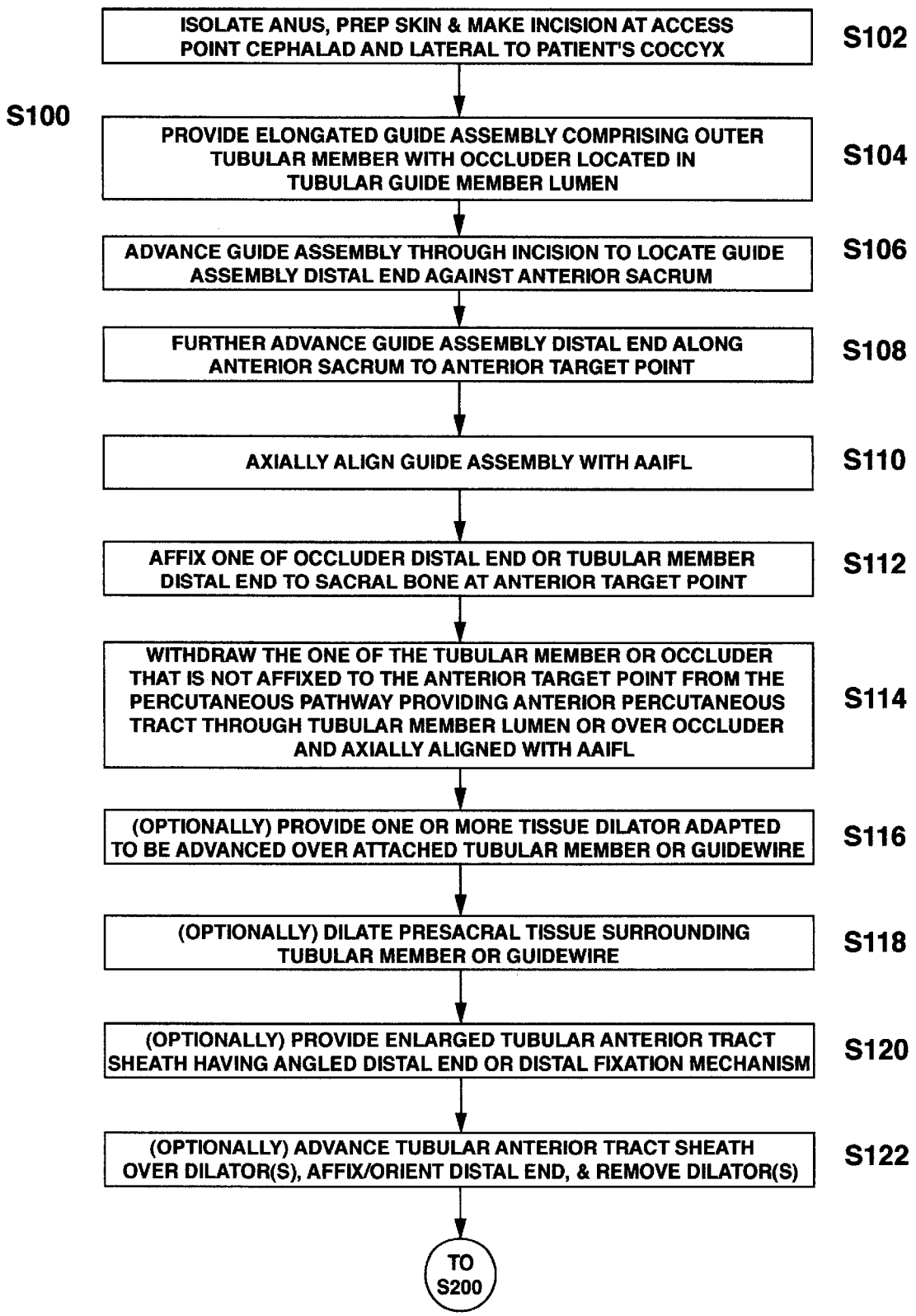
FIG. 12 is a flow chart expanding upon step S100 of FIG. 6 showing the principal surgical preparation steps of forming various types of anterior, presacral, percutaneous tracts axially aligned with the visualized AAIFL of FIGS. 1 and 3 through presacral space posterior to the patient's rectum.
Figure 13:
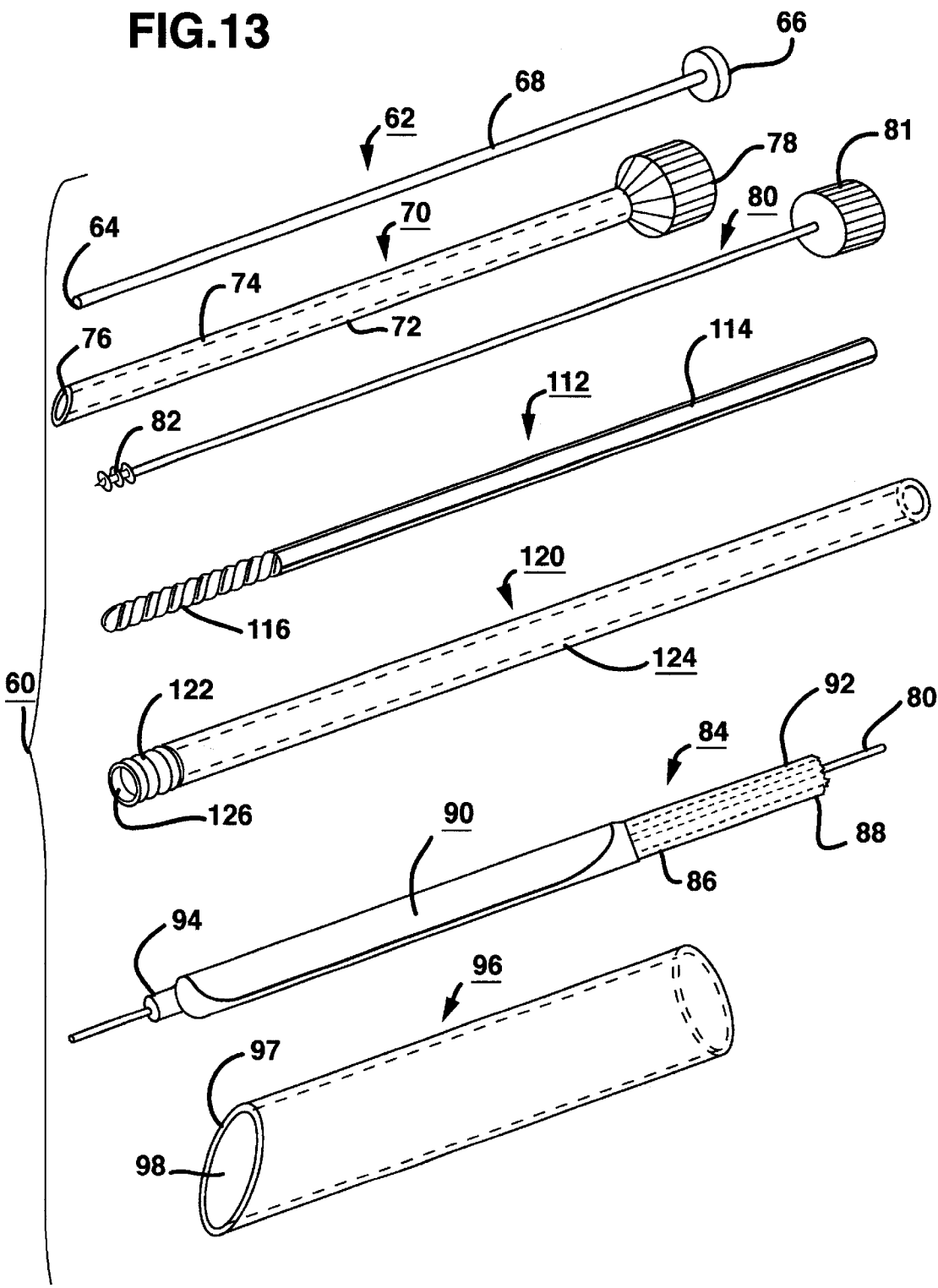
FIGS. 13–21 illustrate various tools employed in various combinations and sequences for forming the various types of anterior, presacral, percutaneous tracts used in performing the anterior tract forming steps set forth in FIG. 12.

Turning to the anterior TASIF approach, FIG. 12 expands upon step S100 of FIG. 6 showing the principal surgical preparation steps of forming an anterior, presacral, percutaneous tract 26 axially aligned with the visualized AAIFL of FIGS. 1 and 3 through presacral space 24 posterior to the patient's rectum. The anterior tract forming steps of FIG. 12 are performed using certain of the tools of an anterior tract forming tool set 60 that is shown in FIG. 13 and optionally using additional or alternative tools illustrated in FIGS. 14–21. Certain additional or alternative surgical procedure steps are set forth in FIGS. 32–34 and 40. The remaining figures illustrate the surgical tools as used in certain of these steps.

Certain of the surgical tools take the form of elongated solid body members extending from proximal to distal ends thereof. Elongated solid body members in medical terminology include relatively stiff or flexible needles of small diameter typically used to penetrate tissue, wire stylets typically used within electrical medical leads or catheters to straighten, stiffen, or impart a curved shape to the catheter, guidewires that are used to traverse body vessel lumens and access remote points therein (certain hollow body guidewires have lumens for a number of uses), and obdurators. Obdurators are typically formed as rods provided in various diameters with blunt distal tips that can be manipulated to penetrate, separate or manipulate tissue without cutting or other damage. In the vernacular of the present invention, the term "guidewre" is employed herein to embrace any such solid body member (guidewire type) that can be employed to perform the functions of over-the-wire delivery and guidance described herein unless the exclusive use of a given one of such solid body members is explicitly stated. Such solid body members may be stiff or flexible and may include distal fixation mechanisms.

Certain others of the surgical tools take the form of hollow body, tubular members having lumens extending from proximal to distal ends thereof. Such hollow body, tubular members can take the form of medical catheters, medical cannulas, medical tubes, hollow needles, trocars, sheaths, and the like. Such hollow body tubular members employed in various embodiments of the present invention may be stiff or flexible and may include distal fixation mechanisms.

In addition, the term "occluder" is employed herein to comprise any form of elongated tool that is inserted into a tubular member lumen and that entirely or partly occludes the lumen of the tubular member and may extend distally from the tubular member distal end. Any of the guidewire types can function as an occluder of the lumen of any of the tubular member types.

The anterior tract tool set 60 depicted in FIG. 13 and variations and modifications thereof shown in FIGS. 14–19 include a number of surgical tools that can be used in combination and over or through one another to form or enlarge the anterior percutaneous tract. The anterior percutaneous tract can be enlarged using one or more of the dilators depicted in FIGS. 20 and 21.

Figure 22:
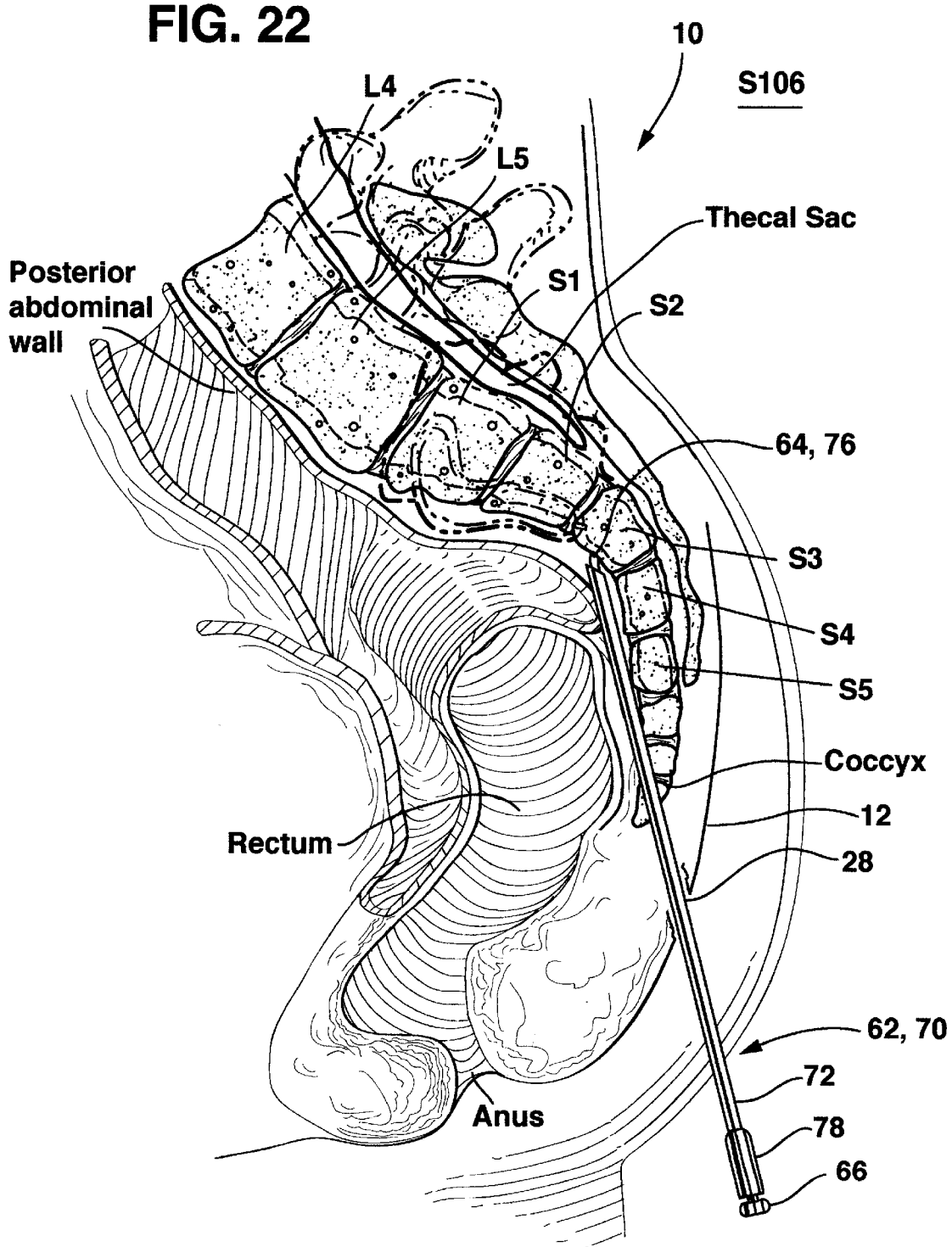
FIGS. 22–26 illustrate the use of certain tools of FIGS. 13–17 following steps of FIG. 12 to form anterior, presacral, percutaneous tracts through the presacral space that are axially aligned with the visualized AAIFL of FIGS. 1 and 3 either surrounding an inner occluder or an outer tubular member of a guide assembly.
Figure 23:
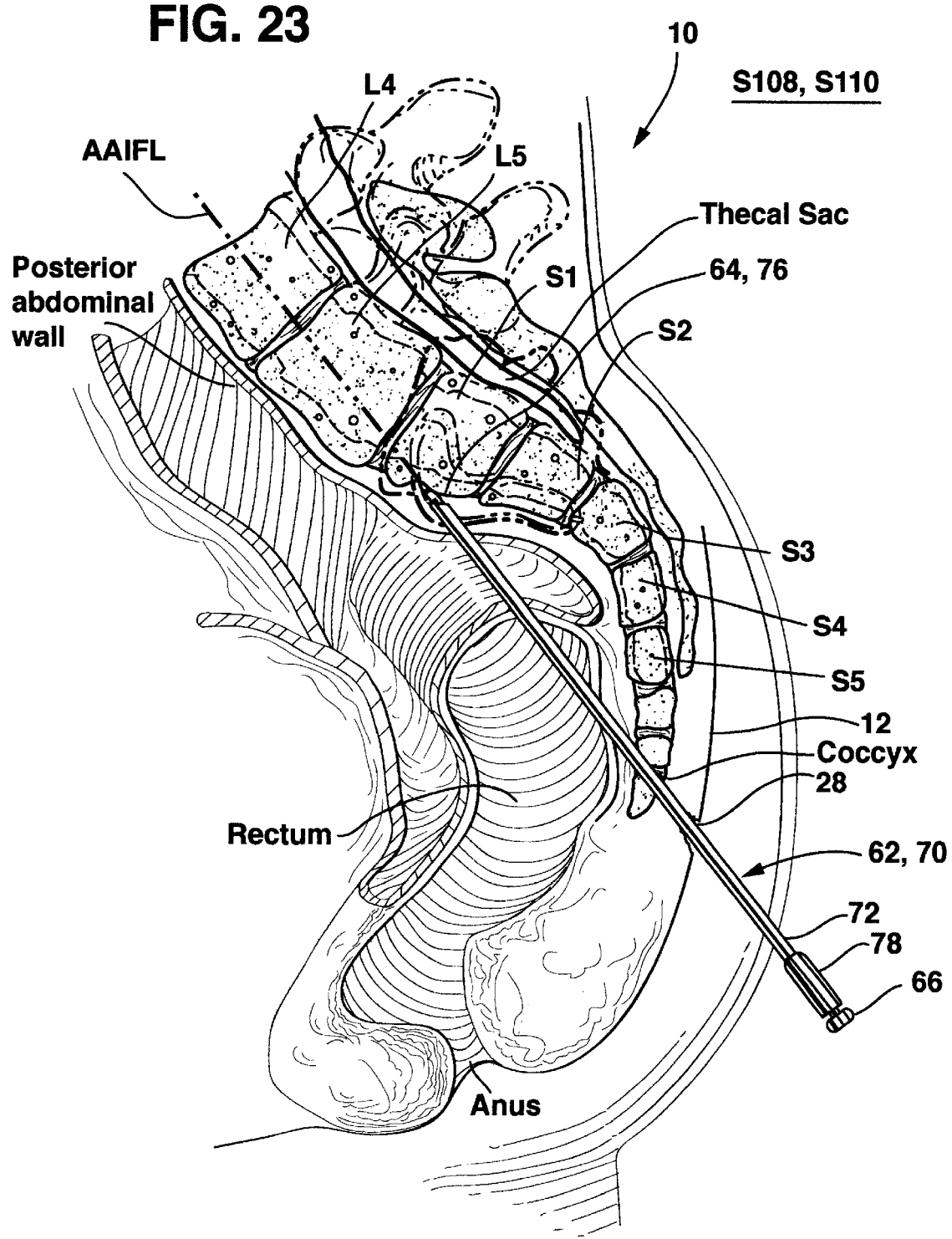

A guide assembly that is employed as shown in FIGS. 22 and 23 is preferably formed of a rounded or blunt tip occluder 62 fitted through the lumen of a percutaneous tubular member 70. A guidewire 80 is also included in tool set 60 that can be inserted through and also function as an occluder of the lumen 74 of percutaneous tubular member 70.

The percutaneous tubular member 70 preferably comprises a 9–18 gauge needle shaft 72 enclosing a needle lumen 74 and extending between a beveled needle distal end 76 and a needle proximal end hub 78. The tubular member lumen 74 is dimensioned in diameter to receive the blunt tip occluder shaft 68 and the guidewire 80. The tubular member shaft 72 is dimensioned in length to allow the distal end blunt tip 64 to protrude from the distal end opening of the tubular member lumen 74 when the occluder proximal end 66 abuts the needle proximal hub 78 as shown in FIGS. 22 and 23. The needle proximal end hub 78 is preferably removable from the needle shaft 72 to enable passage of other tubular members over needle shaft 72.

The guidewire 80 illustrated in FIG. 13 has a threaded screw-in tip 82 having screw threads that are adapted to be screwed into vertebral bone at various steps of the process of forming the anterior tract 26, the TASIF axial bore, and the insertion of an anterior TASIF spinal implant over the guidewire 80 as described below. The guidewire 80 is preferably formed of a kink resistant stainless steel or nickel-titanium alloy wire having an outer diameter of about 0.038 inches to 0.120 inches (about 1.0–3.0 mm) and a length of 100 cm or less. The threaded screw-in tip 82 is formed at the distal end of the guidewire 80, and a removable knob 81 is attached over the proximal end of the guidewire 80. The threaded screw-in tip 82 can be rotated by rotation of the proximal knob 81 in order to screw it into a vertebral body at the anterior target point and at the cephalad end of the anterior TASIF pilot hole as described below. Once the threaded screw-in tip is fixed, the proximal knob 81 can be removed to allow tools and devices to be advanced from its free proximal end over the guidewire body toward the threaded screw-in tip 82 fixed to the bone.

Figure 18:
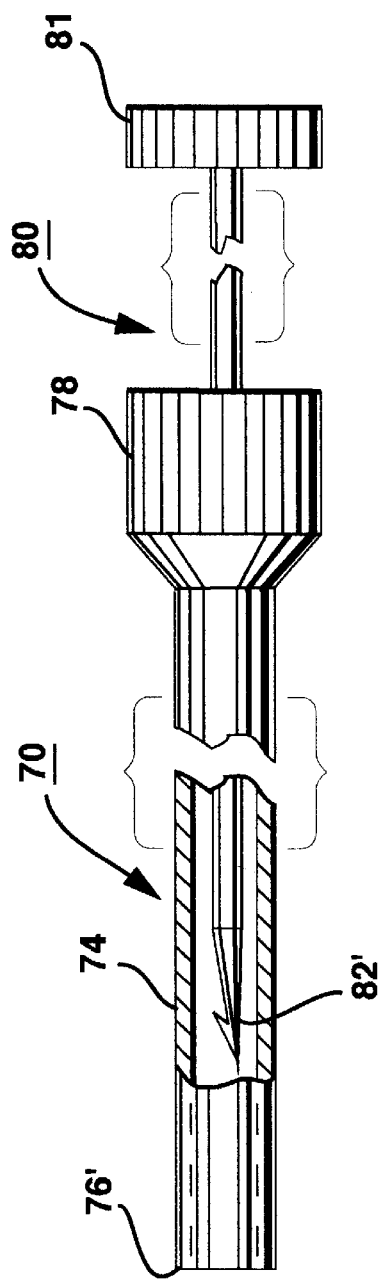
Figure 19:
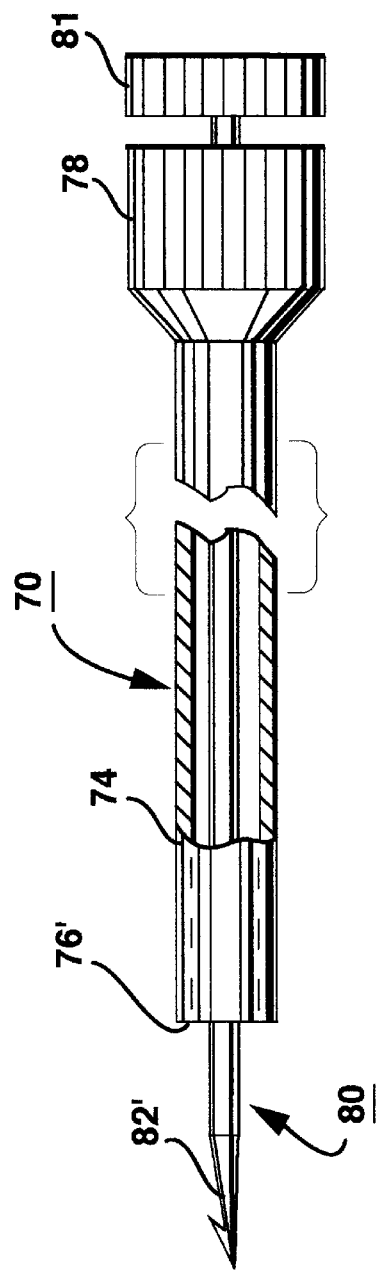

The guidewire distal end fixation mechanism 82 may be configured as a screw-in tip as shown in FIG. 13 or as a hook as shown in FIGS. 18 and 19 or simply of a sharpened tip that can be stabbed into the sacral bone at the anterior target point. If the guidewire 80 is employed as an occluder of the guide assembly, then the guidewire distal end fixation mechanism 82 or 82' is retracted into the lumen tubular member lumen 74 as shown in FIG. 18 and described below in reference to FIG. 33. The distal guidewire fixation mechanism 82 or 82' advanced out as shown in FIG. 19 and attached to the sacral bone when the outer tubular member distal end 76 or 76' is located at the anterior target point of the sacrum.

Figure 14:
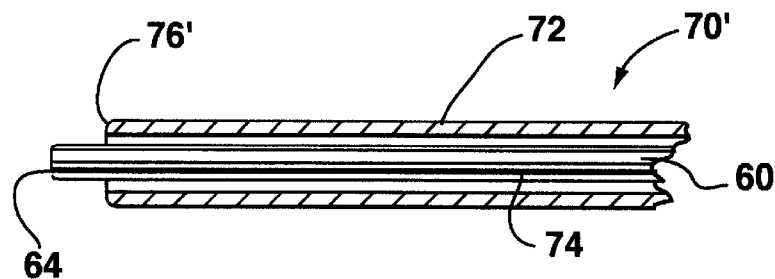
Figure 15:
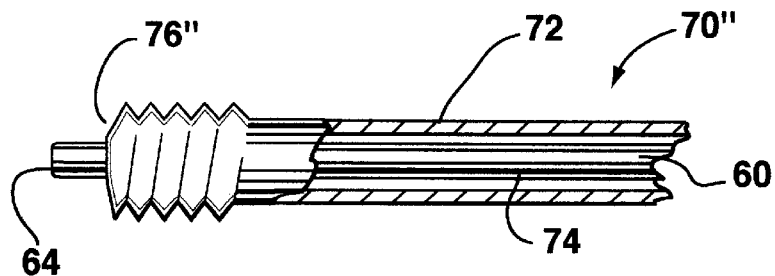
Figure 16:
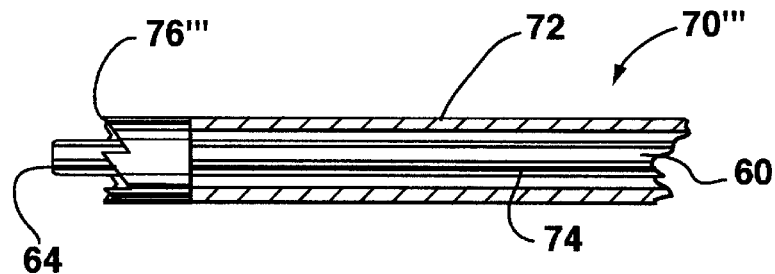
Figure 17:
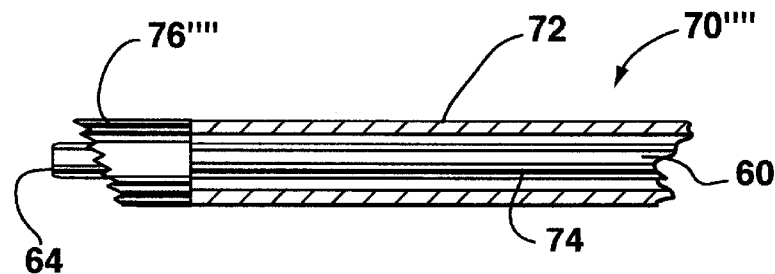

The percutaneous tubular member distal end can be shaped in a variety of ways and can be formed with a 30°–80° angled or beveled tip 76 or a 90° blunt 76' as shown in FIGS. 13, 14, 18, 19, 22, 23 and 25. In the guide assembly depicted in FIGS. 13, 14, 22 and 23, the percutaneous tubular member distal end can itself be sharpened, e.g., by the bevel as shown in FIG. 13, or blunted as shown in FIG. 14. In either case, the percutaneous tubular member lumen is preferably occluded by the blunt tip inner occluder which protrudes distally from the distal end opening of the tubular member 70 FIGS. 14–17 and blunts the percutaneous tubular member distal end enabling it to be advanced along the anterior surface of the sacral bone as described below.

Alternatively, the percutaneous tubular member distal end can be shaped in a variety of ways to incorporate a variety of tubular member distal tip fixation mechanisms as shown in FIGS. 15–17 and 24, for example. The blunt tip obdurator 60 can also be employed to blunt the percutaneous tubular member distal end fixation mechanisms 76', 76" and 76''', for example, enabling the guide assembly distal end to be advanced along the anterior surface of the sacral bone as described below.

One form of the anterior, presacral, percutaneous tract axially aligned with the visualized AAIFL of FIGS. 1 and 3 through presacral space posterior to the patient's rectum comprises the presacral space surrounding the percutaneous tubular member 70 or the guidewire 80 that is introduced as an occluder or after removal of the blunt tip occluder 62 through the percutaneous tubular member lumen in accordance with steps S102–S114 of FIG. 12. FIGS. 22–26 illustrate the exemplary use of certain ones of the tools shown in FIGS. 13–17 and described above following steps of FIG. 12 to form the anterior, presacral, percutaneous tract 26.

The surgical field is prepared as in the posterior TASIF procedure described above. In step S102, an anterior skin incision 28 about 5–10 mm long is made at an access point that is cephalad to the anus and alongside or inferior to the tip of the coccyx to avoid penetrating the rectal wall. For example, the skin incision 28 can be made approximately 2.0 cm lateral and 2.0 cm cephalad to the tip of the coccyx.

In step S104 as illustrated in FIG. 22, the blunt tip occluder 62 is fitted within tubular member lumen 74 to form the guide assembly as shown in FIG. 14, for example. The guide assembly is inserted through the anterior incision 28 and advanced carefully in step S106 under anterior and lateral fluoroscopic imaging visualization posterior to the rectum and through the fatty tissue of the presacral space 24 until the blunt distal end 64 contacts the anterior surface of the sacrum. Then, in step S108 (also shown in FIG. 23), the blunt distal end 64 protruding from the tubular member distal end 76 is advanced or "walked" cephalad along the anterior sacrum under fluoroscopic or CT imaging visualization in the presacral space 24 toward the anterior target point anterior to the body of S2. During this process, care is taken to ensure that the tubular member shaft 72 displaces but does not perforate the rectum and to ensure that nerves and arteries traversing the sacrum and presacral space 24 are not damaged. The rectum can be distended with air so that its posterior wall can be visualized fluoroscopically or other visualization system.

In step S110, after the anterior target point is reached, the guide assembly is axially aligned with the AAIFL. In step S112, either the occluder or the tubular member distal end fixation mechanism is manipulated to affix the occluder or tubular member to the sacrum at the anterior target point. In the embodiment illustrated in FIGS. 22 and 23, the blunt tip occluder 62 is retracted within the tubular member lumen 74, and the tubular member angled distal end 76 is oriented to the angle of the anterior sacrum at the anterior target point as shown in FIG. 25.

Figure 24:
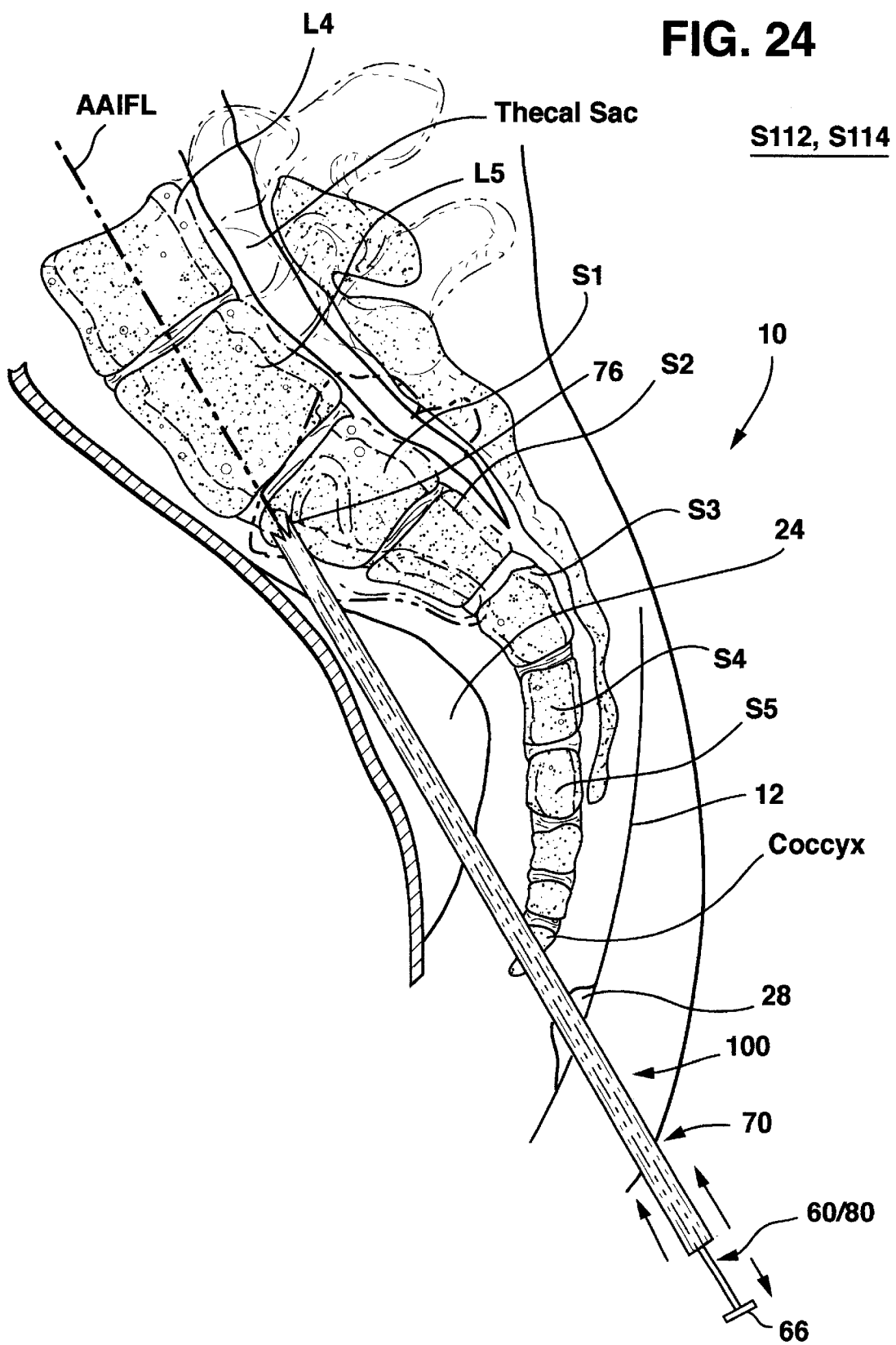

In step S112, if the tubular member distal end comprises a distal end fixation mechanism 76", 76''' or 76'''', then tubular member distal end is advanced to fix the fixation mechanism to sacral bone as shown in FIG. 24. In step S114, the occluder is removed from the tubular member lumen 74, as also shown in FIG. 24. Thus, the percutaneous, presacral, percutaneous tract comprises the presacral space surrounding the tubular member affixed to be axially aligned with the visualized AAIFL so that further tools can be introduced over or alongside the affixed tubular member. The elongated tubular member 70 may be inflexible as a steel needle or flexible as a small diameter catheter but having sufficient column strength to allow torque or axially applied force to be transmitted to its distal end to affix the distal fixation mechanism into sacral bone. In any case, the proximal hub 78 is removable to allow an effective overthe-wire introduction of other tools described further below.

Figure 25:
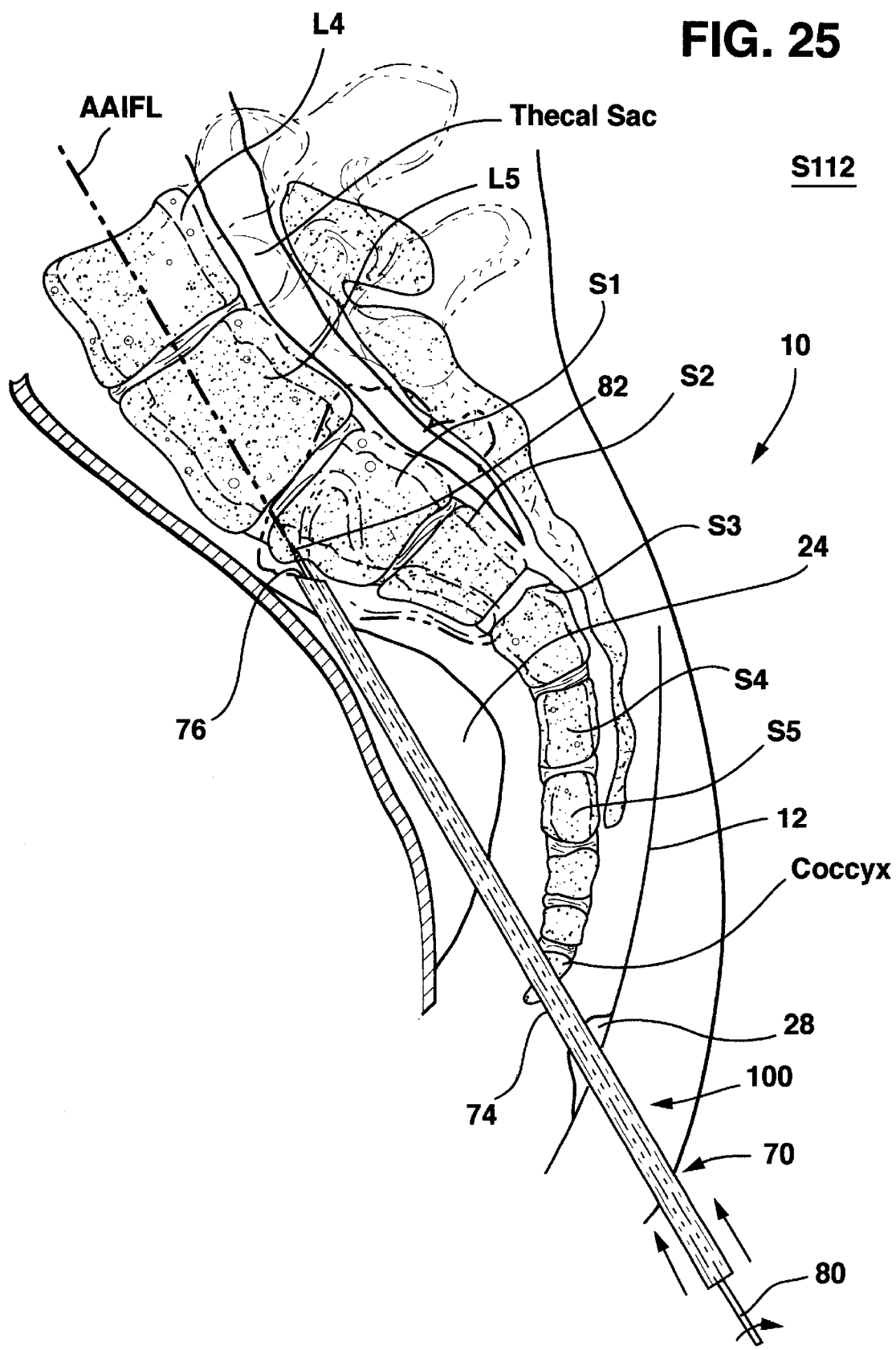
Figure 26:
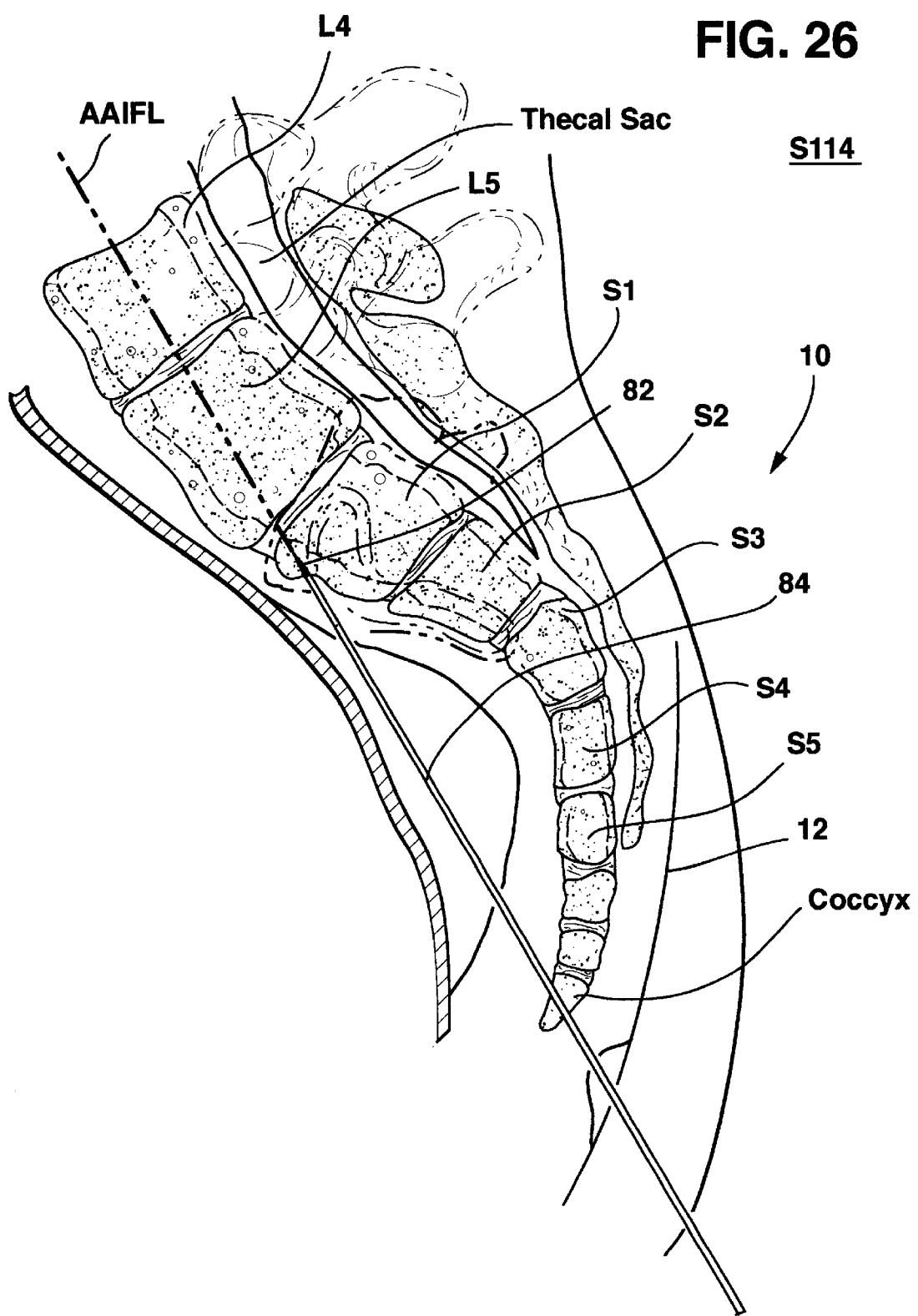
Figure 27:
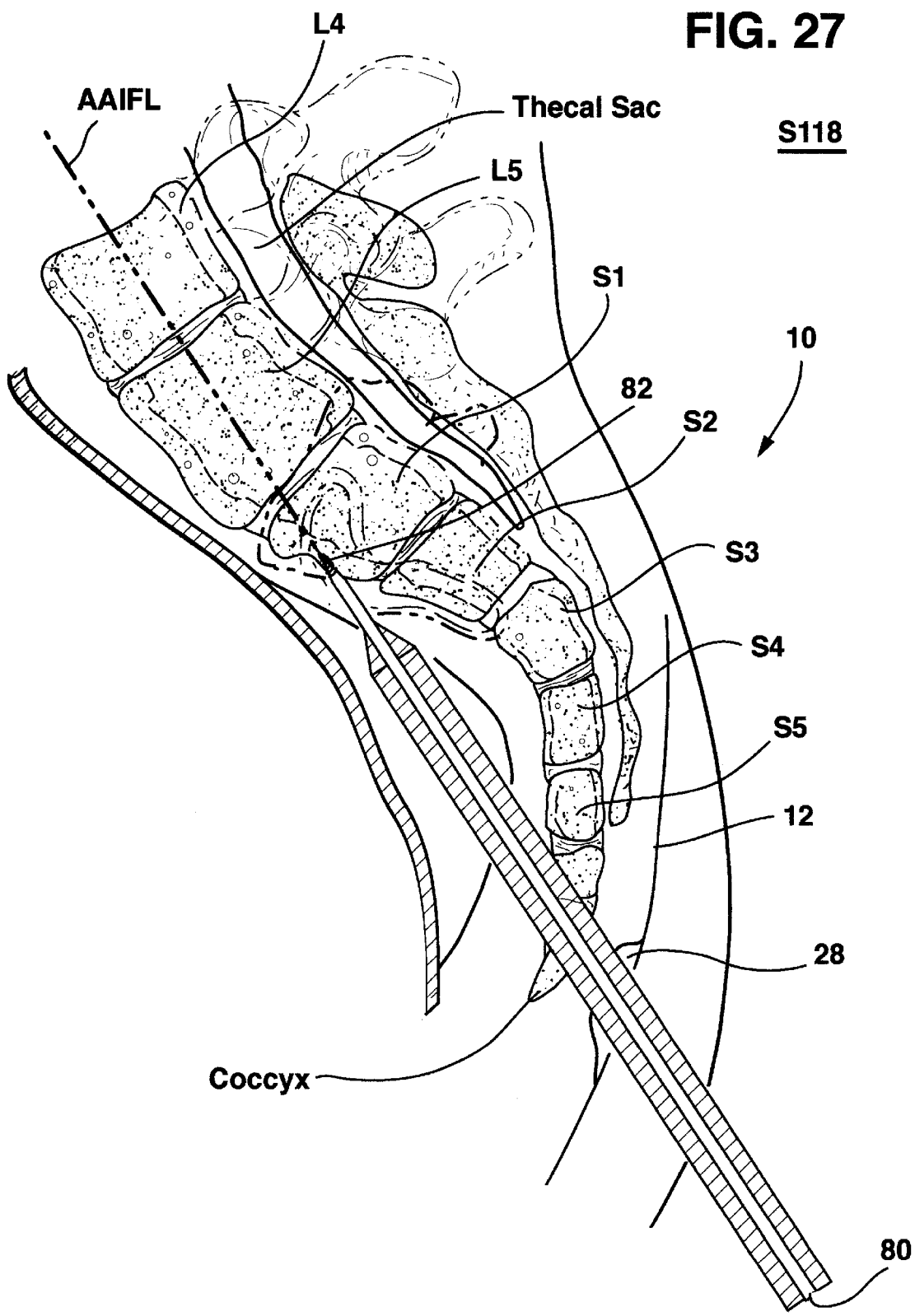
FIG. 27 illustrates the use of one form of dilator(s) shown in FIGS. 20–21 to dilate the presacral space and expand the anterior, presacral, percutaneous tract in accordance with optional steps S116 and S118 of FIG. 12.

Alternatively, when the occluder takes the form of the guidewire 80 or 80' within the tubular member lumen 74 of a blunt tipped tubular member 70, the guidewire distal fixation mechanism 82, 82' is operated in step S112 to fix it to the sacral bone as shown, for example, in FIG. 25, and described above. In the example shown in FIG. 25, the guidewire knob 81 is rotated to screw the distal screw-in tip 82 into the vertebral bone, and the guidewire knob 81 is pulled off the proximal end of the guidewire 80. The tubular member 70 is retracted in step S114, leaving the guidewire 80, 80' axially aligned with the visualized AAIFL as shown in FIG. 26.

Thus, in this embodiment, the percutaneous, presacral, percutaneous tract comprises the presacral space surrounding the guidewire affixed to be axially aligned with the visualized AAIFL so that further tools can be introduced over or alongside the affixed guidewire. The guidewire may be inflexible as a steel needle or typical surgical obdurator or flexible as a small diameter transvenous or arterial or neural guidewire but having sufficient column strength to allow torque or axially applied force to be transmitted to its distal end to affix the distal fixation mechanism into sacral bone.

Then, to the extent necessary, the tissue surrounding the skin incision 28 and the presacral space 24 surrounding the extended guidewire 80 or the tubular member 70 are dilated in step S118 and the rectum is pushed aside without perforating it. A variety of tissue dilators that can be fitted over the extended guidewire 80 or the tubular member 70 are provided in step S116.

One form of tissue dilator comprises a balloon catheter 84 illustrated in FIG. 13. Only the distal portion of the balloon catheter 84 is depicted in FIG. 13, and it comprises a balloon catheter shaft 86 supporting the expandable balloon 90 and enclosing a balloon shaft lumen 88 and a balloon inflation lumen 92. The balloon catheter shaft lumen 88 extends the length of the balloon catheter shaft 86 and terminates at a distal lumen end opening at balloon catheter distal end 94 to allow the guidewire 80 or the tubular member 70 to be received within it. The balloon catheter shaft lumen 88 facilitates advancement of the balloon catheter shaft 86 over the previously placed guidewire 80 or tubular member 70 while the balloon 90 is deflated. The proximal portion of the balloon catheter 84 may take any of the conventional forms comprising a hub for passing the guidewire 80 or tubular member 70 and a side port for providing inflation fluid to and removing fluid from the balloon inflation lumen 92 to inflate and deflate the balloon 90.

Figure 20:
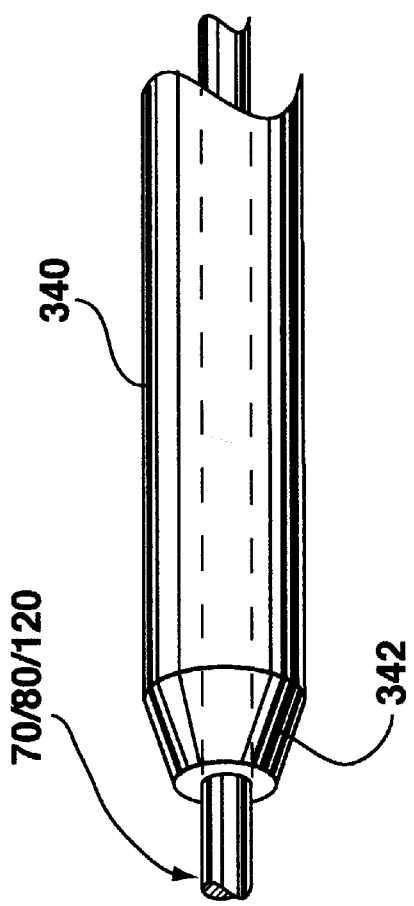
Figure 21:
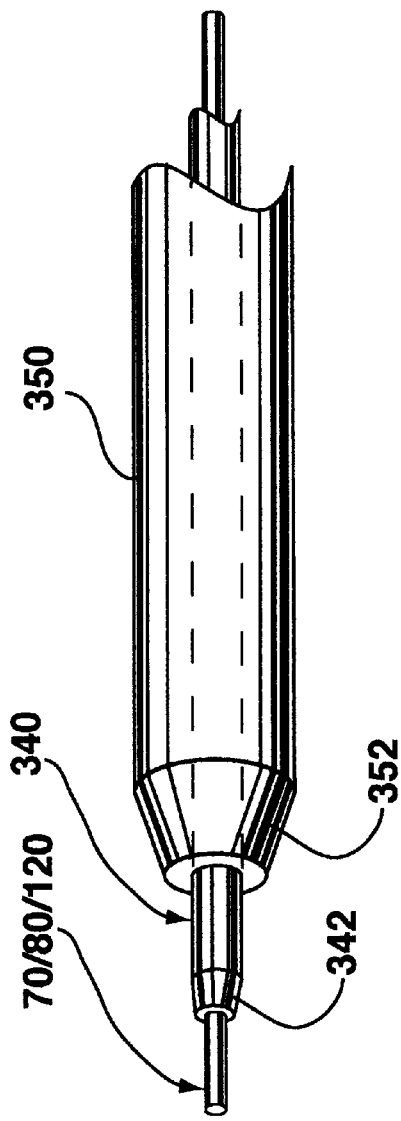

Alternatively, a set of 10 F, 12 F, 14 F, et. seq., tissue dilators 340, 350 shown in FIGS. 20–21 may also be used, to the extent necessary over the guidewire 80 or tubular member 70 (or over a first anterior tract sheath 120 as described below). A single dilator 340 having a gradual taper 342 at the distal end is shown in FIG. 20 to dilate sacral tissue to a first anterior tract diameter. A further dilator 350 having a further taper 352 is shown in FIG. 21 advanced over the first tissue dilator 340 to further expand the anterior tract diameter.

Figure 30:
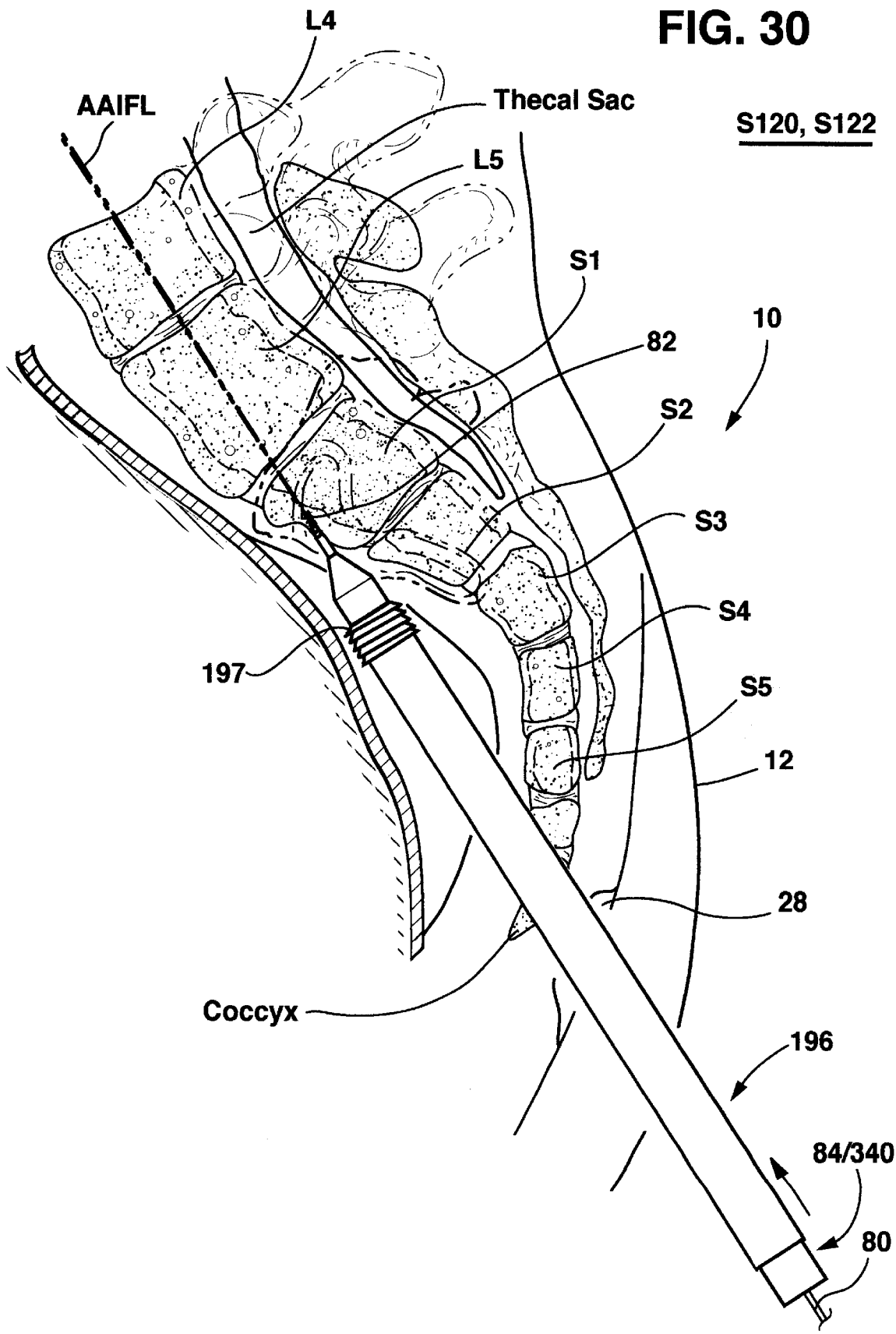
FIG. 30–31 illustrate insertion of an enlarged tubular anterior tract sheath having a distal fixation mechanism through the dilated presacral tissue to form an enlarged anterior, presacral, percutaneous tract comprising the anterior tract sheath lumen in accordance with optional steps S120 and S122 of FIG. 12.
Figure 31:
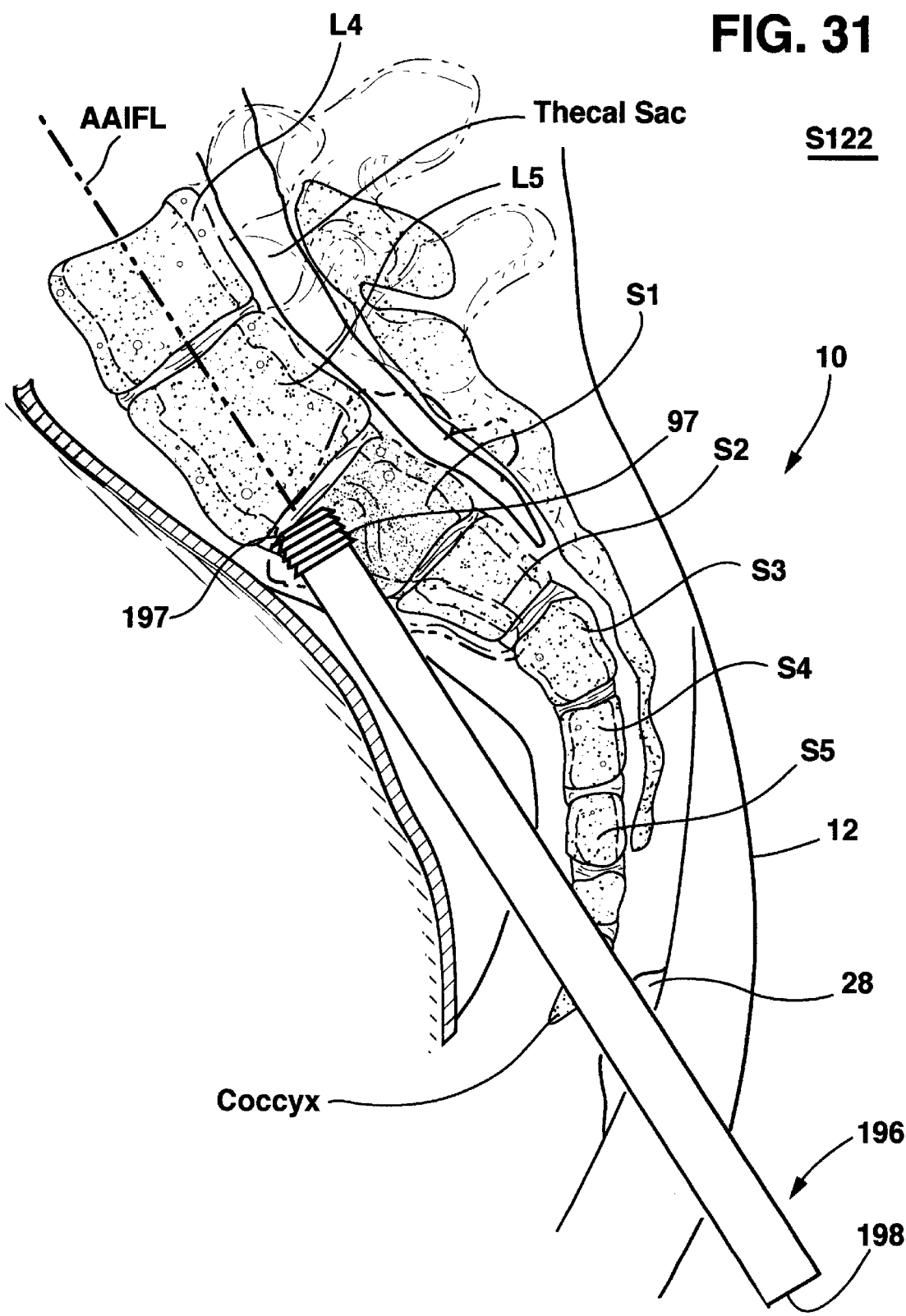

The balloon catheter 84 or the dilator(s) 340, 350 is employed to dilate the presacral tissue and to facilitate the optional insertion of the enlarged diameter anterior tract sheath 96 depicted in FIG. 13 or 196 depicted in FIGS. 30 and 31, in accordance with steps S120 and S122. The enlarged diameter anterior tract sheath 96 is preferably formed of a thin, relatively rigid, metal or plastic tube that is long enough to extend from the skin incision to the anterior target point through the presacral space and. The enlarged diameter anterior tract sheath 96 has an anterior tract sheath lumen 98 and a beveled distal end 97 that is at an angle to the sheath axis. Alternatively, the enlarged diameter anterior tract sheath 196 is formed with an anterior tract sheath distal fixation mechanism 197 of the types employed in the variations of the tubular member 70 described above. A distal threaded tip fixation mechanism 197 is illustrated in FIGS. 30 and 31. Preferably, the diameter of the anterior tract sheath lumen 98, 198 is about 15 mm or 36 F, and tract sheath 96, 196 is about 20 cm long.

The balloon catheter dilator or the dilators 340, 350 are used over the guidewire or over the tubular member of the guide assembly to center the enlarged diameter anterior tract sheath 96 or 196 and to ease introduction of the enlarged diameter anterior tract sheath 96 or 196 past the posterior abdominal wall.

Figure 28:
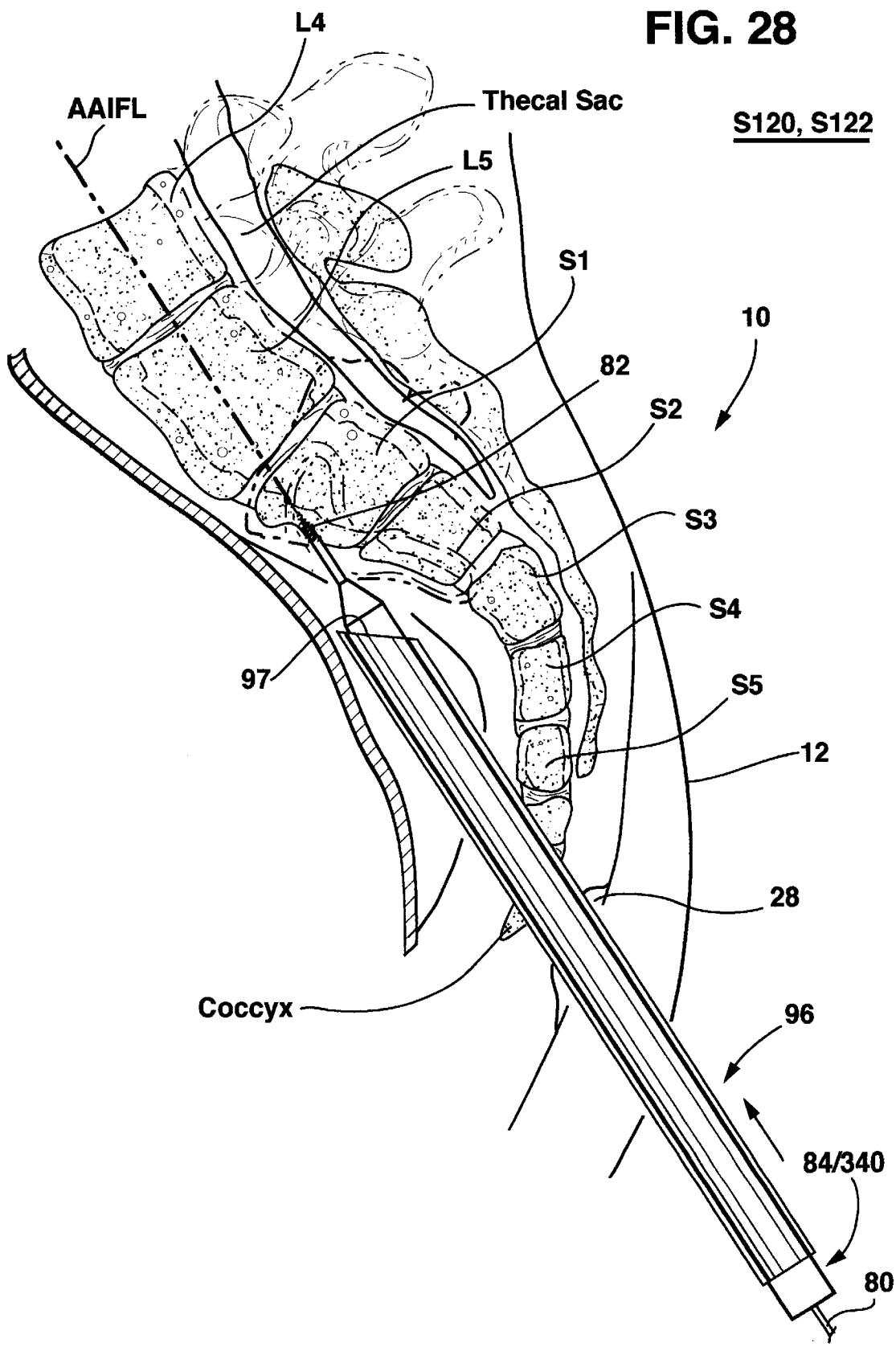
FIG. 28–29 illustrate insertion of an enlarged tubular anterior tract sheath illustrated in FIG. 13 having an angled distal end through the dilated presacral tissue to form an enlarged anterior, presacral, percutaneous tract comprising the anterior tract sheath lumen in accordance with optional steps S120 and S122 of FIG. 12.
Figure 29:
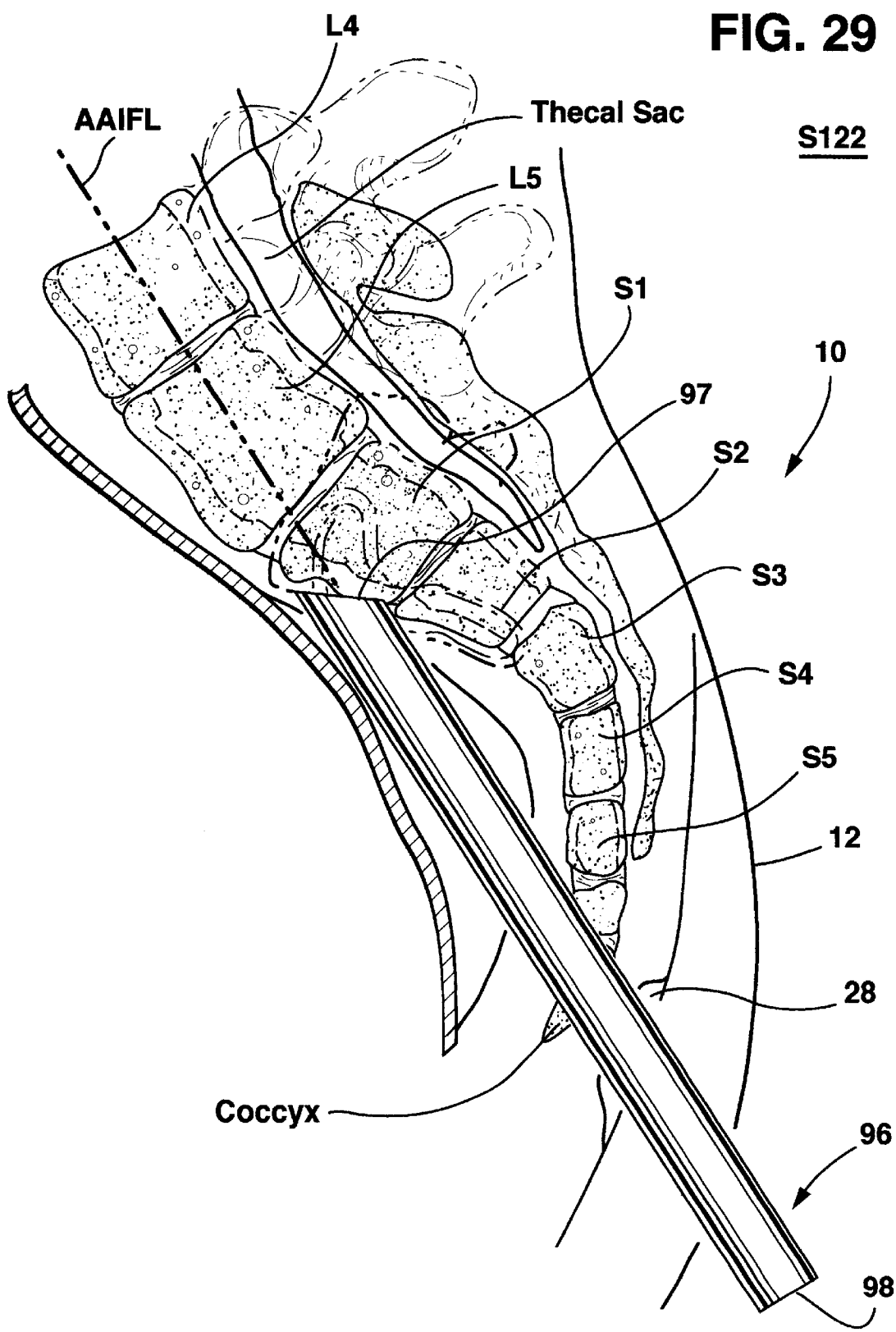

In use of the first embodiment, the enlarged diameter anterior tract sheath 96 is advanced through the presacral space 24 over the inflated balloon 90 or the dilator(s) 340, 350, and the beveled distal end 97 is aligned with the typical angle of the anterior surface of the sacrum at the anterior target point as shown in FIG. 28. The anterior tract sheath 96 is thereby axially aligned with the AAIFL, and the anterior tract sheath lumen 98 forms the anterior tract 26 shown in FIG. 1.

In use of the second embodiment, the anterior tract sheath 196 is advanced through the presacral space 24 over the inflated balloon 90 or the dilator(s) 340, 350 as shown in FIG. 30, and the threaded tip distal end 197 is screwed into the sacral bone at the anterior target point as shown in FIG. 31. The anterior tract sheath 196 is thereby axially aligned with the AAIFL, and the anterior tract sheath lumen 198 forms the anterior tract 26 shown in FIG. 1.

The balloon 90 is then deflated, and the balloon catheter 84 and the guidewire 80 are withdrawn from tract sheath lumen 98, 198. Alternatively, the dilator(s) 340, 350 and the guidewire 80 are withdrawn from tract sheath lumen 98. The anterior tract 26 of the anterior tract sheath 96, 196 is employed in the steps of FIG. 6 in forming the anterior TASIF axial bore (step S200), the performance of the optional discectomy or disc augmentation (step S300), and in the implantation of the TASIF spinal implant in each such bore (step S400).

Figure 32:
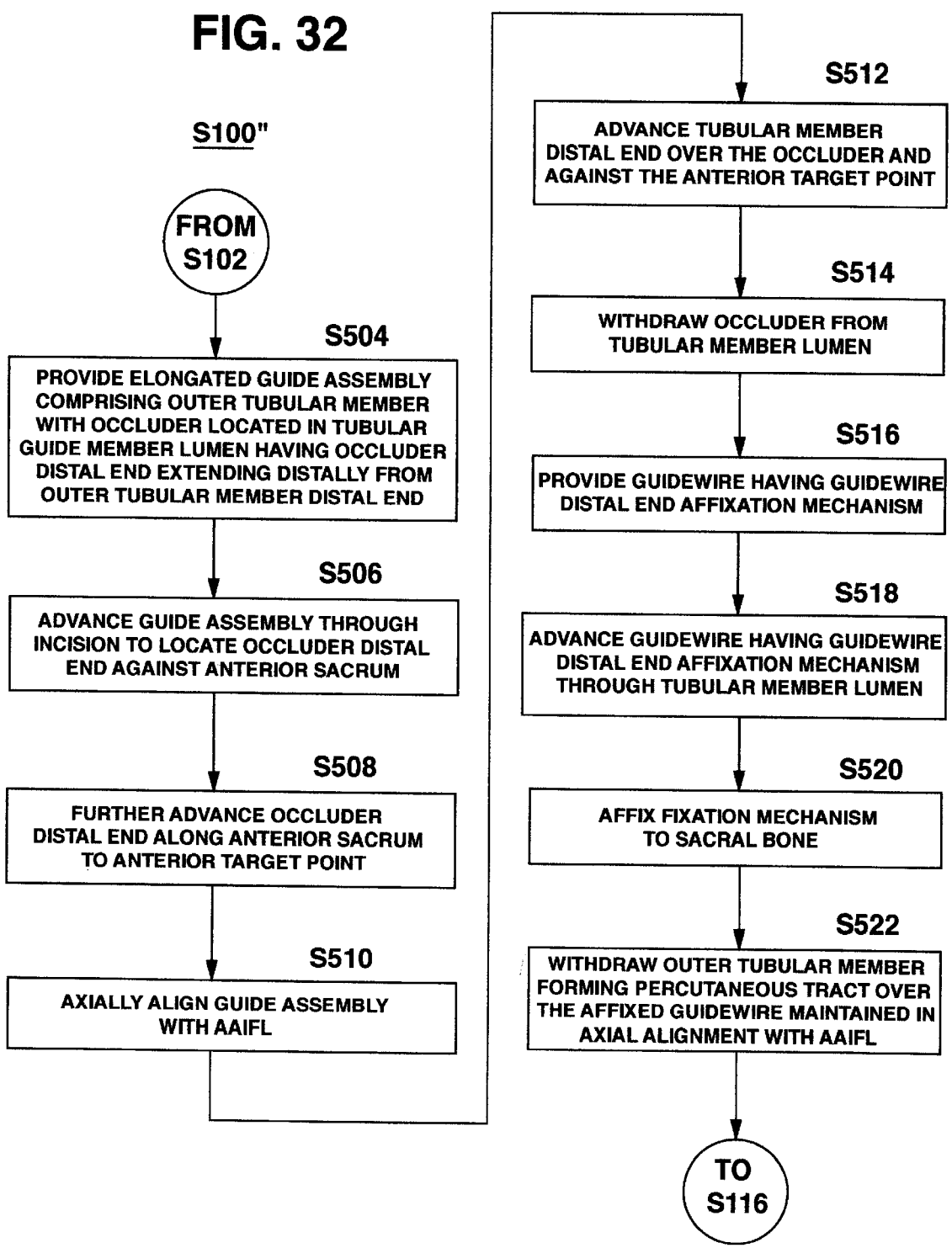
FIG. 32 is a flow chart showing particular steps of attaching a guidewire to the anterior target point to form an anterior, presacral, percutaneous tract maintained in axial alignment with the AAIFL.
Figure 33:
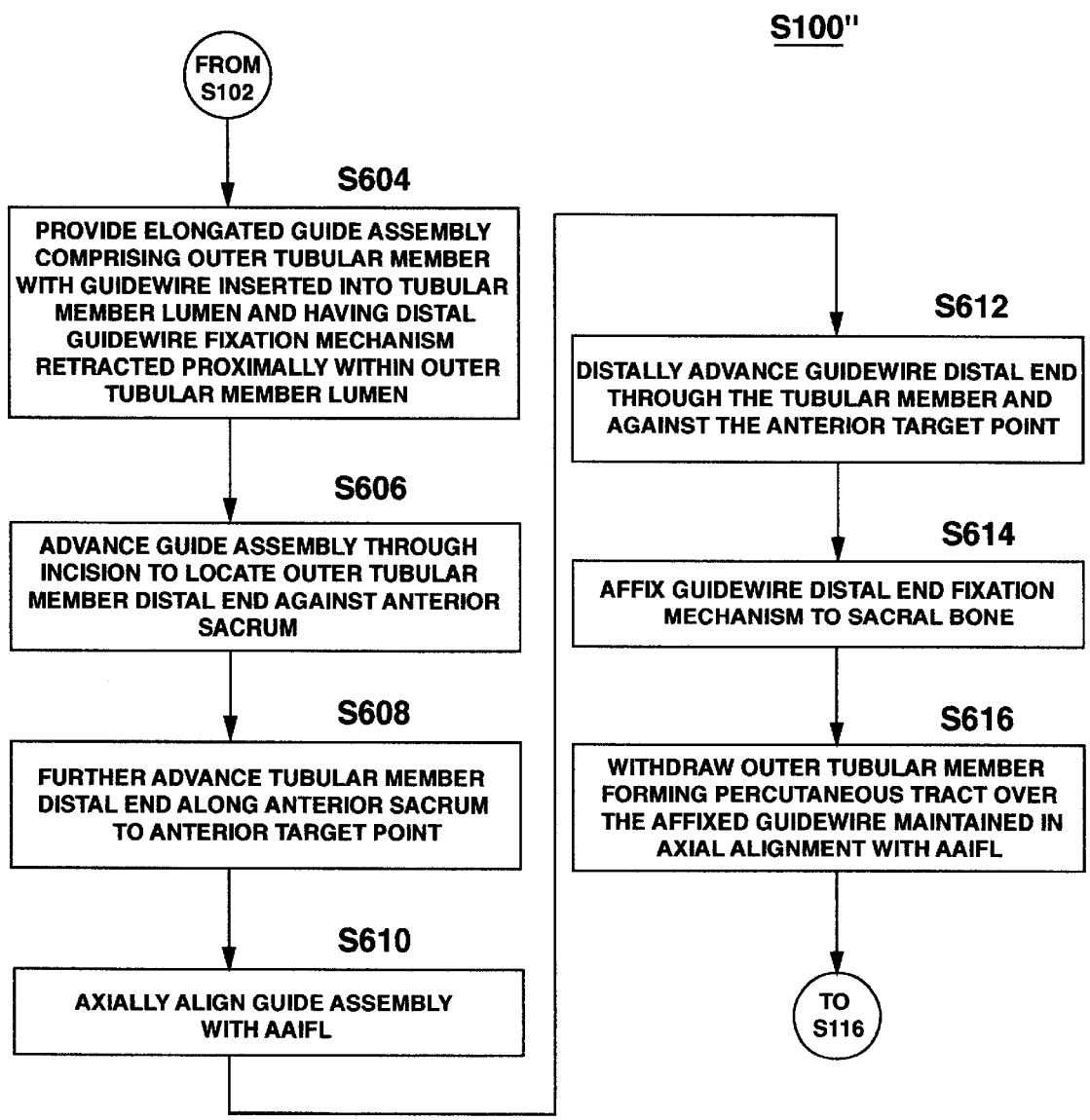
FIG. 33 is a flow chart showing alternative particular steps of attaching a guidewire to the anterior target point to form an anterior, presacral, percutaneous tract maintained in axial alignment with the AAIFL.
Figure 34:
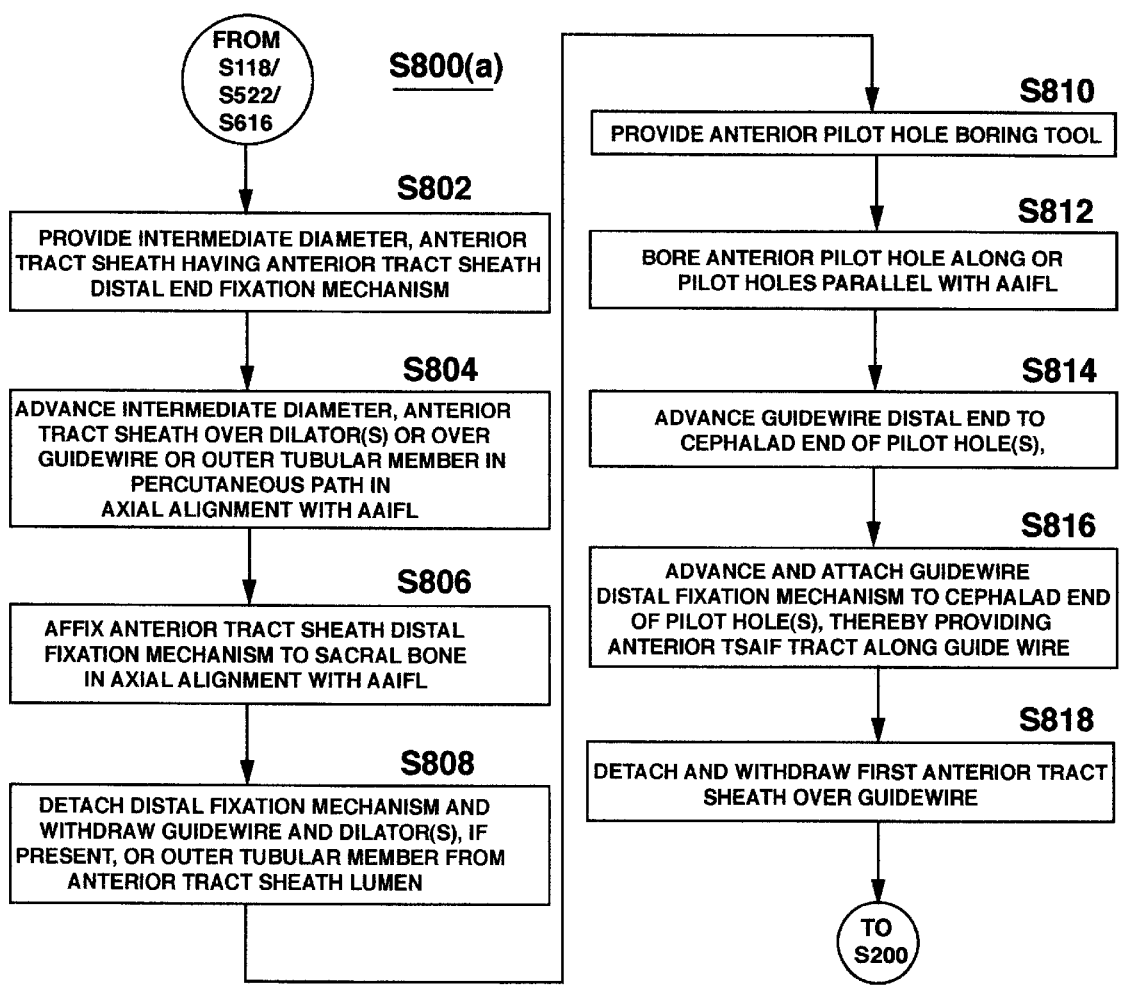
FIG. 34 is a flow chart showing steps of forming a pilot hole tracking the AAIFL and attaching a guidewire to the cephalad end of the pilot hole to form an anterior, presacral, percutaneous tract about the guidewire maintained in axial alignment with the AAIFL.

FIG. 32 shows alternative particular steps of step S100 for attaching a guidewire 80, 80' to the anterior target point to form an anterior, presacral, percutaneous tract maintained in axial alignment with the AAIFL as shown in FIG. 26. The guide assembly comprising the occluder 62 and tubular member 70 are provided, assembled, advanced and axially aligned with the AAIFL in steps S504–S512 as depicted in FIGS. 22 and 23. The occluder 62 is withdrawn from the tubular member lumen 74 in step S514, and the guidewire 80, 80' is provided in step S516. The guidewire 80, 80' is advanced through the tubular member lumen 74 in step S516 and S518 as shown in FIGS. 18 and 25. Then, the guidewire distal end fixation mechanism 82, 82' is advanced from the distal end opening of the tubular member lumen 74 and affixed to the sacral bone as shown in FIGS. 19 and 25. The tubular member 62 is then withdrawn in step S522, leaving the guidewire 80, 80' affixed and extending axially in alignment with the AAIFL through the presacral space. Steps S116–S122 of FIG. 12 can then be optionally performed as described above.

FIG. 32 shows alternative particular steps of attaching a guidewire 80, 80' to the anterior target point to form an anterior, presacral, percutaneous tract maintained in axial alignment with the AAIFL. In this embodiment, the guidewire 80, 80' is inserted into the tubular member lumen 74 to form the guide assembly in step S604. The guidewire distal fixation mechanism 82, 82' is retracted proximally within the tubular member lumen 74, and the tubular member distal end 76' is preferably blunt as shown in FIG. 18, for example. The guide assembly is advanced and axially aligned in steps S606–S610 in the manner shown in FIGS. 22 and 23. Then, the guidewire distal end fixation mechanism 82, 82' is advanced from the distal end opening of the tubular member lumen 74 and affixed to the sacral bone as shown in FIGS. 19 and 25. The tubular member 62 is then withdrawn in step S522, leaving the guidewire 80, 80' affixed and extending axially in alignment with the AAIFL through the presacral space. Steps S116–S122 of FIG. 12 can then be optionally performed as described above.

Three forms of anterior percutaneous tracts 26 are described above following alternative and optional steps of FIG. 12, that is, over the guidewire 80, 80' or over the tubular member 70, 70', 70", 70'", 70"" (optionally dilated), or through the anterior tract sheath lumen 96, 196. In each case, one or more anterior TASIF axial bores 22, 22' as shown in FIGS. 4 and 5 can be formed through these three forms of anterior percutaneous tracts 26. The anterior TASIF axial bores 22, 22' can be formed using the anterior TASIF axial bore hole boring tools 40 and 40' of FIGS. 44 and 45 starting at or around the anterior target point and extending along or parallel with the AAIFL in the cephalad direction to bore one or more relatively straight or curved anterior TASIF axial bore through S1 and into or through L5 and optionally through further lumbar vertebrae and any damaged or intact intervertebral discs.

Further embodiments of anterior, presacral, percutaneous tracts 26 are possible using a first anterior tract sheath 120 and pilot forming tool or drill 112 illustrated in FIG. 13. FIGS. 34–39 show steps of forming an anterior pilot hole 150 tracking the AAIFL and attaching a guidewire 80, 80' to the cephalad end of the pilot hole 150 to form an anterior, presacral, percutaneous tract about the guidewire 80, 80' maintained in axial alignment with the AAIFL. An intermediate anterior tract sheath or thread-tipped sheath 120 that is smaller in diameter than the enlarged tract sheath 96 and a boring tool, e.g., drill bit 112, sized to fit through the first tract sheath lumen 126, are provided in the tool set 60 that are used to form the pilot hole 150. The drill bit 112 is preferably a 1–5 mm diameter steel drill that is about 30 cm long having drill threads 116 at its sharpened end and is intended to be attached at its other end to a drill to be used to form a pilot hole along AAIFL. The intermediate anterior tract sheath 120 is preferably formed with a tract sheath distal end fixation mechanism, e.g., a distal screw thread 122, coupled to the distal end of sheath body 124. The thread-tipped sheath lumen 126 extends the length of the thread-tipped sheath 120 through both the distal screw thread 122 and the thread-tipped sheath body 124. The thread-tipped sheath 120 is preferably about 25 cm long and has an outer diameter or about 6.0–9.0 mm and an inner lumen diameter of about 3.5–5.5 mm. The thread-tipped sheath body 126 is preferably formed of a somewhat stiff plastic, e.g. urethane, and the distal screw thread 122 is preferably formed of a metal e.g., stainless steel. The distal screw thread 122 and distal end of the thread-tipped sheath body 126 are preferable thermally attached using an overlapping joinder. Again, alternative fixation mechanisms can be employed including the teeth 76''' depicted in FIG. 16.

Figure 35:
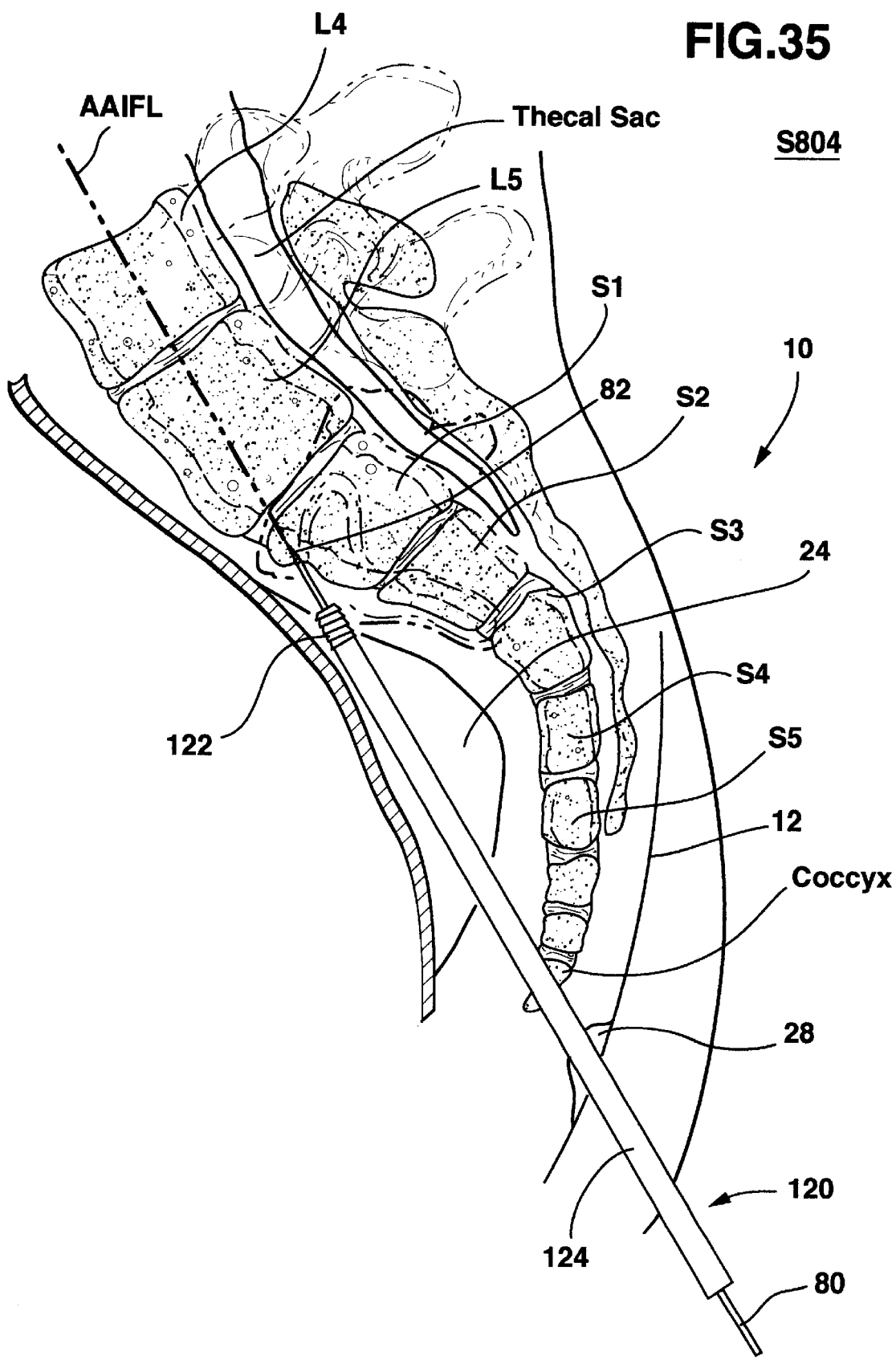
FIGS. 35–39 illustrate certain of the steps of FIG. 34.
Figure 36:
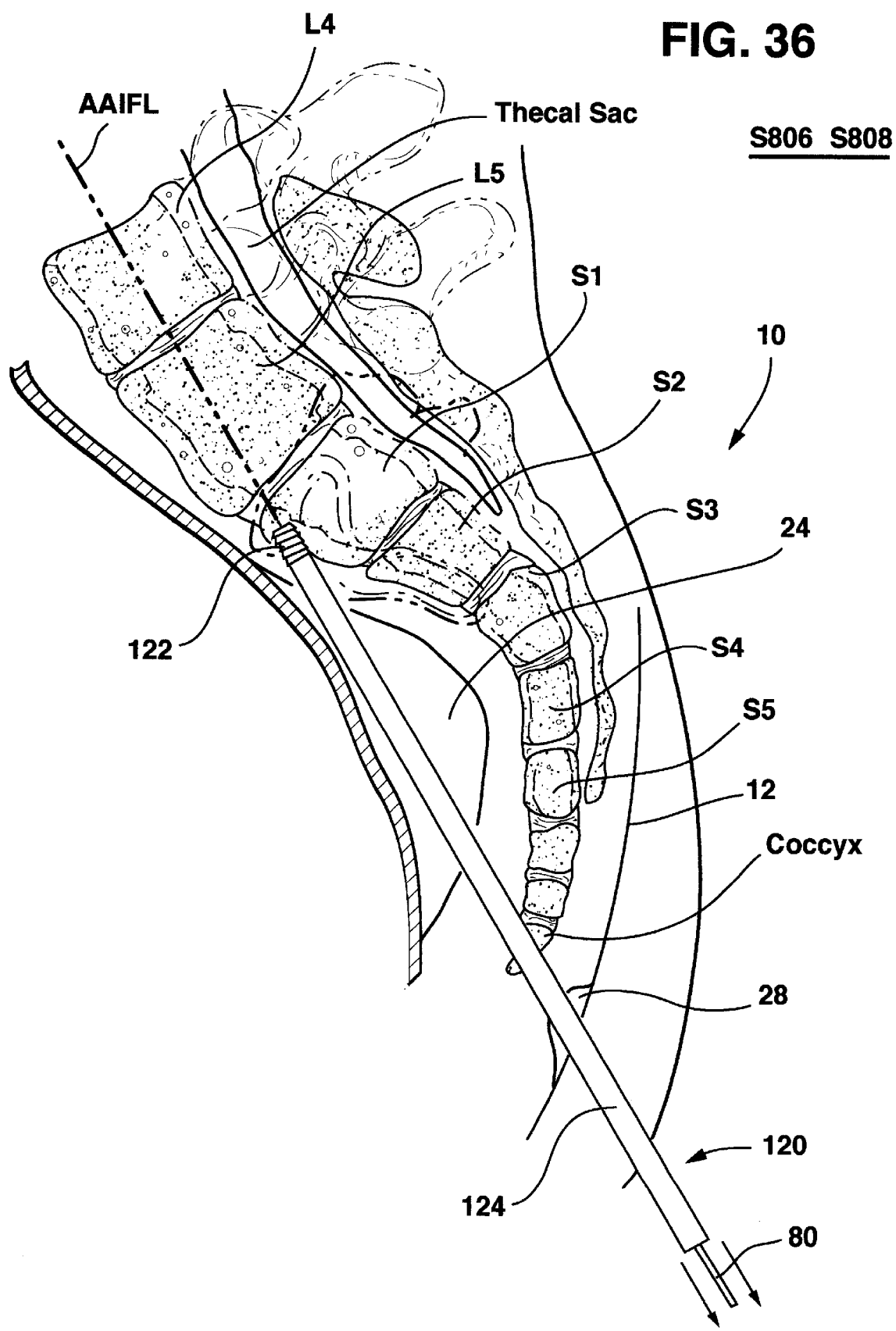

The intermediate anterior tract sheath 120 is adapted to be placed directly through the anterior tract and fixed in position in axial alignment with the AAIFL as shown in FIG. 36. However, the intermediate anterior tract sheath 120 can be advanced over the previously fixed and axially aligned guidewire 80, 80' or tubular member 70", 70'" or 70'" or over a dilator over either as indicated in step S804. For convenience, use of a fixed guidewire 80 and advancement of the thread-tipped sheath 120 over the guidewire 80 are illustrated in FIG. 35. The guidewire 80, 80' is attached to the sacral bone in any of the above-described ways leaving it in place as shown in FIG. 26.

In step S804, the thread-tipped sheath 120 is advanced over the guidewire 80, 80' until its distal screw thread 122 contacts the sacrum at the anterior target point. The thread-tipped sheath body 124 is axially aligned with the AAIFL, and the proximal end of the thread-tipped sheath body 124 is rotated to screw or thread the distal screw thread 122 into the sacrum bone as shown in FIG. 36. Then, in step S808, the distal screw-in tip 82 of the guidewire 80 is unscrewed from the sacrum bone and withdrawn from the sheath lumen 126 as also shown in FIG. 36. The guidewire proximal end may be reattached to the knob 81 to facilitate rotation of the guidewire 80 to unscrew the screw-in tip 82 from the sacral bone.

Figure 37:
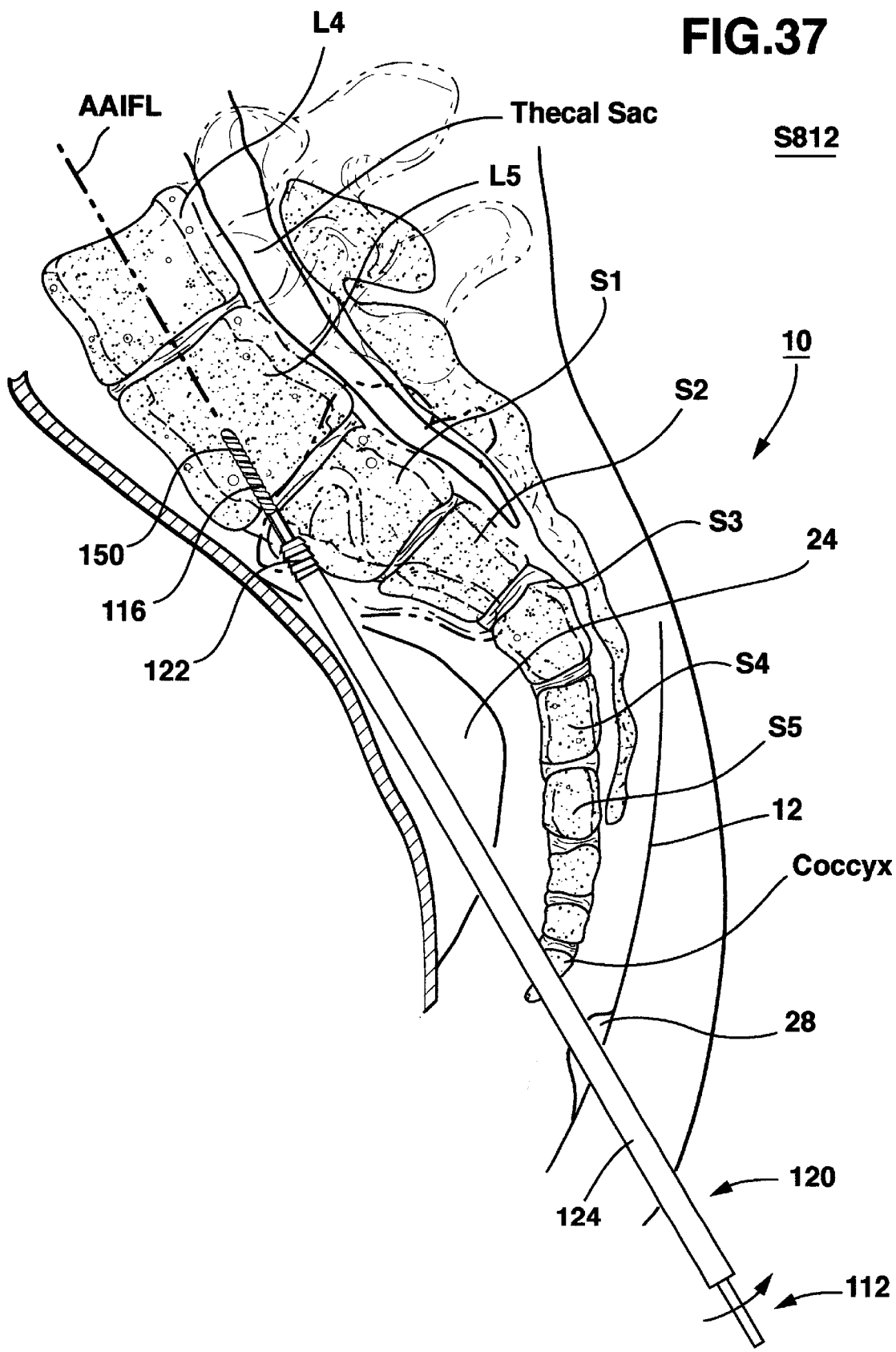
Figure 38:
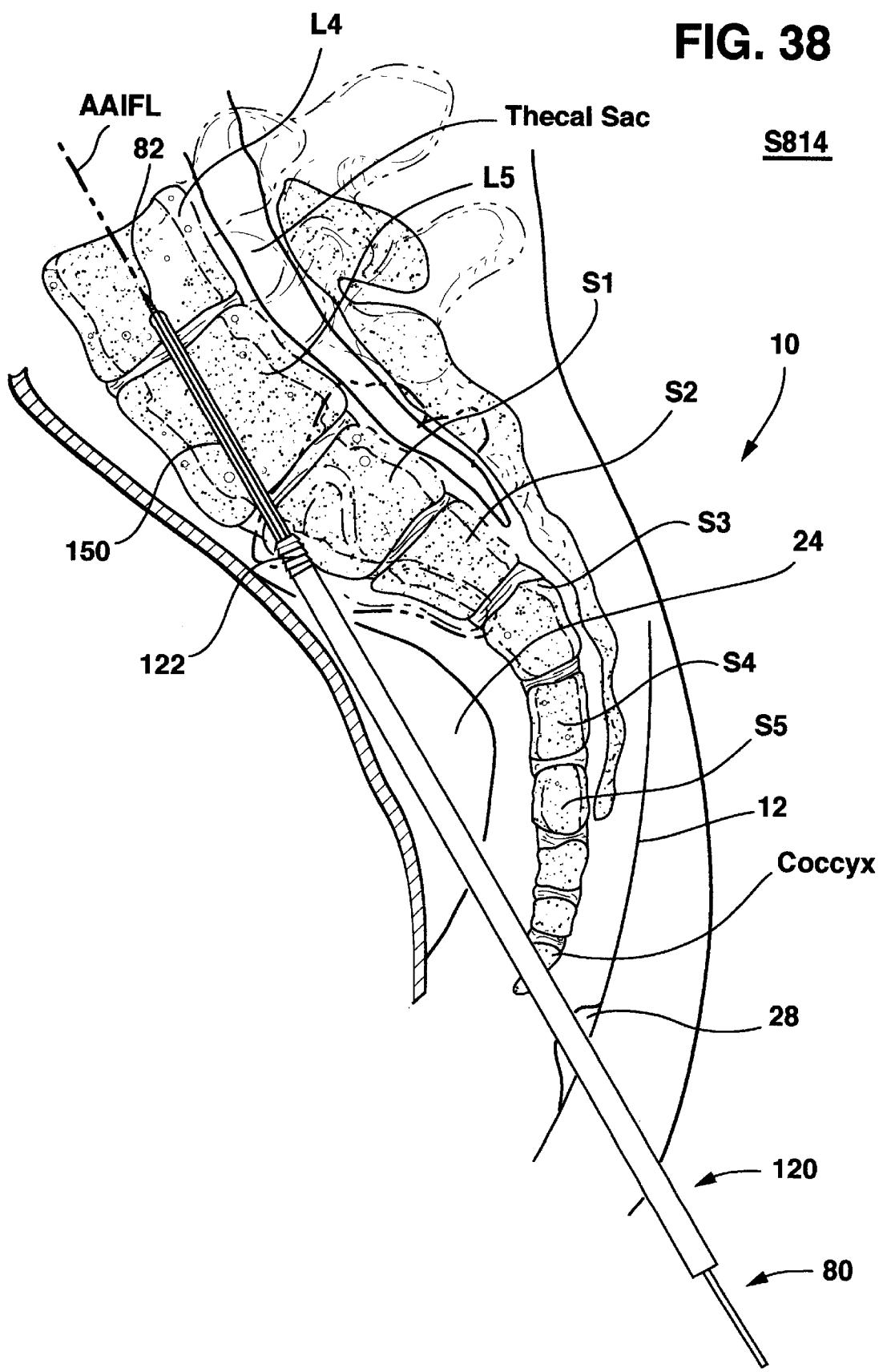

In step S812, the drill bit 112 is advanced through the sheath lumen 126 and is rotated by a drill motor (not shown) to drill out a pilot hole 150 aligned with the AAIFL under visualization cephalad through S1, L4 and L5, and the intervening discs as shown in FIG. 37. The drill bit 112 is then withdrawn from the pilot hole 150 and sheath lumen 126.

The thread-tipped sheath lumen 126 provides access from the skin incision to the pilot hole 150 to avoid blood infiltration into the pilot hole 150. Instruments, e.g., an endoscope, can be advanced therethrough and into the pilot hole to visualize the condition of the vertebral bodies and the discs traversed by the pilot hole 150. In addition, procedures including discectomy, disc augmentation and vertebroblasty can be performed by instruments advanced into the pilot hole 150 through the thread-tipped sheath lumen 126.

In step S814, the screw-in tip guidewire 80 is advanced through the sheath lumen 126 and the pilot hole 150 in step S814. The guidewire proximal end may be reattached to the knob 81, and the guidewire 80 is rotated to screw the screw-in tip 82 into vertebral bone at the cephalad end of the pilot hole 150 in step S816. The guidewire knob 81 is then removed, if reattached, and the proximal end of the thread-tipped sheath body 124 is rotated to unscrew the distal screw thread 122 from the sacral bone in step S818. The thread-tipped sheath 120 is then withdrawn from the presacral space over the guidewire 80.

Figure 39:
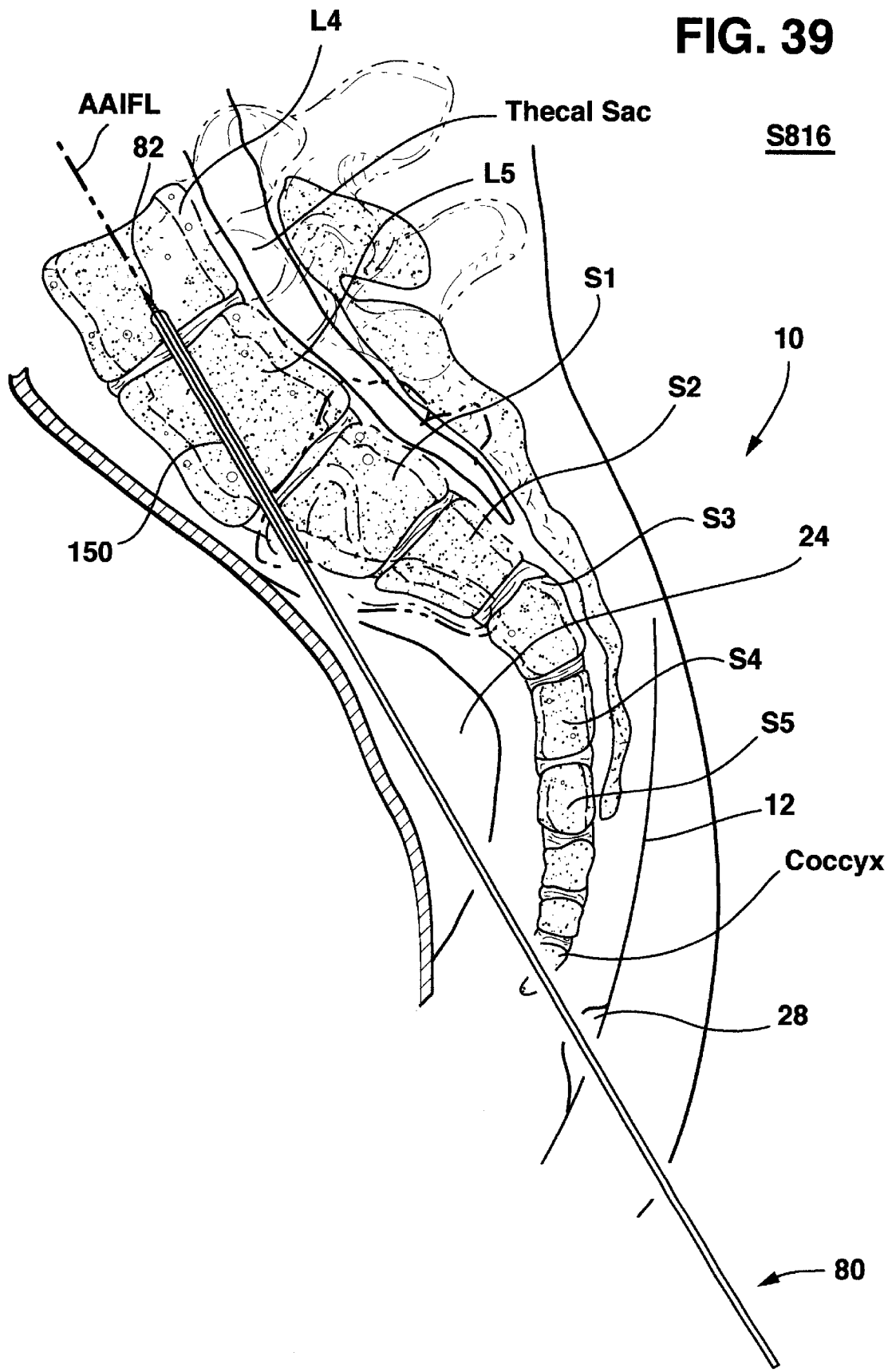

The guidewire 80 remains attached to and extending through the pilot bore 150 and presacral space 24 as shown in FIG. 39 thereby providing an anterior tract extending between the cephalad end of the pilot hole 150 and the skin incision 28. The pilot hole 150 may be expanded by a bore forming tool introduced over the guidewire 80.

FIGS. 40–43 show further method steps of dilating the presacral tissue around the affixed guidewire 80 of FIG. 39 and the insertion of an enlarged diameter anterior tract sheath 96 through the dilated presacral space to form the anterior, presacral, percutaneous tract 26 comprising the anterior tract sheath lumen 98. In the exemplary illustration of this surgical procedure, the balloon catheter 84 is provided in step S818 and employed in FIGS. 41 and 42 to dilate the sacral tissue, but it will be understood that other dilators, e.g., dilators 340, 350 could be employed alternatively.

Figure 41:
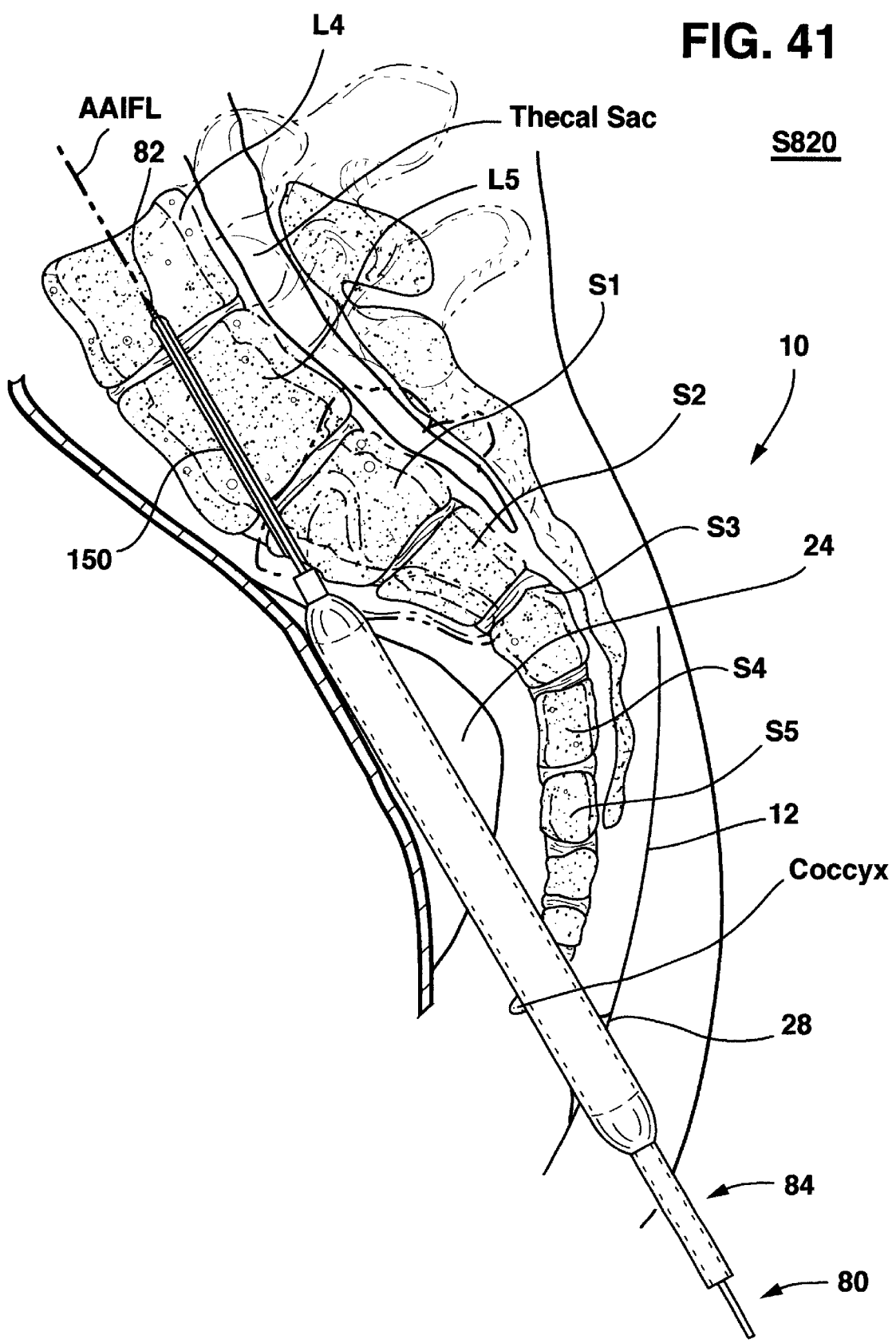
FIGS. 41–43 illustrate certain of the steps of FIG. 40.
Figure 42:
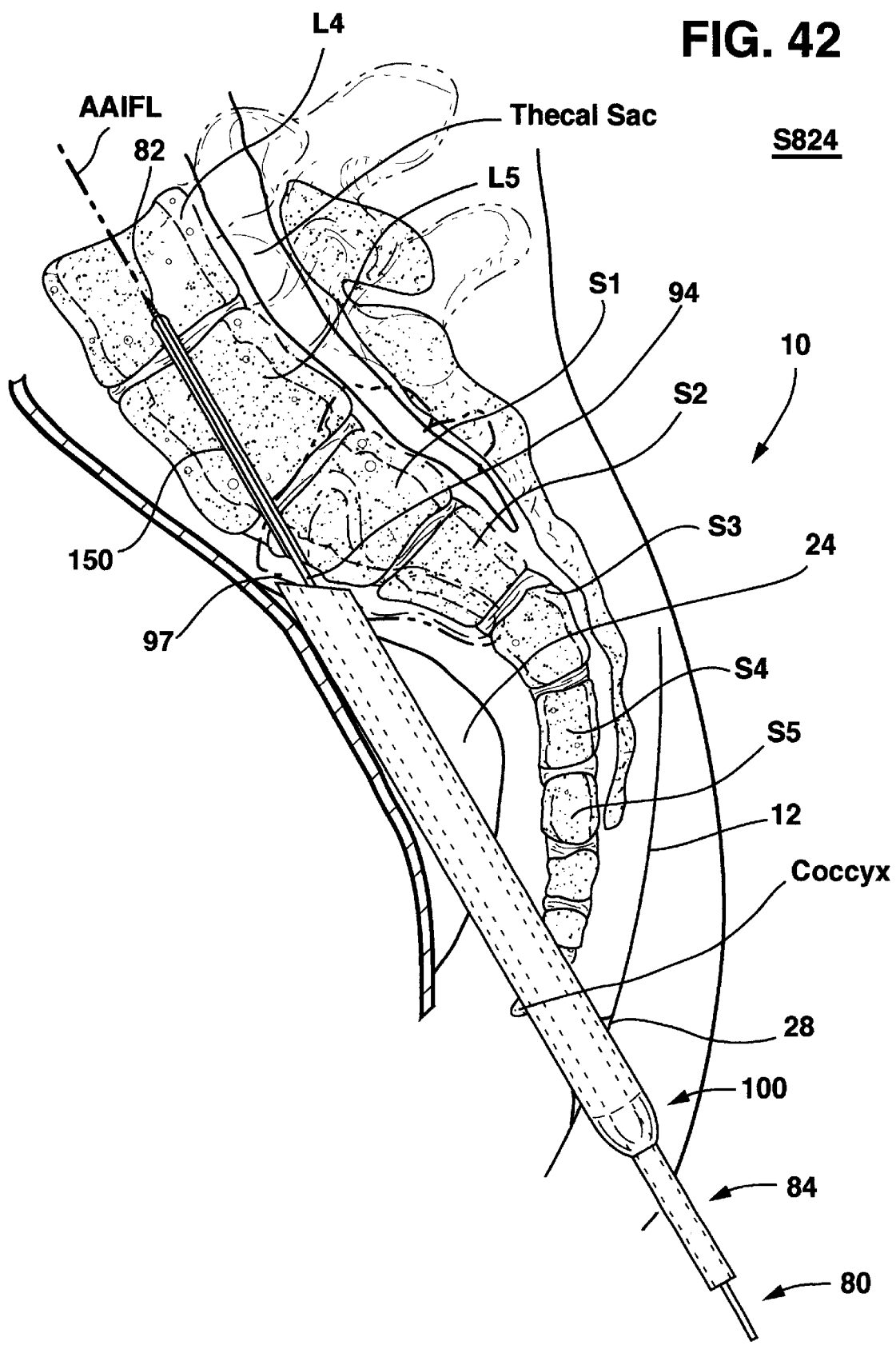
Figure 43:
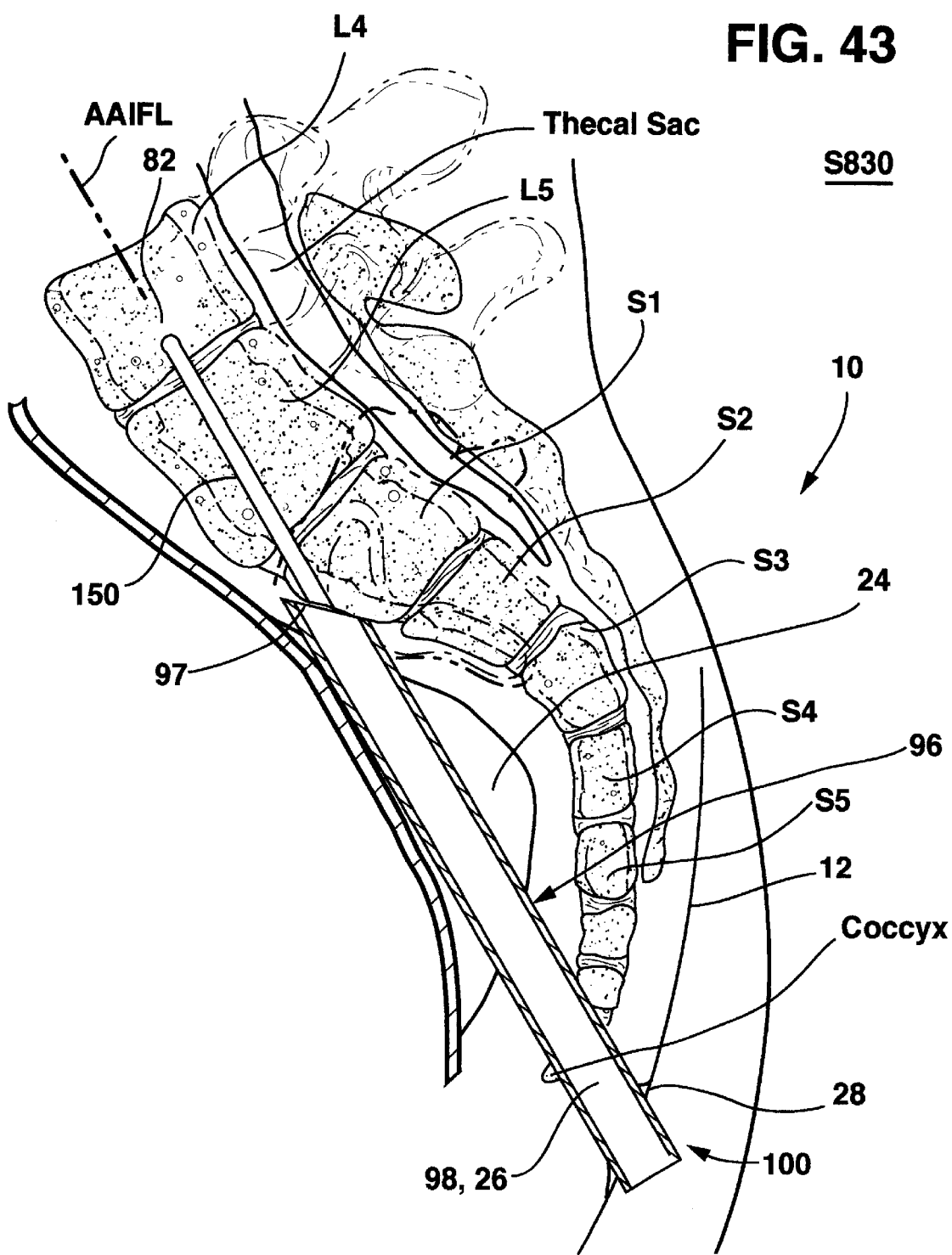

In step S820, the deflated dilatation balloon catheter 84 is advanced over the guidewire 80 until its distal end 94 abuts or enters the pilot hole 150 and is aligned axially with the AAIFL. The balloon 90 is then expanded under pressure to its rigid expanded diameter, and its expansion dilates the presacral tissue in the presacral space 24 as shown in FIG. 41. Then, in step S822, the anterior tract sheath 96 is inserted through the presacral space 24 over the expanded balloon 90 and rotated as necessary to aligned the shaped distal end 97 with the angle of the sacrum surrounding the pilot hole 150 as shown in FIG. 42

If an enlarged diameter, threaded tip, anterior tract sheath 196 is substituted for tract sheath 96 in step S822, it is advanced over the inflated balloon and fixed to the sacral bone surrounding the pilot hole 150 in the manner shown in FIGS. 30 and 31 in step S826.

The balloon 90 is deflated, and the balloon catheter 84 is withdrawn over the guidewire 80 from the anterior tract 26 in step S828 after the enlarged diameter, anterior tract sheath 96 or 196 is positioned or fixed. The guidewire 80 is optionally detached and withdrawn from the pilot hole 150 and tract sheath lumen 98, 198 in step S830. Step S100 of FIG. 6 is then completed, forming the anterior tract 26 aligned with the AAIFL and extending percutaneously to axially access the lumbar vertebrae as shown.

Step S200 of FIG. 6 is then also completed if the diameter of the pilot hole 150 is sufficient to be used as the TASIF axial bore for completion of steps S300 and S400. As noted above, step S300 of FIG. 6 may be performed using the pilot hole 150 formed in step S100 or using the enlarged diameter, anterior TASIF axial bore 152 formed using the anterior tracts 26 formed by any of the above-described procedures. The tools employed in the performance of step S300 may or may not require over-the-wire insertion using the guidewire 80. The guidewire proximal end may be reattached to the knob 81 to facilitate rotation of the guidewire 80 to unscrew the screw-in tip 82 from the vertebral body and removal of the guidewire 80 if it is not to be used in the completion of steps S300 and S400.

Figure 40:
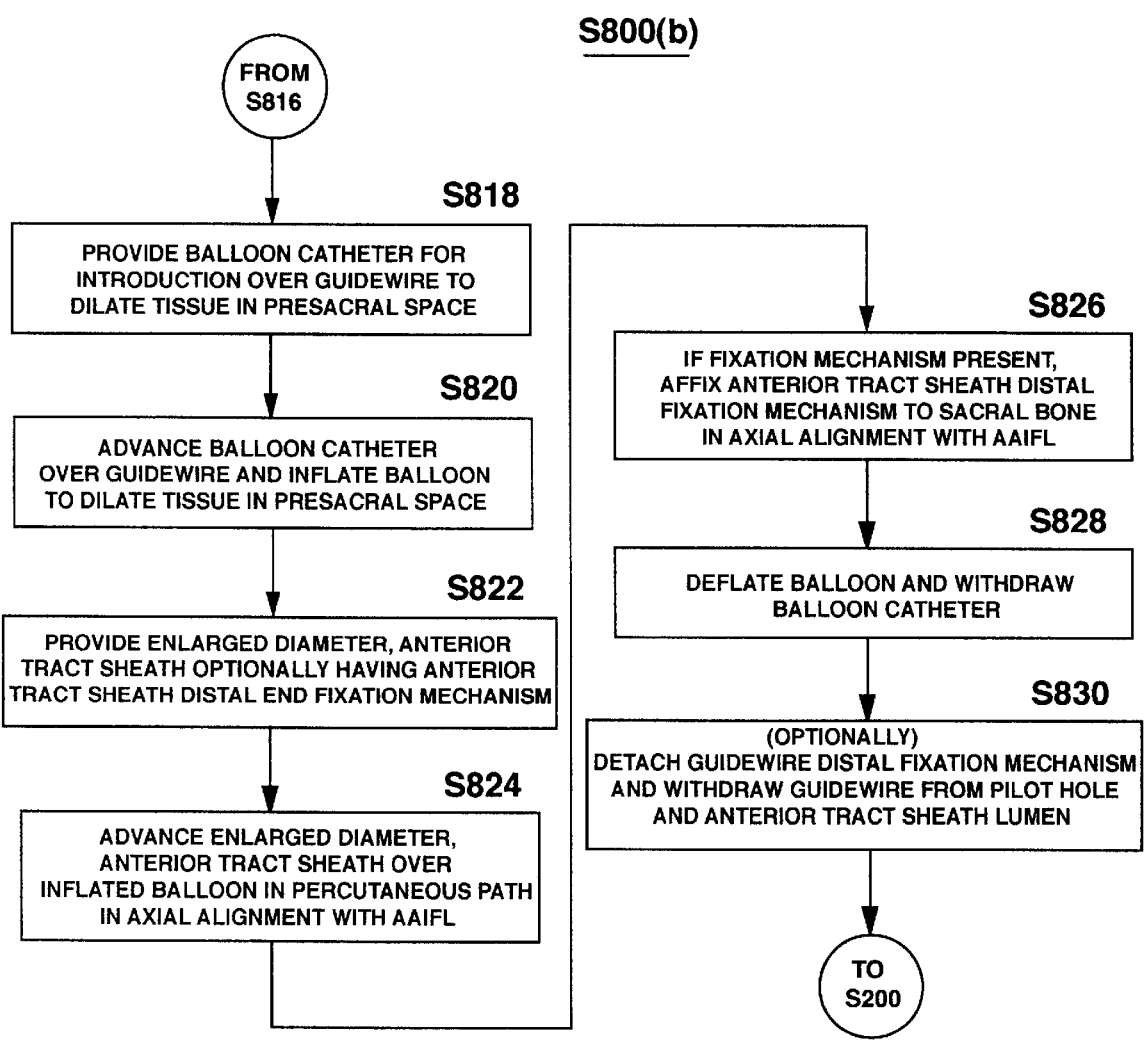
FIG. 40 is a flow chart showing steps of dilating the presacral tissue around the affixed guidewire of FIG. 39 and the insertion of an enlarged tubular anterior tract sheath through the dilated presacral space to form the anterior, presacral, percutaneous tract comprising the anterior tract sheath lumen.
Figure 46:
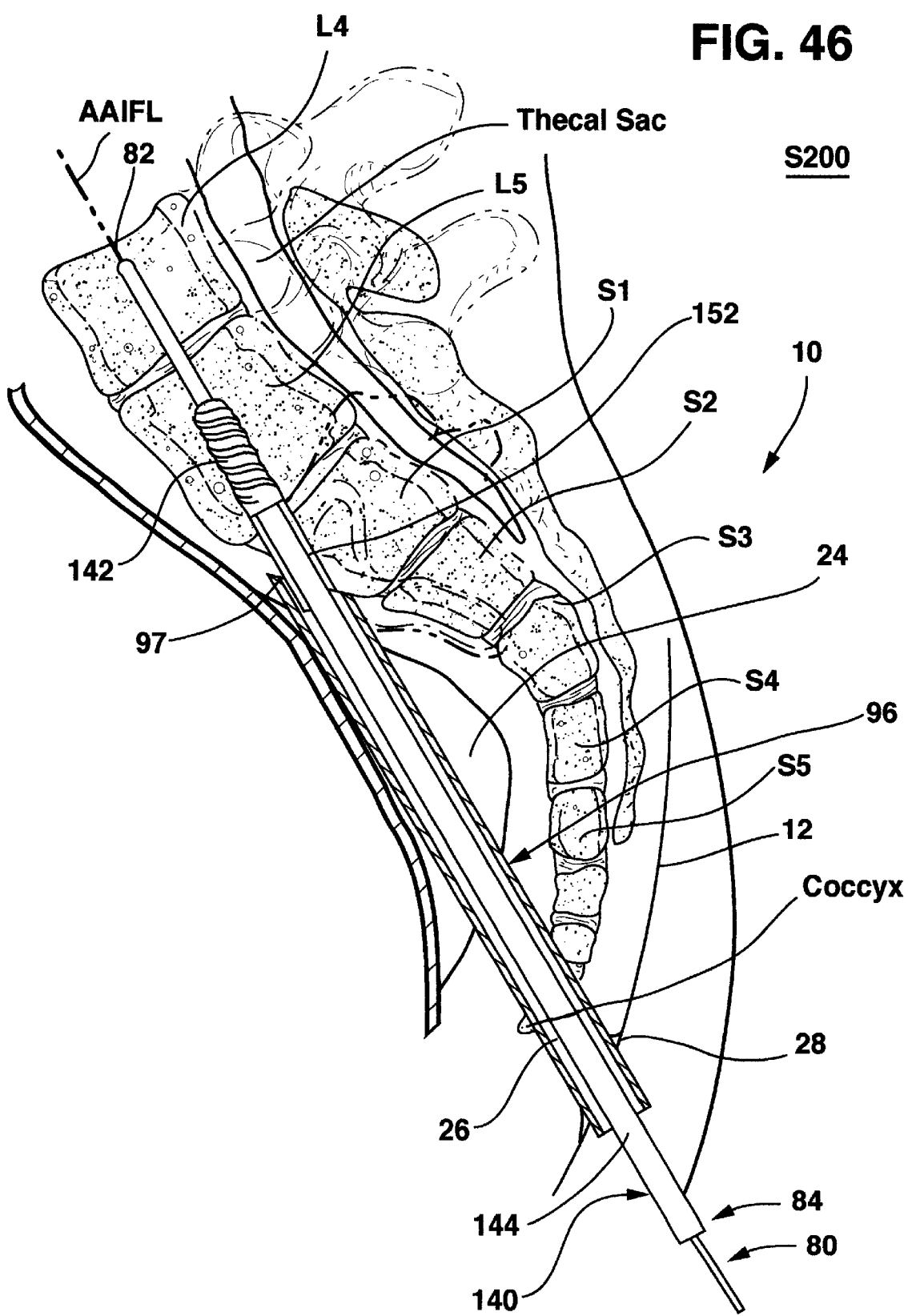
FIG. 46 illustrates the step of forming an anterior TASIF axial bore hole using an enlarged diameter drill bit.

Step S200 can be preferably performed following step S830 using an anterior axial bore forming tool set comprising the guidewire 80 attached to the cephalad end of the pilot hole and an enlarging tool 140 or one of the bore drilling tools 40 of FIG. 44 or 40' of FIG. 45. Either a straight or a curved anterior TASIF axial bore may be formed. One anterior approach to forming the anterior TASIF axial bore is illustrated in FIG. 46 wherein an enlarged bore forming drill bit or reamer 140 is advanced over the guidewire 80 to enlarge the pilot hole diameter and form the larger diameter anterior TASIF axial bore. Consequently, the guidewire 80 is left in place to perform step S200 using the enlarging tool 140. The larger diameter enlarging tool, e.g., a drill bit, ranguer or tap 140, used in step S200 preferably bores a 10.0 mm diameter anterior TASIF axial bore.

The guidewire screw-in tip 82 can then be unscrewed from the vertebral bone at the cephalad end of the anterior TASIF axial bore 152 as described above, if it is not needed to perform steps S300 and S400. The above-described procedure may be repeated to form two or more parallel anterior TASIF axial bores.

The longitudinal, TASIF axial bore that is formed in steps S100 and S200 of FIG. 6 and all of the embodiments thereof described above starts in the sacrum at the anterior target point and extends upwardly or cephalad through the vertebral body of S1 or S2 and through the cephalad vertebral bodies including L5 and L4 and the intervening discs denoted D4 and D5 in FIG. 1. Discs D4 and D5 are usually damaged or have degenerated between lumbar spine vertebrae and cause the pain experienced by patients requiring intervention and fusion of the vertebrae. A visual inspection, discectomy and/or disc augmentation and/or vertebroblasty may be performed pursuant to step S300 of FIG. 6 through the axially aligned anterior TASIF axial bore and anterior tract 26 to relieve the patient's symptoms and aid in the fusion achieved by a spinal implant or rod.

Although particular embodiments of the invention have been described herein in some detail, this has been done for the purpose of providing a written description of the invention in an enabling manner and to form a basis for establishing equivalents to structure and method steps not specifically described or listed. It is contemplated by the inventors that the scope of the limitations of the following claims encompasses the described embodiments and equivalents thereto now known and coming into existence during the term of the patent. Thus, it is expected that various changes, alterations, or modifications may be made to the invention as described herein without departing from the spirit and scope of the invention as defined by the appended claims.

What is claimed is:

1. A method of providing access to a series of adjacent vertebrae located within a human lumbar and sacral spine having an anterior aspect, a posterior aspect and an axial aspect, the vertebrae separated by intact or damaged spinal discs, the method comprising:

making an incision through the patient's skin adjacent to the coccyx aligned with a visualized anterior axial instrumentation/fusion line extending in said axial aspect through the series of adjacent vertebral bodies;

providing an elongated guide assembly having guide assembly proximal and distal ends, said guide assembly comprising an elongated tubular member having a tubular member lumen extending between proximal and distal tubular member ends, advancing the guide assembly through the incision to locate the guide assembly distal end against the anterior surface of the sacrum;

further advancing the guide assembly distal end along the anterior surface in the cephalad direction under visualization until the guide assembly distal end is at an anterior target point of a selected sacral vertebrae and the guide assembly body is aligned with the visualized anterior axial instrumentation/fusion line and extends percutaneously to the guide assembly proximal end; and advancing the tubular member distal end against the anterior surface at the anterior target point; whereby the tubular member provides a percutaneous tract over or through the tubular member from the incision site to the anterior target point and aligned axially with said visualized anterior axial instrumentation/fusion line.

2. The method of claim 1, wherein the step of providing an elongated guide assembly further comprises providing a beveled tip tubular member having a tubular member lumen within a tubular member body extending from a proximal tubular member end to a distal tubular member end as said elongated tubular member, the beveled tip beveled at an angle that is correlated with the angle of the surface of the sacrum at the anterior target point to the visualized anterior axial instrumentation/fusion line.

3. The method of claim 1, wherein the step of providing an elongated guide assembly further comprises providing a blunt tip tubular member having a tubular member lumen within a tubular member body extending from a proximal tubular member end to a distal tubular member end as said elongated tubular member.

4. The method of claim 1, wherein the step of providing an elongated guide assembly further comprises providing a trocar having a trocar lumen within a stiff trocar body extending from a proximal trocar end to a distal trocar end as said elongated tubular member.

5. The method of claim 1, wherein the step of providing an elongated guide assembly further comprises providing a guide sheath having a guide sheath lumen within a flexible guide sheath body extending from a proximal guide sheath end to a distal guide sheath end as said elongated tubular member.

6. The method of claim 1, further comprising:

providing a guidewire having a guidewire body extending between a guidewire proximal end and a guidewire distal end having a guidewire fixation mechanism for penetrating and affixing to bone at the guidewire distal end;

extending the guidewire through said tubular member lumen following removal of the occluder to locate the guidewire distal end at the anterior target point;

while maintaining said tubular member aligned axially with the visualized anterior axial instrumentation/fusion line, affixing the guidewire fixation mechanism to bone at the anterior target point; and removing the tubular member while maintaining the guidewire aligned with the visualized anterior axial instrumentation/fusion line, whereby the attached guidewire provides a percutaneous tract for over the wire passage extending from the skin incision to the anterior target point and aligned with the visualized anterior axial instrumentation/fusion line.

7. The method of claim 6, wherein said guidewire is formed with a flexible guidewire body.

8. The method of claim 6, wherein said guidewire is formed with a stiff guidewire body.

9. The method of claim 6, wherein the guidewire fixation mechanism comprises a distal screw-in tip adapted to be screwed into bone, and the step of affixing the guidewire fixation mechanism to bone at the anterior target point comprises rotating the guidewire body in a proximal section extending proximally from said tubular member lumen to screw said distal screw-in tip into sacral bone.

10. The method of claim 6, wherein the guidewire fixation mechanism comprises a distal sharpened tip adapted to be pushed into bone, and the step of affixing the guidewire fixation mechanism to bone at the anterior target point comprises pushing the guidewire body in a proximal section extending proximally from said tubular member lumen distally to push said distal sharpened tip into sacral bone.

11. A method of providing access to a series of adjacent vertebrae located within a human lumbar and sacral spine having an anterior aspect, a posterior aspect and an axial aspect, the vertebrae separated by intact or damaged spinal discs, the method comprising:

making an incision through the patient's skin adjacent to the coccyx aligned with a visualized anterior axial instrumentation/fusion line extending in said axial aspect through the series of adjacent vertebral bodies;

providing an elongated guide assembly having guide assembly proximal and distal ends, said guide assembly comprising an elongated tubular member having a tubular member lumen extending between proximal and distal tubular member ends and an elongated guidewire having a guidewire body extending between a guidewire proximal end and a guidewire distal end having a guidewire fixation mechanism for penetrating and affixing to bone at the guidewire distal end;

inserting the guidewire through said tubular member lumen to locate the guidewire distal end retracted within said tubular member lumen and said guidewire proximal end extending proximally from said tubular member proximal end;

advancing the guide assembly through the incision to locate the guide assembly distal end against the anterior surface of the sacrum;

further advancing the guide assembly distal end along the anterior surface in the cephalad direction under visualization until the guide assembly distal end is at an anterior target point of a selected sacral vertebrae and the guide assembly body is aligned with the visualized anterior axial instrumentation/fusion line and extends percutaneously to the guide assembly proximal end;

extending the guidewire through said tubular member lumen into contact with the sacrum;

while maintaining said tubular member aligned axially with the visualized anterior axial instrumentation/fusion line, affixing the guidewire fixation mechanism to sacral bone at the anterior target point; and removing the tubular member while maintaining the guidewire aligned with the visualized anterior axial instrumentation/fusion line, whereby the attached guidewire provides a percutaneous tract for over the wire passage extending from the skin incision to the anterior target point and aligned with the visualized anterior axial instrumentation/fusion line.

12. The method of claim 11, wherein the step of providing an elongated guide assembly further comprises providing a blunt tip tubular member having a tubular member lumen within a tubular member body extending from a proximal tubular member end to a distal tubular member end as said elongated tubular member.

13. The method of claim 11, wherein the step of providing an elongated guide assembly further comprises providing a trocar having a trocar lumen within a stiff trocar body extending from a proximal trocar end to a distal trocar end as said elongated tubular member.

14. The method of claim 11, herein the step of providing an elongated guide assembly further comprises providing a guide sheath having a guide sheath lumen within a flexible guide sheath body extending from a proximal guide sheath end to a distal guide sheath end as said elongated tubular member.

15. The method of claim 11, wherein said guidewire is formed with a flexible guidewire body.

16. The method of claim 11, wherein said guidewire is formed with a stiff guidewire body.

17. The method of claim 11, wherein the guidewire fixation mechanism comprises a distal screw-in tip adapted to be screwed into sacral bone, and the step of affixing the guidewire fixation mechanism to bone at the anterior target point comprises rotating the guidewire body in a proximal section extending proximally from said tubular member lumen to screw said distal screw-in tip into sacral bone.

18. The method of claim 11, wherein the guidewire fixation mechanism comprises a distal sharpened tip adapted to be pushed into sacral bone, and the step of affixing the guidewire fixation mechanism to bone at the anterior target point comprises pushing the guidewire body in a proximal section extending proximally from said tubular member lumen distally to push said distal sharpened tip into sacral bone.

19. The method of claim 11, further comprising:

dilating the tissue surrounding the guidewire body;

providing an enlarged diameter anterior tract sheath having a tract sheath lumen extending between proximal and distal anterior tract sheath ends; and inserting said anterior tract sheath through said enlarged anterior tissue tract over said guidewire to position said enlarged diameter anterior tract sheath distal end against the anterior sacrum with the anterior tract sheath lumen aligned axially with the visualized anterior axial instrumentation/fusion line.

20. The method of claim 11, further comprising:

providing a dilatation balloon catheter;

providing an enlarged diameter anterior tract sheath having a tract sheath lumen extending between proximal and distal anterior tract sheath ends;

with the guidewire aligned with the anterior axial instrumentation/fusion line, advancing the dilatation balloon catheter over the guidewire to locate a deflated balloon of the dilatation balloon catheter extending through presacral space;

expanding the deflated balloon to an expanded balloon diameter to dilate the presacral tissue between the anterior sacral surface and the skin incision;

advancing the enlarged diameter anterior tract sheath lumen over the expanded balloon to position the anterior tract sheath between the anterior target point and the skin incision and in alignment with the anterior axial instrumentation/fusion line; and deflating the balloon and withdrawing the balloon catheter from the anterior tract sheath lumen, whereby the anterior tract sheath lumen provides the anterior, presacral, percutaneous tract through the patient's presacral space.

21. The method of claim 11, further comprising:

providing a tissue dilator having a dilator body of a dilation diameter and a dilator lumen having a dilator lumen diameter sized to receive the guidewire and extending between proximal and distal dilator body ends;

passing the dilator over the guidewire toward the anterior target point to dilate the tissue surrounding the guidewire body; and withdrawing the tissue dilator from the guidewire body upon completion of dilation.

22. The method of claim 21, further comprising:

providing an enlarged diameter anterior tract sheath having a tract sheath lumen extending between proximal and distal anterior tract sheath ends; and inserting said anterior tract sheath through said enlarged anterior tissue tract to position said enlarged diameter anterior tract sheath distal end against the anterior sacrum with the anterior tract sheath lumen aligned axially with the visualized anterior axial instrumentation/fusion line.

23. The method of claim 11, further comprising:

providing a first tissue dilator having a dilator body of a dilation diameter and a dilator lumen having a dilator lumen diameter sized to receive the guidewire and extending between proximal and distal first tissue dilator body ends;

providing a second tissue dilator having a dilator body of a dilation diameter and a dilator lumen having a dilator lumen diameter sized to receive the first tissue dilator body and extending between proximal and distal second tissue dilator body ends;

passing the first tissue dilator over the guidewire toward the anterior target point to dilate the tissue surrounding the guidewire body;

passing the second tissue dilator over first tissue dilator and the guidewire toward the anterior target point to further dilate the tissue surrounding the guidewire body; and withdrawing the first and second tissue dilators from the guidewire body upon completion of dilation.

24. The method of claim 23, further comprising:

providing an enlarged diameter anterior tract sheath having a tract sheath lumen extending between proximal and distal anterior tract sheath ends; and inserting said anterior tract sheath through said enlarged anterior tissue tract to position said enlarged diameter anterior tract sheath distal end against the anterior sacrum with the anterior tract sheath lumen aligned axially with the visualized anterior axial instrumentation/fusion line.

25. The method of claim 11, further comprising:

providing an enlarged diameter tubular anterior tract sheath having a tract sheath lumen extending between proximal and distal anterior tract sheath ends and an anterior tract sheath distal fixation mechanism adapted to attach said enlarged diameter anterior tract sheath to sacral bone;

inserting said enlarged diameter anterior tract sheath through said enlarged anterior tissue tract over said guidewire to position said enlarged diameter anterior tract sheath distal end against the anterior sacrum with the anterior tract sheath lumen aligned axially with the visualized anterior axial instrumentation/fusion line; and operating said anterior tract sheath distal fixation mechanism to attach said anterior tract sheath to sacral bone with the anterior tract sheath lumen aligned axially with the visualized anterior axial instrumentation/fusion line.

26. The method of claim 25, wherein the anterior tract sheath fixation mechanism comprises distal screw threads encircling the distal anterior tract sheath end adapted to be screwed into bone, and the step of affixing the anterior tract sheath distal fixation mechanism to bone at the anterior target point comprises rotating the anterior tract sheath body in a proximal section extending from the skin incision to screw the distal screw threads into sacral bone.

27. The method of claim 11, further comprising the step of:

dilating the tissue between the skin incision and the anterior target point around the tubular member to provide an enlarged anterior tract through between the skin incision and the anterior target point.

28. The method of claim 27, further comprising:

providing an enlarged diameter tubular anterior tract sheath having a tract sheath lumen extending between proximal and distal anterior tract sheath ends and an anterior tract sheath distal fixation mechanism adapted to attach said enlarged diameter anterior tract sheath to sacral bone;

inserting said anterior tract sheath through said enlarged anterior tissue tract to position said enlarged diameter anterior tract sheath distal end against the anterior sacrum with the anterior tract sheath lumen aligned axially with the visualized anterior axial instrumentation/fusion line; and operating said anterior tract sheath distal fixation mechanism to attach said anterior tract sheath to sacral bone with the anterior tract sheath lumen aligned axially with the visualized anterior axial instrumentation/fusion line.

29. The method of claim 27, further comprising:

providing an enlarged diameter anterior tract sheath having a tract sheath lumen extending between proximal and distal anterior tract sheath ends with distal screw threads encircling the distal anterior tract sheath end adapted to be screwed into sacral bone;

inserting said enlarged diameter anterior tract sheath through said enlarged anterior tissue tract to position said enlarged diameter anterior tract sheath distal end against the anterior sacrum with the anterior tract sheath lumen aligned axially with the visualized anterior axial instrumentation/fusion line; and rotating the enlarged diameter anterior tract sheath body in a proximal section extending from the skin incision to screw the distal screw threads into sacral bone with the anterior tract sheath lumen aligned axially with the visualized anterior axial instrumentation/fusion line.

30. A method of providing access to a series of adjacent vertebrae located within a human lumbar and sacral spine having an anterior aspect, a posterior aspect and an axial aspect, the vertebrae separated by intact or damaged spinal discs, the method comprising:

making an incision through the patient's skin adjacent to the coccyx aligned with a visualized anterior axial instrumentation/fusion line extending in said axial aspect through the series of adjacent vertebral bodies;

providing an elongated guide assembly having guide assembly proximal and distal ends, said guide assembly comprising an elongated tubular member having a tubular member lumen extending between proximal and distal tubular member ends, said tubular member having a tubular member fixation mechanism at said distal tubular member end adapted to be fixed to sacral bone and an elongated occluder extending between a proximal occluder end and a distal occluder end that is blunt, inserting said occluder through said tubular member lumen to position said distal occluder end distally protruding from said tubular member fixation mechanism thereby forming a guide assembly distal end that is blunt and diminishes potential tissue penetration;

advancing the guide assembly through the incision to locate the guide assembly distal end against the anterior surface of the sacrum;

further advancing the guide assembly distal end along the anterior surface in the cephalad direction under visualization until the guide assembly distal end is at an anterior target point of a selected sacral vertebrae and the guide assembly body is aligned with the visualized anterior axial instrumentation/fusion line and extends percutaneously to the guide assembly proximal end;

advancing the tubular member distal end over the occluder and against the anterior surface at the anterior target point;

fixing said tubular member distal end to sacral bone while axially aligning said tubular member with the visualized anterior axial instrumentation/fusion line; and removing the occluder from the tubular member lumen, whereby the tubular member provides a percutaneous tract over or through the tubular member from the incision site to the anterior target point and aligned axially with said visualized anterior axial instrumentation/fusion line.

31. The method of claim 30, wherein the tubular member fixation mechanism comprises a distal threaded tip adapted to be screwed into bone, and the step of affixing the tubular member fixation mechanism to sacral bone at the anterior target point comprises rotating the tubular member in a proximal. section to screw said distal threaded tip into sacral bone.

32. The method of claim 30, wherein the tubular member fixation mechanism comprises distal sharpened teeth adapted to be pushed into sacral bone, and the step of affixing the tubular member fixation mechanism to bone at the anterior target point comprises pushing the tubular member distally to push said distal sharpened tip into sacral bone.

33. The method of claim 30, further comprising:
dilating the tissue surrounding the tubular member body;
providing an enlarged diameter anterior tract sheath having a tract sheath lumen extending between proximal and distal anterior tract sheath ends; and inserting said anterior tract sheath through said enlarged anterior tissue tract over said tubular member to position said enlarged diameter anterior tract sheath distal end against the anterior sacrum with the anterior tract sheath lumen aligned axially with the visualized anterior axial instrumentation/fusion line.

34. The method of claim 30, further comprising:
providing a dilatation balloon catheter;
providing an enlarged diameter anterior tract sheath having a tract sheath lumen extending between proximal and distal anterior tract sheath ends;
with the tubular member aligned with the anterior axial instrumentation/fusion line, advancing the dilatation balloon catheter over the tubular member to locate a deflated balloon of the dilatation balloon catheter extending through presacral space;
expanding the deflated balloon to an expanded balloon diameter to dilate the presacral tissue between the anterior sacral surface and the skin incision;
advancing the enlarged diameter anterior tract sheath lumen over the expanded balloon to position the anterior tract sheath between the anterior target point and the skin incision and in alignment with the anterior axial instrumentation/fusion line; and
deflating the balloon and withdrawing the balloon catheter from the anterior tract sheath lumen, whereby the anterior tract sheath lumen provides the anterior, presacral, percutaneous tract through the patient's presacral space.

35. The method of claim 30, further comprising:
providing a tissue dilator having a dilator body of a dilation diameter and a dilator lumen having a dilator lumen diameter sized to receive the tubular member and extending between proximal and distal dilator body ends;
passing the dilator over the tubular member toward the anterior target point to dilate the tissue surrounding the tubular member body; and
withdrawing the tissue dilator from the tubular member body upon completion of dilation.

36. The method of claim 35, further comprising:
providing an enlarged diameter anterior tract sheath having a tract sheath lumen extending between proximal and distal anterior tract sheath ends; and
inserting said anterior tract sheath through said enlarged anterior tissue tract to position said enlarged diameter anterior tract sheath distal end against the anterior sacrum with the anterior tract sheath lumen aligned axially with the visualized anterior axial instrumentation/fusion line.

37. The method of claim 30, further comprising:
providing a first tissue dilator having a dilator body of a dilation diameter and a dilator lumen having a dilator lumen diameter sized to receive the tubular member and extending between proximal and distal first tissue dilator body ends;
providing a second tissue dilator having a dilator body of a dilation diameter and a dilator lumen having a dilator lumen diameter sized to receive the first tissue dilator body and extending between proximal and distal second tissue dilator body ends;
passing the first tissue dilator over the tubular member toward the anterior target point to dilate the tissue surrounding the tubular member body;
passing the second tissue dilator over first tissue dilator and the tubular member toward the anterior target point to further dilate the tissue surrounding the tubular member body; and withdrawing the first and second tissue dilators from the tubular member body upon completion of dilation.

38. The method of claim 37, further comprising:

providing an enlarged diameter anterior tract sheath having a tract sheath lumen extending between proximal and distal anterior tract sheath ends; and inserting said anterior tract sheath through said enlarged anterior tissue tract to position said enlarged diameter anterior tract sheath distal end against the anterior sacrum with the anterior tract sheath lumen aligned axially with the visualized anterior axial instrumentation/fusion line.

39. The method of claim 30, further comprising:

providing an enlarged diameter tubular anterior tract sheath having a tract sheath lumen extending between proximal and distal anterior tract sheath ends and an anterior tract sheath distal fixation mechanism adapted to attach said enlarged diameter anterior tract sheath to sacral bone;

inserting said enlarged diameter anterior tract sheath through said enlarged anterior tissue tract over said tubular member to position said anterior tract sheath distal end against the anterior sacrum with the anterior tract sheath lumen aligned axially with the visualized anterior axial instrumentation/fusion line; and operating said anterior tract sheath distal fixation mechanism to attach said anterior tract sheath to sacral bone with the anterior tract sheath lumen aligned axially with the visualized anterior axial instrumentation/fusion line.

40. The method of claim 39, wherein the anterior tract sheath fixation mechanism comprises distal screw threads encircling the distal anterior tract sheath end adapted to be screwed into bone, and the step of affixing the anterior tract sheath distal fixation mechanism to bone at the anterior target point comprises rotating the anterior tract sheath body in a proximal section extending from the skin incision to screw the distal screw threads into sacral bone.

41. The method of claim 30, further comprising the step of:

dilating the tissue between the skin incision and the anterior target point around the tubular member to provide an enlarged anterior tract through between the skin incision and the anterior target point.

42. The method of claim 41, further comprising:

providing an enlarged diameter tubular anterior tract sheath having a tract sheath lumen extending between proximal and distal anterior tract sheath ends and an anterior tract sheath distal fixation mechanism adapted to attach said enlarged diameter anterior tract sheath to sacral bone;

inserting said anterior tract sheath through said enlarged anterior tissue tract to position said enlarged diameter anterior tract sheath distal end against the anterior sacrum with the anterior tract sheath lumen aligned axially with the visualized anterior axial instrumentation/fusion line; and operating said anterior tract sheath distal fixation mechanism to attach said anterior tract sheath to sacral bone with the anterior tract sheath lumen aligned axially with the visualized anterior axial instrumentation/fusion line.

43. The method of claim 41, further comprising:

providing an enlarged diameter anterior tract sheath having a tract sheath lumen extending between proximal and distal anterior tract sheath ends with distal screw threads encircling the distal anterior tract sheath end adapted to be screwed into sacral bone;

inserting said enlarged diameter anterior tract sheath through said enlarged anterior tissue tract to position said enlarged diameter anterior tract sheath distal end against the anterior sacrum with the anterior tract sheath lumen aligned axially with the visualized anterior axial instrumentation/fusion line; and rotating the enlarged diameter anterior tract sheath body in a proximal section extending from the skin incision to screw the distal screw threads into sacral bone with the anterior tract sheath lumen aligned axially with the visualized anterior axial instrumentation/fusion line.

44. A method of providing access to a series of adjacent vertebrae located within a human lumbar and sacral spine having an anterior aspect, a posterior aspect and an axial aspect, the vertebrae separated by intact or damaged spinal discs, the method comprising:

making an incision through the patient's skin adjacent to the coccyx aligned with a visualized anterior axial instrumentation/fusion line extending in said axial aspect through the series of adjacent vertebral bodies;

forming a tissue tract percutaneously between the skin incision and an anterior target point of a selected sacral vertebrae aligned with a visualized anterior axial instrumentation/fusion line extending in the cephalad direction though one or more vertebral bodies and intervening discs, if present, providing a boring tool for boring a pilot hole in the cephalad direction through one or more vertebral body and intervening disc, if present;

boring a pilot hole with the boring tool in the cephalad direction though the one or more vertebral bodies and intervening discs aligned axially with the visualized anterior axial instrumentation/fusion line;

providing a guidewire having a guidewire body extending between a guidewire proximal end and a guidewire distal end having a guidewire fixation mechanism for penetrating and affixing to bone at the guidewire distal end;

inserting the guidewire through the tissue tract and the pilot hole; and affixing the guidewire fixation mechanism to vertebral bone at the cephalad end of the pilot hole, whereby the attached guidewire provides a percutaneous tract for over the wire passage extending from the skin incision to the anterior target point and aligned with the visualized anterior axial instrumentation/fusion line.

45. The method of claim 44, wherein said guidewire is formed with a flexible guidewire body.

46. The method of claim 44, wherein said guidewire is formed with a stiff guidewire body.

47. The method of claim 44, wherein the guidewire fixation mechanism comprises a distal screw-in tip adapted to be screwed into vertebral bone, and the step of affixing the guidewire fixation mechanism to bone at the cephalad end of the pilot hole comprises rotating the guidewire body in a proximal section extending proximally from said tubular member lumen to screw said distal screwin tip into vertebral bone.

48. The method of claim 44, wherein the guidewire fixation mechanism comprises a distal sharpened tip adapted to be pushed into vertebral bone, and the step of affixing the guidewire fixation mechanism to vertebral bone at the cephalad end of the pilot hole comprises pushing the guidewire body in a proximal section extending proximally from said tubular member lumen distally to push said distal sharpened tip into vertebral bone.

49. The method of claim 44, further comprising:

dilating the tissue surrounding the guidewire body outside the pilot hole;

providing an enlarged diameter anterior tract sheath having a tract sheath lumen extending between proximal and distal anterior tract sheath ends; and inserting said anterior tract sheath through said enlarged anterior tissue tract over said guidewire to position said enlarged diameter anterior tract sheath distal end against the anterior sacrum with the anterior tract sheath lumen aligned axially with the visualized anterior axial instrumentation/fusion line.

50. The method of claim 44, further comprising:

providing a dilatation balloon catheter;

providing an enlarged diameter anterior tract sheath having a tract sheath lumen extending between proximal and distal anterior tract sheath ends;

with the guidewire aligned with the anterior axial instrumentation/fusion line, advancing the dilatation balloon catheter over the guidewire to locate a deflated balloon of the dilatation balloon catheter extending through presacral space;

expanding the deflated balloon to an expanded balloon diameter to dilate the presacral tissue between the pilot hole and the skin incision;

advancing the enlarged diameter anterior tract sheath lumen over the expanded balloon to position the anterior tract sheath between the anterior target point and the skin incision and in alignment with the anterior axial instrumentation/fusion line; and deflating the balloon and withdrawing the balloon catheter from the anterior tract sheath lumen, whereby the anterior tract sheath lumen provides the anterior, presacral, percutaneous tract through the patient's presacral space.

51. The method of claim 44, further comprising:

providing a tissue dilator having a dilator body of a dilation diameter and a dilator lumen having a dilator lumen diameter sized to receive the guidewire and extending between proximal and distal dilator body ends;

passing the dilator over the guidewire toward the anterior target point to dilate the tissue surrounding the guidewire body; and withdrawing the tissue dilator from the guidewire body upon completion of dilation.

52. The method of claim 51, further comprising:

providing an enlarged diameter anterior tract sheath having a tract sheath lumen extending between proximal and distal anterior tract sheath ends; and inserting said anterior tract sheath through said enlarged anterior tissue tract to position said enlarged diameter anterior tract sheath distal end against the anterior sacrum with the anterior tract sheath lumen aligned axially with the visualized anterior axial instrumentation/fusion line.

53. The method of claim 44, further comprising:

providing a first tissue dilator having a dilator body of a dilation diameter and a dilator lumen having a dilator lumen diameter sized to receive the guidewire and extending between proximal and distal first tissue dilator body ends;

providing a second tissue dilator having a dilator body of a dilation diameter and a dilator lumen having a dilator lumen diameter sized to receive the first tissue dilator body and extending between proximal and distal second tissue dilator body ends;

passing the first tissue dilator over the guidewire toward the anterior target point to dilate the tissue surrounding the guidewire body;

passing the second tissue dilator over first tissue dilator and the guidewire toward the anterior target point to further dilate the tissue surrounding the guidewire body; and withdrawing the first and second tissue dilators from the guidewire body upon completion of dilation.

54. The method of claim 33, further comprising:

providing an enlarged diameter anterior tract sheath having a tract sheath lumen extending between proximal and distal anterior tract sheath ends; and inserting said anterior tract sheath through said enlarged anterior tissue tract to position said enlarged diameter anterior tract sheath distal end against the anterior sacrum with the anterior tract sheath lumen aligned axially with the visualized anterior axial instrumentation/fusion line.

55. The method of claim 44, further comprising:

providing an enlarged diameter tubular anterior tract sheath having a tract sheath lumen extending between proximal and distal anterior tract sheath ends and an anterior tract sheath distal fixation mechanism adapted to attach said enlarged diameter anterior tract sheath to sacral bone;

inserting said enlarged diameter anterior tract sheath through said enlarged anterior tissue tract over said guidewire to position said enlarged diameter anterior tract sheath distal end against the anterior sacrum with the anterior tract sheath lumen aligned axially with the visualized anterior axial instrumentation/fusion line; and operating said anterior tract sheath distal fixation mechanism to attach said anterior tract sheath to sacral bone with the anterior tract sheath lumen aligned axially with the visualized anterior axial instrumentation/fusion line.

56. The method of claim 55, wherein the anterior tract sheath fixation mechanism comprises distal screw threads encircling the distal anterior tract sheath end adapted to be screwed into bone, and the step of affixing the anterior tract sheath distal fixation mechanism to bone at the anterior target point comprises rotating the anterior tract sheath body in a proximal section extending from the skin incision to screw the distal screw threads into sacral bone.

57. The method of claim 44, further comprising the step of:

dilating the tissue between the skin incision and the anterior target point around the tubular member to provide an enlarged anterior tract through between the skin incision and the anterior target point.

58. The method of claim 57, further comprising:

providing an enlarged diameter tubular anterior tract sheath having a tract sheath lumen extending between proximal and distal anterior tract sheath ends and an anterior tract sheath distal fixation mechanism adapted to attach said enlarged diameter anterior tract sheath to sacral bone;

inserting said anterior tract sheath through said enlarged anterior tissue tract to position said enlarged diameter anterior tract sheath distal end against the anterior sacrum with the anterior tract sheath lumen aligned axially with the visualized anterior axial instrumentation/fusion line; and operating said anterior tract sheath distal fixation mechanism to attach said anterior tract sheath to sacral bone with the anterior tract sheath lumen aligned axially with the visualized anterior axial instrumentation/fusion line.

59. The method of claim 57, further comprising:

providing an enlarged diameter anterior tract sheath having a tract sheath lumen extending between proximal and distal anterior tract sheath ends with distal screw threads encircling the distal anterior tract sheath end adapted to be screwed into sacral bone;

inserting said enlarged diameter anterior tract sheath through said enlarged anterior tissue tract to position said enlarged diameter anterior tract sheath distal end against the anterior sacrum with the anterior tract sheath lumen aligned axially with the visualized anterior axial instrumentation/fusion line; and rotating the enlarged diameter anterior tract sheath body in a proximal section extending from the skin incision to screw the distal screw threads into sacral bone with the anterior tract sheath lumen aligned axially with the visualized anterior axial instrumentation/fusion line.

60. The method of claim 44, further comprising:

providing an intermediate anterior tract sheath having a tract sheath lumen extending between proximal and distal intermediate anterior tract sheath ends;

after said guidewire is affixed to the anterior target point, inserting said intermediate anterior tract sheath through said enlarged anterior tissue tract over said guidewire to position said distal intermediate anterior tract sheath distal end against the anterior sacrum with the intermediate anterior tract sheath lumen aligned axially with the visualized anterior axial instrumentation/fusion line; and withdrawing said guidewire from the intermediate anterior tract sheath lumen; and wherein:

the boring step further comprises:

inserting the boring tool through the intermediate anterior tract sheath lumen to the anterior target point;

then boring the pilot hole in the cephalad direction through one or more vertebral body and intervening disc, if present, aligned with the visualized anterior axial instrumentation/fusion line; and withdrawing the boring tool.

61. A method of providing access to a series of adjacent vertebrae located within a human lumbar and sacral spine having an anterior aspect, a posterior aspect and an axial aspect, the vertebrae separated by intact or damaged spinal discs, the method comprising:

making an incision through the patient's skin adjacent to the coccyx aligned with a visualized anterior axial instrumentation/fusion line extending in said axial aspect through the series of adjacent vertebral bodies;

providing an elongated guide assembly having guide assembly proximal and distal ends, said guide assembly comprising an elongated tubular member having a tubular member lumen extending between proximal and distal tubular member ends and an elongated occluder extending between a proximal occluder end and a distal occluder end that is blunt, inserting said occluder through said tubular member lumen to position said distal occluder end at or distally protruding from said distal tubular member end thereby forming a guide assembly distal end that is blunt and diminishes potential tissue penetration;

advancing the guide assembly through the incision to locate the guide assembly distal end against the anterior surface of the sacrum;

further advancing the guide assembly distal end along the anterior surface in the cephalad direction under visualization until the guide assembly distal end is at an anterior target point of a selected sacral vertebrae and the guide assembly body is aligned with the visualized anterior axial instrumentation/fusion line and extends percutaneously to the guide assembly proximal end;

advancing the tubular member distal end over the occluder and against the anterior surface at the anterior target point;

removing the occluder from the tubular member lumen;

providing a guidewire having a guidewire body extending between a guidewire proximal end and a guidewire distal end having a guidewire fixation mechanism for penetrating and affixing to bone at the guidewire distal end;

extending the guidewire through said tubular member lumen following removal of the occluder to locate the guidewire distal end at the anterior target point;

while maintaining said tubular member aligned axially with the visualized anterior axial instrumentation/fusion line, affixing the guidewire fixation mechanism to bone at the anterior target point;

removing the tubular member while maintaining the guidewire aligned with the visualized anterior axial instrumentation/fusion line;

dilating the tissue between the skin incision and the anterior target point around the guidewire to provide an enlarged anterior tissue tract through between the skin incision and the anterior target point;

providing an intermediate anterior tract sheath having a tract sheath lumen extending between proximal and distal intermediate anterior tract sheath ends;

inserting said intermediate anterior tract sheath through said enlarged anterior tissue tract over said guidewire to position said distal intermediate anterior tract sheath distal end against the anterior sacrum with the intermediate anterior tract sheath lumen aligned axially with the visualized anterior axial instrumentation/fusion line;

withdrawing said guidewire from the intermediate anterior tract sheath lumen;

providing a boring tool for boring a pilot hole in the cephalad direction through one or more vertebral body and intervening disc, if present;

inserting the boring tool through the intermediate anterior tract sheath lumen to the anterior target point, boring a pilot hole in the cephalad direction through one or more vertebral body and intervening disc, if present, aligned with the visualized anterior axial instrumentation/fusion line, and withdrawing the boring tool;

inserting the guidewire through the intermediate anterior tract sheath lumen and the pilot hole affixing the guidewire fixation mechanism to vertebral bone at the cephalad end of the pilot hole; and withdrawing the intermediate anterior tract sheath.

whereby the attached guidewire provides a percutaneous tract for over the wire passage extending from the skin incision to the anterior target point and aligned with the visualized anterior axial instrumentation/fusion line.

62. The method of claim 61, wherein the step of providing an elongated guide assembly further comprises providing a beveled tip tubular member having a tubular member lumen within a tubular member body extending from a proximal tubular member end to a distal tubular member end as said elongated tubular member, the beveled tip beveled at an angle that is correlated with the angle of the surface of the sacrum at the anterior target point to the visualized anterior axial instrumentation/fusion line.

63. The method of claim 61, wherein the step of providing an elongated guide assembly further comprises providing a blunt tip tubular member having a tubular member lumen within a tubular member body extending from a proximal tubular member end to a distal tubular member end as said elongated tubular member.

64. The method of claim 61, wherein the step of providing an elongated guide assembly further comprises providing a trocar having a trocar lumen within a stiff trocar body extending from a proximal trocar end to a distal trocar end as said elongated tubular member.

65. The method of claim 61, wherein the step of providing an elongated guide assembly further comprises providing a guide sheath having a guide sheath lumen within a flexible guide sheath body extending from a proximal guide sheath end to a distal guide sheath end as said elongated tubular member.

66. The method of claim 61, wherein said guidewire is formed with a flexible guidewire body.

67. The method of claim 61, wherein said guidewire is formed with a stiff guidewire body.

68. The method of claim 61, wherein the guidewire fixation mechanism comprises a distal screw-in tip adapted to be screwed into bone, and the steps of affixing the guidewire fixation mechanism to bone at the anterior target point and the cephalad end of the pilot hole comprises rotating the guidewire body in a proximal section extending proximally from said tubular member lumen to screw said distal screw-in tip into bone.

69. The method of claim 61, further comprising the step of:
following the removal of the intermediate anterior tract sheath, dilating the tissue between the skin incision and the anterior target point around the guidewire attached to the cephalad end of the pilot hole to provide an enlarged anterior tract through between the skin incision and the anterior target point.

70. The method of claim 61, further comprising:
following the removal of the intermediate anterior tract sheath, dilating the tissue between the skin incision and the anterior target point around the guidewire attached to the cephalad end of the pilot hole to provide an enlarged anterior tract through between the skin incision and the anterior target point;
dilating the tissue between the skin incision and the anterior target point around the guidewire to provide an enlarged anterior tissue tract through between the skin incision and the anterior target point;
providing an enlarged diameter tubular enlarged diameter anterior tract sheath having a tract sheath lumen extending between enlarged diameter anterior tract sheath proximal and distal ends and an enlarged diameter anterior tract sheath distal fixation mechanism adapted to attach said enlarged diameter anterior tract sheath to sacral bone;
inserting said enlarged diameter anterior tract sheath through said enlarged anterior tissue tract over said guidewire to position said enlarged diameter anterior tract sheath distal end against the anterior sacrum with the enlarged diameter anterior tract sheath lumen aligned axially with the visualized anterior axial instrumentation/fusion line;
operating said enlarged diameter anterior tract sheath distal fixation mechanism to attach said enlarged diameter anterior tract sheath to sacral bone with the enlarged diameter anterior tract sheath lumen aligned axially with the visualized anterior axial instrumentation/fusion line.

71. The method of claim 70, wherein the enlarged diameter anterior tract sheath fixation mechanism comprises distal screw threads encircling the enlarged diameter anterior tract sheath distal end adapted to be screwed into bone, and the step of affixing the enlarged diameter anterior tract sheath fixation mechanism to bone at the anterior target point comprises rotating the enlarged diameter anterior tract sheath body in a proximal section extending from the skin incision to screw the distal screw threads into sacral bone.

72. The method of claim 61, further comprising:
following the removal of the intermediate anterior tract sheath, dilating the tissue between the skin incision and the anterior target point around the guidewire attached to the cephalad end of the pilot hole to provide an enlarged anterior tract through between the skin incision and the anterior target point;
providing an enlarged diameter anterior tract sheath having a tract sheath lumen extending between enlarged diameter anterior tract sheath proximal and distal ends;
inserting said enlarged diameter anterior tract sheath through said enlarged anterior tissue tract over said guidewire to position said enlarged diameter anterior tract sheath distal end against the anterior sacrum with the enlarged diameter anterior tract sheath lumen aligned axially with the visualized anterior axial instrumentation/fusion line.

73. The method of claim 72, wherein the dilating step further comprises:
providing a tissue dilator having a dilator body of a dilation diameter and a dilator lumen having a dilator lumen diameter sized to receive the guidewire and extending between proximal and distal dilator body ends;
passing the dilator over the guidewire toward the anterior target point to dilate the tissue surrounding the guidewire body; and
withdrawing the tissue dilator from the guidewire body upon completion of dilation.

74. The method of claim 73, wherein:
the step of providing a tissue dilator comprises providing a plurality of tissue dilators each having a dilator body of a dilation diameter and a dilator lumen having a dilator lumen diameter sized to receive the guidewire and extending between proximal and distal dilator body ends; and
the steps of passing and withdrawing the tissue dilator, comprises repeatedly passing tissue dilators of increasing dilation diameter to progressively dilate tissue between the skin incision and the anterior target point.

75. The method of claim 73, further comprising:
providing an enlarged diameter tubular enlarged diameter anterior tract sheath having a tract sheath lumen

39 extending between enlarged diameter anterior tract sheath proximal and distal ends; and inserting said enlarged diameter anterior tract sheath through said enlarged anterior tissue tract over the dilator to position said enlarged diameter anterior tract sheath distal end against the anterior sacrum with the enlarged diameter anterior tract sheath lumen aligned axially with the visualized anterior axial instrumentation/fusion line.

76. The method of claim 72, wherein the dilating step further comprises:

providing a dilatation balloon catheter and tubular enlarged diameter anterior tract sheath;

with the guidewire aligned with the anterior axial instrumentation/fusion line, advancing the dilatation balloon catheter over the guidewire to locate a deflated balloon of the dilatation balloon catheter extending through presacral space;

expanding the deflated balloon to an expanded balloon diameter to dilate the presacral tissue between the anterior target point and the skin incision; and deflating and withdrawing the balloon catheter from the enlarged diameter anterior tract sheath lumen, whereby the enlarged diameter anterior tract sheath lumen provides the anterior, presacral, percutaneous tract through the patient's presacral space.

77. The method of claim 76, further comprising:

providing an enlarged diameter tubular enlarged diameter anterior tract sheath having a tract sheath lumen extending between enlarged diameter anterior tract sheath proximal and distal ends; and inserting said enlarged diameter anterior tract sheath through said enlarged anterior tissue tract over the expanded balloon to position said enlarged diameter anterior tract sheath distal end against the anterior sacrum with the enlarged diameter anterior tract sheath lumen aligned axially with the visualized anterior axial instrumentation/fusion line.

78. The method of claim 76, further comprising:

providing an enlarged diameter tubular enlarged diameter anterior tract sheath having a tract sheath lumen extending between enlarged diameter anterior tract sheath proximal and distal ends and an enlarged diameter anterior tract sheath distal fixation mechanism adapted to attach said enlarged diameter anterior tract sheath to sacral bone;

inserting said enlarged diameter anterior tract sheath through said enlarged anterior tissue tract over the expanded balloon to position said enlarged diameter anterior tract sheath distal end against the anterior sacrum with the enlarged diameter anterior tract sheath lumen aligned axially with the visualized anterior axial instrumentation/fusion line;

operating said enlarged diameter anterior tract sheath distal fixation mechanism to attach said enlarged diameter anterior tract sheath to sacral bone with the enlarged diameter anterior tract sheath lumen aligned axially with the visualized anterior axial instrumentation/fusion line; and deflating the balloon and withdrawing the balloon catheter and guidewire from the enlarged diameter anterior tract sheath lumen.

79. The method of claim 78, wherein the enlarged diameter anterior tract sheath fixation mechanism comprises distal screw threads encircling the enlarged diameter anterior tract sheath distal end adapted to be screwed into bone, and the operating step further comprises:

rotating the enlarged diameter anterior tract sheath body in a proximal section extending from the skin incision to screw the distal screw threads into sacral bone with the enlarged diameter anterior tract sheath lumen aligned axially with the visualized anterior axial instrumentation/fusion line.

80. A method of providing access to a series of adjacent vertebrae located within a human lumbar and sacral spine having an anterior aspect, a posterior aspect and an axial aspect, the vertebrae separated by intact or damaged spinal discs, the method comprising:

from a skin incision adjacent to the coccyx, forming an anterior, presacral, percutaneous tract through the patient's presacral space to access an anterior presacral position of a sacral vertebra in alignment with a visualized, anterior axial instrumentation/fusion line extending in said axial aspect through the series of adjacent vertebral bodies by:

expanding a percutaneous pathway through the patient's presacral space;

providing a tubular anterior tract sheath having a tract sheath axis and tract sheath lumen extending between proximal and distal tract sheath lumen ends; and advancing the anterior tract sheath distal end to said anterior presacral position with said tract sheath axis aligned axially with a sacral end of said visualized, anterior axial instrumentation/fusion line to form the anterior, presacral, percutaneous tract through the tubular anterior tract sheath aligned with the visualized anterior axial instrumentation/fusion line to provide working space and exposure of the anterior sacrum.

81. A method of providing access to a series of adjacent vertebrae located within a human lumbar and sacral spine having an anterior aspect, a posterior aspect and an axial aspect, the vertebrae separated by intact or damaged spinal discs, the method comprising:

from a skin incision adjacent to the coccyx, forming an anterior, presacral, percutaneous tract through the patient's presacral space to access an anterior presacral position of a sacral vertebra in alignment with a visualized, anterior axial instrumentation/fusion line extending in said axial aspect through the series of adjacent vertebral bodies by:

expanding a percutaneous pathway through the patient's presacral space;

providing an elongated guide member having a guide member axis extending between proximal and distal guide member ends and a guide member fixation mechanism at said guide member distal end;

advancing the guide member distal end to said anterior presacral position with said guide member axis aligned axially with a sacral end of said visualized, anterior axial instrumentation/fusion line; and fixing the guide member fixation mechanism to sacral bone at the anterior presacral position to form the anterior, presacral, percutaneous tract over the guide member aligned with the visualized anterior axial instrumentation/fusion line to provide working space and exposure of the anterior sacrum.

82. A surgical operating system for forming a percutaneous pathway from a skin incision generally axially aligned with a series of adjacent vertebrae located within a human lumbar and sacral spine having an anterior aspect, a posterior aspect and an axial aspect, the vertebrae separated by intact or damaged spinal discs, the system comprising:

guide means operable from a skin incision through a patient's skin and exposing a posterior, presacral position of a sacral vertebra in alignment with a visualized, curved, posterior axial instrumentation/fusion line extending in said axial aspect initially laterally through the sacral vertebra and then following the curvature of the spine through a series of adjacent cephalad vertebral bodies for accessing a posterior sacral position of a sacral vertebra that is aligned with the visualized, trans-sacral axial instrumentation/fusion line extending in said axial aspect through the series of adjacent vertebral bodies; and tract means defining a percutaneous tract having a tract axis aligned with said visualized, trans-sacral axial instrumentation/fusion line and extending from the skin incision to the accessed sacral position to facilitate surgical procedures aligned with said visualized, trans-sacral axial instrumentation/fusion line;

wherein the tract means comprises a tubular posterior tract sheath forming a posterior percutaneous tract through the patient's presacral space to access the posterior presacral position of a sacral vertebra in alignment with the visualized, anterior axial instrumentation/fusion line extending in said axial aspect through the series of adjacent vertebral bodies to enable boring a curved posterior axial bore extending along said posterior axial instrumentation/fusion line cephalad through the vertebral bodies of said series of adjacent vertebrae and any intervening spinal discs;

wherein the tubular posterior tract sheath has a tract sheath lumen extending between proximal and distal posterior tract sheath ends and a posterior tract sheath distal fixation mechanism adapted to attach said posterior tract sheath distal end to sacral bone with the posterior tract sheath lumen aligned axially with the visualized posterior axial instrumentation/fusion line;

wherein the posterior tract sheath fixation mechanism comprises distal screw threads encircling the tract sheath distal end adapted to be screwed into sacral bone.

83. A surgical operating system for forming a percutaneous pathway from a skin incision generally axially aligned with a series of adjacent vertebrae located within a human lumbar and sacral spine having an anterior aspect, a posterior aspect and an axial aspect, the vertebrae separated by intact or damaged spinal discs, the system comprising:

guide means operable from a skin incision through a patient's skin and exposing a posterior, presacral position of a sacral vertebra in alignment with a visualized, curved, posterior axial instrumentation/fusion line extending in said axial aspect initially laterally through the sacral vertebra and then following the curvature of the spine through a series of adjacent cephalad vertebral bodies for accessing a posterior sacral position of a sacral vertebra that is aligned with the visualized, trans-sacral axial instrumentation/fusion line extending in said axial aspect through the series of adjacent vertebral bodies;

tract means defining a percutaneous tract having a tract axis aligned with said visualized, trans-sacral axial instrumentation/fusion line and extending from the skin incision to the accessed sacral position to facilitate surgical procedures aligned with said visualized, trans-sacral axial instrumentation/fusion line; and means for drilling a pilot hole of a first diameter from said posterior presacral position along said axial instrumentation/fusion line within and axially through said series of vertebral bodies and intervening spinal discs to a cephalad pilot hole end within a vertebral body.

84. The system of claim 83, wherein the guide means comprises a guidewire having a guidewire body extending between a guidewire proximal end and a guidewire distal end having a guidewire fixation mechanism at the guidewire distal end adapted to be advanced into the pilot hole, affixed to vertebral bone at the cephalad end of the pilot hole, and aligned axially with the axial instrumentation/fusion line.

85. The system of claim 84, wherein the guide means comprises a guidewire having a guidewire body extending between a guidewire proximal end and a guidewire distal end having a guidewire fixation mechanism at the guidewire distal end adapted to be advanced to the posterior position, affixed to vertebral bone, and aligned axially with the axial instrumentation/fusion line.

86. The system of claim 83, wherein the tract means comprises a tubular posterior tract sheath forming a posterior percutaneous tract through the patient's presacral space to access the posterior presacral position of a sacral vertebra in alignment with the visualized, anterior axial instrumentation/fusion line extending in said axial aspect through the series of adjacent vertebral bodies to enable boring a curved posterior axial bore extending along said posterior axial instrumentation/fusion line cephalad through the vertebral bodies of said series of adjacent vertebrae and any intervening spinal discs.

87. The system of claim 86, wherein the tubular posterior tract sheath has a tract sheath lumen extending between proximal and distal posterior tract sheath ends and a posterior tract sheath distal fixation mechanism adapted to attach said posterior tract sheath distal end to sacral bone with the posterior tract sheath lumen aligned axially with the visualized posterior axial instrumentation/fusion line.

88. The system of claim 87, wherein the posterior tract sheath fixation mechanism comprises distal screw threads encircling the tract sheath distal end adapted to be screwed into sacral bone.

89. A surgical operating system for forming a percutaneous pathway from a skin incision generally axially aligned with a series of adjacent vertebrae located within a human lumbar and sacral spine having an anterior aspect, a posterior aspect and an axial aspect, the vertebrae separated by intact or damaged spinal discs, the system comprising:

a tubular member having a tubular member body extending between a tubular member body proximal end and a tubular member body distal end enclosing a tubular-member lumen and having a blunt tip at the tubular member body distal end, the tubular member adapted to be advanced through an incision made through the patient's skin adjacent to the coccyx and along the anterior surface of the sacrum under visualization until the blunt tip is at an anterior target point of a selected sacral vertebrae and the tubular member body is aligned with a visualized anterior axial instrumentation/fusion line extending in the cephalad direction through the series of adjacent vertebrae and extends percutaneously from the proximal tubular member end located outside the incision; and a guidewire extending between guidewire proximal and distal ends and having a guidewire distal fixation mechanism at the guidewire distal end sized to be fitted through the tubular member lumen to position the distal fixation mechanism at the anterior target point with the guidewire proximal end extending out of the tubular member lumen to manipulation of the guidewire to fix the distal fixation mechanism to the sacrum, whereby the tubular member can be withdrawn over the guidewire, leaving the guidewire attached to the anterior target point and extending through the presacral space and percutaneously in alignment with the anterior axial instrumentation/fusion line, whereby the attached guidewire provides a percutaneous tract for over the wire passage extending from the skin incision to the anterior target point and aligned with the visualized anterior axial instrumentation/fusion line.

90. The system of claim 89, further comprising a beveled-tip tract sheath having a beveled-tip sheath lumen and diameter extending between a beveled-tip sheath proximal end and distal bone engaging end, the beveled-tip sheath lumen adapted to receive the guidewire to enable the-beveled-tip sheath lumen to be inserted over the guidewire proximal end and through the presacral space in alignment with the visualized, anterior axial instrumentation/fusion line and the alignment of the distal bone engaging end of the beveled-tip sheath against the sacrum providing an anterior, presacral, percutaneous tract through the patient's presacral space to access the anterior presacral position of a sacral vertebra in alignment with the visualized, anterior axial instrumentation/fusion line extending in said axial aspect through the series of adjacent vertebral bodies.

91. The system of claim 89, further comprising means for drilling a pilot hole of a first diameter from said anterior presacral position along the visualized, anterior axial instrumentation/fusion line within and axially through said series of vertebral bodies and intervening spinal discs to a cephalad pilot hole end within a vertebral body.

92. The system of claim 91, further comprising:
  an intermediate anterior tract sheath having a tract sheath lumen extending between proximal and distal intermediate anterior tract sheath ends adapted to be inserted through said anterior tissue tract over said guidewire to position said distal intermediate anterior tract sheath distal end against the anterior sacrum with the intermediate anterior tract sheath lumen aligned axially with the visualized anterior axial instrumentation/fusion line; and
  a boring tool to bore a pilot hole in the cephalad direction through one or more vertebral body and intervening disc when inserted and advanced through the intermediate anterior tract sheath lumen to the anterior target point, whereby a pilot hole is bored in the cephalad direction through one or more vertebral body and intervening disc, if present, aligned with the visualized anterior axial instrumentation/fusion line.

93. The system of claim 89, further comprising a dilator adapted to dilate tissue surrounding the elongated guidewire to form an enlarged percutaneous tract that is aligned with the visualized, anterior axial instrumentation/fusion line.

94. The system of claim 93, further comprising an enlarged diameter tubular enlarged diameter anterior tract sheath having a tract sheath lumen extending between enlarged diameter anterior tract sheath proximal and distal ends and an enlarged diameter anterior tract sheath distal fixation mechanism adapted to attach said enlarged diameter anterior tract sheath to sacral bone, said enlarged diameter anterior tract sheath sized in sheath lumen diameter to be advanced through the dilated presacral space to position said enlarged diameter anterior tract sheath distal end against the anterior sacrum with the enlarged diameter anterior tract sheath lumen aligned axially with the visualized anterior axial instrumentation/fusion line, whereupon said enlarged diameter anterior tract sheath distal fixation mechanism is operable to attach said enlarged diameter anterior tract sheath to sacral bone with the enlarged diameter anterior tract sheath lumen aligned axially with the visualized, anterior axial instrumentation/fusion line, whereby the attached enlarged diameter anterior tract sheath lumen provides a percutaneous tract for over the wire passage extending from the skin incision to the anterior target point and aligned with the visualized anterior axial instrumentation/fusion line.

95. A surgical operating system for forming a percutaneous pathway from a skin incision generally axially aligned with a series of adjacent vertebrae located within a human lumbar and sacral spine having an anterior aspect, a posterior aspect and an axial aspect, the vertebrae separated by intact or damaged spinal discs, the system comprising:
  a tubular member having a tubular member body extending between a tubular member body proximal end and a tubular member body distal end enclosing a tubular member lumen and having a blunt tip at the tubular member body distal end, the tubular member adapted to be advanced through an incision made through the patient's skin adjacent to the coccyx and along the anterior surface of the sacrum under visualization until the blunt tip is at an anterior target point of a selected sacral vertebrae and the tubular member body is aligned with a visualized anterior axial instrumentation/fusion line extending in the cephalad direction through the series of adjacent vertebrae and extends percutaneously from the proximal tubular member end located outside the incision;
  a guidewire extending between guidewire proximal and distal ends and having a guidewire distal fixation mechanism at the guidewire distal end sized to be fitted through the tubular member lumen to position the distal fixation mechanism at the anterior target point with the guidewire proximal end extending out of the tubular member lumen to manipulation of the guidewire to fix the distal fixation mechanism to the sacrum, whereby the tubular member can be withdrawn over the guidewire, leaving the guidewire attached to the anterior target point and extending through the presacral space and percutaneously in alignment with the anterior axial instrumentation/fusion line, whereby the attached guidewire provides a percutaneous tract for over the wire passage extending from the skin incision to the anterior target point and aligned with the visualized anterior axial instrumentation/fusion line; and
  a threaded-tip tract sheath having a threaded-tip sheath lumen and diameter and a threaded sheath proximal end and a threaded sheath distal bone engaging end, the thread-tipped sheath lumen adapted to receive the guidewire to enable the thread-tipped sheath lumen to be inserted over the guidewire proximal end and through the presacral space in alignment with the visualized anterior axial instrumentation/fusion line and the engagement of the distal bone engaging end of the thread-tipped sheath into the sacrum providing an anterior, presacral, percutaneous tract through the patient's presacral space to access the anterior presacral position of a sacral vertebra in alignment with the visualized, straight axial instrumentation/fusion line extending in said axial aspect through the series of adjacent vertebral bodies.

96. The system of claim 95, further comprising a dilator adapted to dilate tissue surrounding the elongated guidewire to form an enlarged percutaneous tract that is aligned with the visualized, anterior axial instrumentation/fusion line.

97. The system of claim 96, further comprising an enlarged diameter tubular enlarged diameter anterior tract sheath having a tract sheath lumen extending between enlarged diameter anterior tract sheath proximal and distal ends and an enlarged diameter anterior tract sheath distal fixation mechanism adapted to attach said enlarged diameter anterior tract sheath to sacral bone, said enlarged diameter anterior tract sheath sized in sheath lumen diameter to be advanced through the dilated presacral space to position said enlarged diameter anterior tract sheath distal end against the anterior sacrum with the enlarged diameter anterior tract sheath lumen aligned axially with the visualized anterior axial instrumentation/fusion line, whereupon said enlarged diameter anterior tract sheath distal fixation mechanism is operable to attach said enlarged diameter anterior tract sheath to sacral bone with the enlarged diameter anterior tract sheath lumen aligned axially with the visualized, anterior axial instrumentation/fusion line, whereby the attached enlarged diameter anterior tract sheath lumen provides a percutaneous tract for over the wire passage extending from the skin incision to the anterior target point and aligned with the visualized anterior axial instrumentation/fusion line.

98. The system of claim 97, wherein the enlarged diameter anterior tract sheath fixation mechanism comprises distal screw threads encircling the enlarged diameter anterior tract sheath distal end adapted to be screwed into bone at the anterior target point by rotating the enlarged diameter anterior tract sheath body in a proximal section extending from the skin incision to screw the distal screw threads into sacral bone.

99. The system of claim 96, wherein the dilator further comprises:
   a first tissue dilator having a dilator body of a dilation diameter and a dilator lumen having a dilator lumen diameter sized to receive the guidewire and extending between proximal and distal first tissue dilator body ends, the first tissue dilator is adapted to be advanced over the guidewire toward the anterior target point to dilate the tissue surrounding the guidewire body; and
   a second tissue dilator having a dilator body of a dilation diameter and a dilator lumen having a dilator lumen diameter sized to receive the first tissue dilator body and extending between proximal and distal second tissue dilator body ends, the second tissue dilator adapted to be advanced over first tissue dilator and the guidewire toward the anterior target point to further dilate the tissue surrounding the guidewire body.

100. The system of claim 96, wherein the dilator further comprises:
   a dilatation balloon catheter having an expandable balloon and a balloon catheter lumen extending between balloon catheter proximal and distal ends, the dilatation balloon catheter adapted to be advanced over the guidewire within the catheter lumen to locate the deflated balloon of the dilatation balloon catheter extending through presacral space; and
   means for expanding the deflated balloon to an expanded balloon diameter to dilate the presacral tissue between the anterior target point and the skin incision and deflating and withdrawing the balloon catheter from the enlarged diameter anterior tract sheath lumen, whereby the enlarged diameter anterior tract sheath lumen provides the anterior, presacral, percutaneous tract through the patient's presacral space.

101. A surgical operating system for forming a percutaneous pathway from a skin incision generally axially aligned with a series of adjacent vertebrae located within a human lumbar and sacral spine having an anterior aspect, a posterior aspect and an axial aspect, the vertebrae separated by intact or damaged spinal discs, the system comprising:
   a tubular member having a tubular member body extending between a tubular member body proximal end and a tubular member body distal end enclosing a tubular member lumen and having a blunt tip at the tubular member body distal end, the tubular member adapted to be advanced through an incision made through the patient's skin adjacent to the coccyx and along the anterior surface of the sacrum under visualization until the blunt tip is at an anterior target point of a selected sacral vertebrae and the tubular member body is aligned with a visualized anterior axial instrumentation/fusion line extending in the cephalad direction through the series of adjacent vertebrae and extends percutaneously from the proximal tubular member end located outside the incision;
   a guidewire extending between guidewire proximal and distal ends and having a guidewire distal fixation mechanism at the guidewire distal end sized to be fitted through the tubular member lumen to position the distal fixation mechanism at the anterior target point with the guidewire proximal end extending out of the tubular member lumen to manipulation of the guidewire to fix the distal fixation mechanism to the sacrum, whereby the tubular member can be withdrawn over the guidewire, leaving the guidewire attached to the anterior target point and extending through the presacral space and percutaneously in alignment with the anterior axial instrumentation/fusion line, whereby the attached guidewire provides a percutaneous tract for over the wire passage extending from the skin incision to the anterior target point and aligned with the visualized anterior axial instrumentation/fusion line;
   a dilator adapted to dilate tissue surrounding the elongated guidewire to form an enlarged percutaneous tract that is aligned with the visualized, anterior axial instrumentation/fusion line; and
   an enlarged diameter tubular enlarged diameter anterior tract sheath having a tract sheath lumen extending between enlarged diameter anterior tract sheath proximal and distal ends and an enlarged diameter anterior tract sheath distal fixation mechanism adapted to attach said enlarged diameter anterior tract sheath to sacral bone, said enlarged diameter anterior tract sheath sized in sheath lumen diameter to be advanced through the dilated presacral space to position said enlarged diameter anterior tract sheath distal end against the anterior sacrum with the enlarged diameter anterior tract sheath lumen aligned axially with the visualized anterior axial instrumentation/fusion line, whereupon said enlarged diameter anterior tract sheath distal fixation mechanism is operable to attach said enlarged diameter anterior tract sheath to sacral bone with the enlarged diameter anterior tract sheath lumen aligned axially with the visualized, anterior axial instrumentation/fusion line, whereby the attached enlarged diameter anterior tract sheath lumen provides a percutaneous tract for over the wire passage extending from the skin incision to the anterior target point and aligned with the visualized anterior axial instrumentation/fusion line;
   wherein the enlarged diameter anterior tract sheath fixation mechanism comprises distal screw threads encircling the enlarged diameter anterior tract sheath distal end adapted to be screwed into bone at the anterior target point by rotating the enlarged diameter anterior tract sheath body in a proximal section extending from the skin incision to screw the distal screw threads into sacral bone.

102. A surgical operating system for forming a percutaneous pathway from a skin incision generally axially aligned with a series of adjacent vertebrae located within a human lumbar and sacral spine having an anterior aspect, a posterior aspect and an axial aspect, the vertebrae separated by intact or damaged spinal discs, the system comprising:

a tubular member having a tubular member body extending between a tubular member body proximal end and a tubular member body distal end enclosing a tubular member lumen and having a blunt tip at the tubular member body distal end, the tubular member adapted to be advanced through an incision made through the patient's skin adjacent to the coccyx and along the anterior surface of the sacrum under visualization until the blunt tip is at an anterior target point of a selected sacral vertebrae and the tubular member body is aligned with a visualized anterior axial instrumentation/fusion line extending in the cephalad direction through the series of adjacent vertebrae and extends percutaneously from the proximal tubular member end located outside the incision;

a guidewire extending between guidewire proximal and distal ends and having a guidewire distal fixation mechanism at the guidewire distal end sized to be fitted through the tubular member lumen to position the distal fixation mechanism at the anterior target point with the guidewire proximal end extending out of the tubular member lumen to manipulation of the guidewire to fix the distal fixation mechanism to the sacrum, whereby the tubular member can be withdrawn over the guidewire, leaving the guidewire attached to the anterior target point and extending through the presacral space and percutaneously in alignment with the anterior axial instrumentation/fusion line, whereby the attached guidewire provides a percutaneous tract for over the wire passage extending from the skin incision to the anterior target point and aligned with the visualized anterior axial instrumentation/fusion line; and a dilator adapted to dilate tissue surrounding the elongated guidewire to form an enlarged percutaneous tract that is aligned with the visualized, anterior axial instrumentation/fusion line;

wherein the dilator further comprises:

a first tissue dilator having a dilator body of a dilation diameter and a dilator lumen having a dilator lumen diameter sized to receive the guidewire and extending between proximal and distal first tissue dilator body ends, the first tissue dilator is adapted to be advanced over the guidewire toward the anterior target point to dilate the tissue surrounding the guidewire body; and a second tissue dilator having a dilator body of a dilation diameter and a dilator lumen having a dilator lumen diameter sized to receive the first tissue dilator body and extending between proximal and distal second tissue dilator body ends, the second tissue dilator adapted to be advanced over first tissue dilator and the guidewire toward the anterior target point to further dilate the tissue surrounding the guidewire body.

103. A surgical operating system for forming a percutaneous pathway from a skin incision generally axially aligned with a series of adjacent vertebrae located within a human lumbar and sacral spine having an anterior aspect, a posterior aspect and an axial aspect, the vertebrae separated by intact or damaged spinal discs, the system comprising:

a tubular member having a tubular member body extending between a tubular member body proximal end and a tubular member body distal end enclosing a tubular member lumen and having a blunt tip at the tubular member body distal end, the tubular member adapted to be advanced through an incision made through the patient's skin adjacent to the coccyx and along the anterior surface of the sacrum under visualization until the blunt tip is at an anterior target point of a selected sacral vertebrae and the tubular member body is aligned with a visualized anterior axial instrumentation/fusion line extending in the cephalad direction through the series of adjacent vertebrae and extends percutaneously from the proximal tubular member end located outside the incision;

a guidewire extending between guidewire proximal and distal ends and having a guidewire distal fixation mechanism at the guidewire distal end sized to be fitted through the tubular member lumen to position the distal fixation mechanism at the anterior target point with the guidewire proximal end extending out of the tubular member lumen to manipulation of the guidewire to fix the distal fixation mechanism to the sacrum, whereby the tubular member can be withdrawn over the guidewire, leaving the guidewire attached to the anterior target point and extending through the presacral space and percutaneously in alignment with the anterior axial instrumentation/fusion line, whereby the attached guidewire provides a percutaneous tract for over the wire passage extending from the skin incision to the anterior target point and aligned with the visualized anterior axial instrumentation/fusion line; and a dilator adapted to dilate tissue surrounding the elongated guidewire to form an enlarged percutaneous tract that is aligned with the visualized, anterior axial instrumentation/fusion line;

wherein the dilator further comprises:

a dilatation balloon catheter having an expandable balloon and a balloon catheter lumen extending between balloon catheter proximal and distal ends, the dilatation balloon catheter adapted to be advanced over the guidewire within the catheter lumen to locate the deflated balloon of the dilatation balloon catheter extending through presacral space; and means for expanding the deflated balloon to an expanded balloon diameter to dilate the presacral tissue between the anterior target point and the skin incision and deflating and withdrawing the balloon catheter from the enlarged diameter anterior tract sheath lumen, whereby the enlarged diameter anterior tract sheath lumen provides the anterior, presacral, percutaneous tract through the patient's presacral space.

104. A surgical operating system for forming a percutaneous pathway from a skin incision generally axially aligned with a series of adjacent vertebrae located within a human lumbar and sacral spine having an anterior aspect, a posterior aspect and an axial aspect, the vertebrae separated by intact or damaged spinal discs, the system comprising:

an elongated occluder extending between a proximal occluder end and a distal, blunt-tip, occluder end;

a tubular member having a tubular member body extending between a tubular member body proximal end and a tubular member body distal end enclosing a tubular member lumen and having a tubular member distal fixation mechanism at the tubular member body distal end, the occluder adapted and sized to be inserted through the tubular member lumen to form a guide assembly with the distal blunt-tip occluder end projecting distally from the tubular member distal fixation mechanism thereby providing a guide assembly distal end with the tubular member distal fixation mechanism retracted to prevent catching on body tissue, the guide assembly adapted to be advanced through an incision made through the patient's skin adjacent to the coccyx aligned with a visualized, anterior axial instrumentation/fusion line and along the anterior surface of the sacrum under visualization until the blunt tip is at an anterior target point of a selected sacral vertebrae and the tubular member body is aligned with the visualized, anterior axial instrumentation/fusion line and extends percutaneously from the proximal tubular member end located outside the incision, whereby the tubular member is adapted to be advanced distally past the distal, blunt tip, occluder end and fixed to sacral bone enabling retention of the tubular member in axial alignment with the visualized, anterior axial instrumentation/fusion line, whereby the attached tubular member provides a percutaneous tract for over the wire passage extending from the skin incision to the anterior target point and aligned with the visualized anterior axial instrumentation/fusion line.

105. The system of claim 104, further comprising a dilator adapted to dilate tissue surrounding the elongated tubular member to form an enlarged percutaneous tract that is aligned with the visualized, anterior axial instrumentation/fusion line.

106. The system of claim 105, further comprising an enlarged diameter tubular enlarged diameter anterior tract sheath having a tract sheath lumen extending between enlarged diameter anterior tract sheath proximal and distal ends and an enlarged diameter anterior tract sheath distal fixation mechanism adapted to attach said enlarged diameter anterior tract sheath to sacral bone, said enlarged diameter anterior tract sheath sized in sheath lumen diameter to be advanced through the dilated presacral space to position said enlarged diameter anterior tract sheath distal end against the anterior sacrum with the enlarged diameter anterior tract sheath lumen aligned axially with the visualized anterior axial instrumentation/fusion line, whereupon said enlarged diameter anterior tract sheath distal fixation mechanism is operable to attach said enlarged diameter anterior tract sheath to sacral bone with the enlarged diameter anterior tract sheath lumen aligned axially with the visualized, anterior axial instrumentation/fusion line.

107. The system of claim 105, wherein the dilator further comprises:

a first tissue dilator having a dilator body of a dilation diameter and a dilator lumen having a dilator lumen diameter sized to receive the tubular member and extending between proximal and distal first tissue dilator body ends, the first tissue dilator is adapted to be advanced over the tubular member toward the anterior target point to dilate the tissue surrounding the tubular member body; and a second tissue dilator having a dilator body of a dilation diameter and a dilator lumen having a dilator lumen diameter sized to receive the first tissue dilator body and extending between proximal and distal second tissue dilator body ends, the second tissue dilator adapted to be advanced over first tissue dilator and the tubular member toward the anterior target point to further dilate the tissue surrounding the tubular member body.

108. A surgical operating system for forming a percutaneous pathway from a skin incision generally axially aligned with a series of adjacent vertebrae located within a human lumbar and sacral spine having an anterior aspect, a posterior aspect and an axial aspect, the vertebrae separated by intact or damaged spinal discs, the system comprising:

an elongated occluder extending between a proximal occluder end and a distal, blunt-tip, occluder end;

a tubular member having a tubular member body extending between a tubular member body proximal end and a tubular member body distal end enclosing a tubular member lumen and having a tubular member distal fixation mechanism at the tubular member body distal end, the occluder adapted and sized to be inserted through the tubular member lumen to form a guide assembly with the distal blunt-tip occluder end projecting distally from the tubular member distal fixation mechanism thereby providing a guide assembly distal end with the tubular member distal fixation mechanism retracted to prevent catching on body tissue, the guide assembly adapted to be advanced through an incision made through the patient's skin adjacent to the coccyx aligned with a visualized, anterior axial instrumentation/fusion line and along the anterior surface of the sacrum under visualization until the blunt tip is at an anterior target point of a selected sacral vertebrae and the tubular member body is aligned with the visualized, anterior axial instrumentation/fusion line and extends percutaneously from the proximal tubular member end located outside the incision, whereby the tubular member is adapted to be advanced distally past the distal, blunt tip, occluder end and fixed to sacral bone enabling retention of the tubular member in axial alignment with the visualized, anterior axial instrumentation/fusion line, whereby the attached tubular member provides a percutaneous tract for over the wire passage extending from the skin incision to the anterior target point and aligned with the visualized anterior axial instrumentation/fusion line; and a threaded-tip tract sheath having a threaded-tip sheath lumen and diameter and a threaded sheath proximal end and a threaded sheath distal bone engaging end, the thread-tipped sheath lumen adapted to receive the tubular member to enable the thread-tipped sheath lumen to be inserted over the tubular member proximal end and through the presacral space in alignment with the visualized anterior axial instrumentation/fusion line and the engagement of the distal bone engaging end of the thread-tipped sheath into the sacrum providing an anterior, presacral, percutaneous tract through the patient's presacral space to access the anterior presacral position of a sacral vertebra in alignment with the visualized, straight axial instrumentation/fusion line extending in said axial aspect through the series of adjacent vertebral bodies.

109. The system of claim 108, further comprising a beveled-tip tract sheath having a beveled-tip sheath lumen and diameter extending between a beveled-tip sheath proximal end and distal bone engaging end, the beveled-tip sheath lumen adapted to receive the tubular member to enable the beveled-tip sheath lumen to be inserted over the tubular member proximal end and through the presacral space in alignment with the visualized, anterior axial instrumentation/fusion line and the alignment of the distal bone engaging end of the beveled-tip sheath against the sacrum providing an anterior, presacral, percutaneous tract through the patient's presacral space to access the anterior presacral position of a sacral vertebra in alignment with the visualized, anterior axial instrumentation/fusion line extending in said axial aspect through the series of adjacent vertebral bodies.

110. The system of claim 108, further comprising a dilator adapted to dilate tissue surrounding the elongated tubular member to form an enlarged percutaneous tract that is aligned with the visualized, anterior axial instrumentation/fusion line.

111. The system of claim 110, further comprising an enlarged diameter tubular enlarged diameter anterior tract sheath having a tract sheath lumen extending between enlarged diameter anterior tract sheath proximal and distal ends and an enlarged diameter anterior tract sheath distal fixation mechanism adapted to attach said enlarged diameter anterior tract sheath to sacral bone, said enlarged diameter anterior tract sheath sized in sheath lumen diameter to be advanced through the dilated presacral space to position said enlarged diameter anterior tract sheath distal end against the anterior sacrum with the enlarged diameter anterior tract sheath lumen aligned axially with the visualized anterior axial instrumentation/fusion line, whereupon said enlarged diameter anterior tract sheath distal fixation mechanism is operable to attach said enlarged diameter anterior tract sheath to sacral bone with the enlarged diameter anterior tract sheath lumen aligned axially with the visualized, anterior axial instrumentation/fusion line.

112. The system of claim 111, wherein the enlarged diameter anterior tract sheath fixation mechanism comprises distal screw threads encircling the enlarged diameter anterior tract sheath distal end adapted to be screwed into bone at the anterior target point by rotating the enlarged diameter anterior tract sheath body in a proximal section extending from the skin incision to screw the distal screw threads into sacral bone.

113. The system of claim 110, wherein the dilator further comprises:
  a dilatation balloon catheter having an expandable balloon and a balloon catheter lumen extending between balloon catheter proximal and distal ends, the dilatation balloon catheter adapted to be advanced over the tubular member within the catheter lumen to locate the deflated balloon of the dilatation balloon catheter extending through presacral space; and
  means for expanding the deflated balloon to an expanded balloon diameter to dilate the presacral tissue between the anterior target point and the skin incision and deflating and withdrawing the balloon catheter from the enlarged diameter anterior tract sheath lumen, whereby the enlarged diameter anterior tract sheath lumen provides the anterior, presacral, percutaneous tract through the patient's presacral space.

114. A surgical operating system for forming a percutaneous pathway from a skin incision generally axially aligned with a series of adjacent vertebrae located within a human lumbar and sacral spine having an anterior aspect, a posterior aspect and an axial aspect, the vertebrae separated by intact or damaged spinal discs, the system comprising:
  an elongated occluder extending between a proximal occluder end and a distal, blunt-tip, occluder end;
  a tubular member having a tubular member body extending between a tubular member body proximal end and a tubular member body distal end enclosing a tubular member lumen and having a tubular member distal fixation mechanism at the tubular member body distal end, the occluder adapted and sized to be inserted through the tubular member lumen to form a guide assembly with the distal blunt-tip occluder end projecting distally from the tubular member distal fixation mechanism thereby providing a guide assembly distal end with the tubular member distal fixation mechanism retracted to prevent catching on body tissue, the guide assembly adapted to be advanced through an incision made through the patient's skin adjacent to the coccyx aligned with a visualized, anterior axial instrumentation/fusion line and along the anterior surface of the sacrum under visualization until the blunt tip is at an anterior target point of a selected sacral vertebrae and the tubular member body is aligned with the visualized, anterior axial instrumentation/fusion line and extends percutaneously from the proximal tubular member end located outside the incision, whereby the tubular member is adapted to be advanced distally past the distal, blunt tip, occluder end and fixed to sacral bone enabling retention of the tubular member in axial alignment with the visualized, anterior axial instrumentation/fusion line, whereby the attached tubular member provides a percutaneous tract for over the wire passage extending from the skin incision to the anterior target point and aligned with the visualized anterior axial instrumentation/fusion line; and a beveled-tip tract sheath having a beveled-tip sheath lumen and diameter extending between a beveled-tip sheath proximal end and distal bone engaging end, the beveled-tip sheath lumen adapted to receive the tubular member to enable the beveled-tip sheath lumen to be inserted over the tubular member proximal end and through the presacral space in alignment with the visualized, anterior axial instrumentation/fusion line and the alignment of the distal bone engaging end of the beveled-tip sheath against the sacrum providing an anterior, presacral, percutaneous tract through the patient's presacral space to access the anterior presacral position of a sacral vertebra in alignment with the visualized, anterior axial instrumentation/fusion line extending in said axial aspect through the series of adjacent vertebral bodies.

115. The system of claim 114, further comprising a dilator adapted to dilate tissue surrounding the elongated tubular member to form an enlarged percutaneous tract that is aligned with the visualized, anterior axial instrumentation/fusion line.

116. The system of claim 115, further comprising an enlarged diameter tubular enlarged diameter anterior tract sheath having a tract sheath lumen extending between enlarged diameter anterior tract sheath proximal and distal ends and an enlarged diameter anterior tract sheath distal fixation mechanism adapted to attach said enlarged diameter anterior tract sheath to sacral bone, said enlarged diameter anterior tract sheath sized in sheath lumen diameter to be advanced through the dilated presacral space to position said enlarged diameter anterior tract sheath distal end against the anterior sacrum with the enlarged diameter anterior tract sheath lumen aligned axially with the visualized anterior axial instrumentation/fusion line, whereupon said enlarged diameter anterior tract sheath distal fixation mechanism is operable to attach said enlarged diameter anterior tract sheath to sacral bone with the enlarged diameter anterior tract sheath lumen aligned axially with the visualized, anterior axial instrumentation/fusion line.

117. The system of claim 116 wherein the enlarged diameter anterior tract sheath fixation mechanism comprises distal screw threads encircling the enlarged diameter anterior tract sheath distal end adapted to be screwed into bone at the anterior target point by rotating the enlarged diameter anterior tract sheath body in a proximal section extending from the skin incision to screw the distal screw threads into sacral bone.

118. The system of claim 115, wherein the dilator further comprises:

a dilatation balloon catheter having an expandable balloon and a balloon catheter lumen extending between balloon catheter proximal and distal ends, the dilatation balloon catheter adapted to be advanced over the tubular member within the catheter lumen to locate the deflated balloon of the dilatation balloon catheter extending through presacral space; and means for expanding the deflated balloon to an expanded balloon diameter to dilate the presacral tissue between the anterior target point and the skin incision and deflating and withdrawing the balloon catheter from the enlarged diameter anterior tract sheath lumen, whereby the enlarged diameter anterior tract sheath lumen provides the anterior presacral, percutaneous tract through the patient's presacral space.

119. A surgical operating system for forming a percutaneous pathway from a skin incision generally axially aligned with a series of adjacent vertebrae located within a human lumbar and sacral spine having an anterior aspect, a posterior aspect and an axial aspect, the vertebrae separated by intact or damaged spinal discs, the system comprising:

an elongated occluder extending between a proximal occluder end and a distal, blunt-tip, occluder end;

a tubular member having a tubular member body extending between a tubular member body proximal end and a tubular member body distal end enclosing a tubular member lumen and having a tubular member distal fixation mechanism at the tubular member body distal end, the occluder adapted and sized to be inserted through the tubular member lumen to form a guide assembly with the distal blunt-tip occluder end projecting distally from the tubular member distal fixation mechanism thereby providing a guide assembly distal end with the tubular member distal fixation mechanism retracted to prevent catching on body tissue, the guide assembly adapted to be advanced through an incision made through the patient's skin adjacent to the coccyx aligned with a visualized, anterior axial instrumentation/fusion line and along the anterior surface of the sacrum under visualization until the blunt tip is at an anterior target point of a selected sacral vertebrae and the tubular member body is aligned with the visualized, anterior axial instrumentation/fusion line and extends percutaneously from the proximal tubular member end located outside the incision, whereby the tubular member is adapted to be advanced distally past the distal, blunt tip, occluder end and fixed to sacral bone enabling retention of the tubular member in axial alignment with the visualized, anterior axial instrumentation/fusion line, whereby the attached tubular member provides a percutaneous tract for over the wire passage extending from the skin incision to the anterior target point and aligned with the visualized anterior axial instrumentation/fusion line;

a dilator adapted to dilate tissue surrounding the elongated tubular member to form an enlarged percutaneous tract that is aligned with the visualized, anterior axial instrumentation/fusion line; and an enlarged diameter tubular enlarged diameter anterior tract sheath having a tract sheath lumen extending between enlarged diameter anterior tract sheath proximal and distal ends and an enlarged diameter anterior tract sheath distal fixation mechanism adapted to attach said enlarged diameter anterior tract sheath to sacral bone, said enlarged diameter anterior tract sheath sized in sheath lumen diameter to be advanced through the dilated presacral space to position said enlarged diameter anterior tract sheath distal end against the anterior sacrum with the enlarged diameter anterior tract sheath lumen aligned axially with the visualized anterior axial instrumentation/fusion line, whereupon said enlarged diameter anterior tract sheath distal fixation mechanism is operable to attach said enlarged diameter anterior tract sheath to sacral bone with the enlarged diameter anterior tract sheath lumen aligned axially with the visualized, anterior axial instrumentation/fusion line;

wherein the enlarged diameter anterior tract sheath fixation mechanism comprises distal screw threads encircling the enlarged diameter anterior tract sheath distal end adapted to be screwed into bone at the anterior target point by rotating the enlarge diameter anterior tract sheath body in a proximal section extending from the skin incision to screw the distal screw threads into sacral bone.

120. The system of claim 119, wherein the dilator further comprises:

a dilatation balloon catheter having an expandable balloon and a balloon catheter lumen extending between balloon catheter proximal and distal ends, the dilatation balloon catheter adapted to be advanced over the tubular member within the catheter lumen to locate the deflated balloon of the dilatation balloon catheter extending through presacral space; and means for expanding the deflated balloon to an expanded balloon diameter to dilate the presacral tissue between the anterior target point and the skin incision and deflating and withdrawing the balloon catheter from the enlarged diameter anterior tract sheath lumen, whereby the enlarged diameter anterior tract sheath lumen provides the anterior, presacral, percutaneous tract through the patient's presacral space.

121. A surgical operating system for forming a percutaneous pathway from a skin incision generally axially aligned with a series of adjacent vertebrae located within a human lumbar and sacral spine having an anterior aspect, a posterior aspect and an axial aspect, the vertebrae separated by intact or damaged spinal discs, the system comprising:

an elongated occluder extending between a proximal occluder end and a distal, blunt-tip, occluder end;

a tubular member having a tubular member body extending between a tubular member body proximal end and a tubular member body distal end enclosing a tubular member lumen and having a tubular member distal fixation mechanism at the tubular member body distal end, the occluder adapted and sized to be inserted through the tubular member lumen to form a guide assembly with the distal blunt-tip occluder end projecting distally from the tubular member distal fixation mechanism thereby providing a guide assembly distal end with the tubular member distal fixation mechanism retracted to prevent catching on body tissue, the guide assembly adapted to be advanced through an incision made through the patient's skin adjacent to the coccyx aligned with a visualized, anterior axial instrumentation/fusion line and along the anterior surface of the sacrum under visualization until the blunt tip is at an anterior target point of a selected sacral vertebrae and the tubular member body is aligned with the visualized, anterior axial instrumentation/fusion line and extends percutaneously from the proximal tubular member end located outside the incision, whereby the tubular member is adapted to be advanced distally past the distal, blunt tip, occluder end and fixed to sacral bone enabling retention of the tubular member in axial alignment with the visualized, anterior axial instrumentation/fusion line, whereby the attached tubular member provides a percutaneous tract for over the wire passage extending from the skin incision to the anterior target point and aligned with the visualized anterior axial instrumentation/fusion line; and a dilator adapted to dilate tissue surrounding the elongated tubular member to form an enlarged percutaneous tract that is aligned with the visualized, anterior axial instrumentation/fusion line;

wherein the dilator further comprises:

a dilatation balloon catheter having an expandable balloon and a balloon catheter lumen extending between balloon catheter proximal and distal ends, the dilatation balloon catheter adapted to be advanced over the tubular member within the catheter lumen to locate the deflated balloon of the dilatation balloon catheter extending through presacral space; and means for expanding the deflated balloon to an expanded balloon diameter to dilate the presacral tissue between the anterior target point and the skin incision and deflating and withdrawing the balloon catheter from the enlarged diameter anterior tract sheath lumen, whereby the enlarged diameter anterior tract sheath lumen provides the anterior, presacral, percutaneous tract through the patient's presacral space.

122. A surgical operating system for forming a percutaneous pathway from a skin incision generally axially aligned with a series of adjacent vertebrae located within a human lumbar and sacral spine having an anterior aspect, a posterior aspect and an axial aspect, the vertebrae separated by intact or damaged spinal discs and boring a trans-sacral axial instrumentation/fusion bore through the sacrum and into at least one vertebrae and any intervertebral disc in alignment with a visualized, trans-sacral axial instrumentation/fusion line, the system comprising:

a guide member extending between guide member proximal and distal ends that is adapted to be inserted through the skin incision and advanced through presacral space along the anterior surface of the sacrum to the anterior target point and axially aligned with a visualized, trans-sacral axial fusion/instrumentation line extending in said axial aspect through a series of adjacent vertebral bodies;

an anterior percutaneous tract forming member extending between tract forming member proximal and distal ends adapted to be inserted through the skin incision and advanced through presacral space along said guide member; and a boring tool adapted to be advanced to said anterior target point through said percutaneous tract to bore a trans-sacral axial instrumentation/fusion bore through the sacrum and into at least one vertebrae and any intervertebral disc in alignment with said visualized, trans-sacral axial instrumentation/fusion line.

123. The surgical operating system of claim 122, wherein said guide member further comprises a distal fixation mechanism adapted to be fixed to the anterior surface of the sacrum at the anterior target point.

124. The surgical operating system of claim 122, wherein said anterior percutaneous tract forming member further comprises a distal fixation mechanism adapted to be fixed to the anterior surface of the sacrum at the anterior target point.

125. The surgical operating system of claim 122, wherein said guide member further comprises a guide assembly that further comprises:

an elongated tubular member having a tubular member body enclosing a tubular member lumen extending between a tubular member proximal end and a tubular member distal end; and an elongated occluder having an occluder body extending between an occluder proximal end and an occluder distal end that is adapted to be inserted through the tubular member lumen; and wherein at least one of the tubular member distal end and the occluder distal end is blunted and the other of the tubular member distal end and the occluder distal end further comprises a distal fixation mechanism adapted to be fixed to the anterior surface of the sacrum at the anterior target point.

126. A surgical operating system for forming a percutaneous pathway from a skin incision generally axially aligned with a series of adjacent vertebrae located within a human lumbar and sacral spine having an anterior aspect, a posterior aspect and an axial aspect, the vertebrae separated by intact or damaged spinal discs and boring a trans-sacral axial instrumentation/fusion bore through the sacrum and into at least one vertebrae and any intervertebral disc in alignment with a visualized, trans-sacral axial instrumentation/fusion line, the system comprising:

a guide assembly that further comprises:

an elongated tubular member having a tubular member body enclosing a tubular member lumen extending between a tubular member proximal end and a tubular member distal end; and an elongated occluder having an occluder body extending between an occluder proximal end and an occluder distal end that is adapted to be inserted through the tubular member lumen;

wherein at least one of the tubular member distal end and the occluder distal end is blunted and the other of the tubular member distal end and the occluder distal end further comprises a distal fixation mechanism adapted to be fixed to the anterior surface of the sacrum at the anterior target point, whereby the one of the elongated occluder or tubular member having the distal fixation mechanism attached to the anterior surface of the sacrum at the anterior target point forms an anterior percutaneous tract through presacral space; and a boring tool adapted to be advanced to said anterior target point through said percutaneous tract to bore a trans-sacral axial instrumentation/fusion bore through the sacrum and into at least one vertebrae and any intervertebral disc in alignment with said visualized, trans-sacral axial instrumentation/fusion line.

127. A surgical operating system for forming a percutaneous pathway from a skin incision generally axially aligned with a series of adjacent vertebrae located within a human lumbar and sacral spine having an anterior aspect, a posterior aspect and an axial aspect, the vertebrae separated by intact or damaged spinal discs, the system comprising:

a guide assembly that further comprises:

an elongated tubular member having a tubular member body enclosing a tubular member lumen extending between a tubular member proximal end and a tubular member distal end; and an elongated occluder having an occluder body extending between an occluder proximal end and an occluder distal end that is adapted to be inserted through the tubular member lumen;

wherein at least one of the tubular member distal end and the occluder distal end is blunted and the other of the tubular member distal end and the occluder distal end further comprises a distal fixation mechanism adapted to be fixed to the anterior surface of the sacrum at the anterior target point, whereby the one of the elongated occluder or tubular member having the distal fixation mechanism attached to the anterior surface of the sacrum at the anterior target point forms an anterior percutaneous tract through presacral space.

* * * * *